(12) United States Patent
Inoue et al.

(10) Patent No.: US 10,519,421 B2
(45) Date of Patent: Dec. 31, 2019

(54) INDUCTION OF MOTOR NEURONS FROM PLURIPOTENT STEM CELLS

(71) Applicant: KYOTO UNIVERSITY, Kyoto (JP)

(72) Inventors: Haruhisa Inoue, Kyoto (JP); Keiko Imamura, Kyoto (JP); Takayuki Kondo, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/778,670

(22) PCT Filed: Mar. 24, 2014

(86) PCT No.: PCT/JP2014/058142
§ 371 (c)(1),
(2) Date: Sep. 21, 2015

(87) PCT Pub. No.: WO2014/148646
PCT Pub. Date: Sep. 25, 2014

(65) Prior Publication Data
US 2016/0046905 A1 Feb. 18, 2016

(30) Foreign Application Priority Data

Mar. 21, 2013 (JP) ................. 2013-058922
Jul. 31, 2013 (JP) ................. 2013-159375
Jan. 15, 2014 (JP) ................. 2014-005507

(51) Int. Cl.
*C12N 5/0793* (2010.01)
*C12N 5/074* (2010.01)
*C12N 5/078* (2010.01)
*G01N 33/569* (2006.01)

(52) U.S. Cl.
CPC ......... *C12N 5/0619* (2013.01); *C12N 5/0607* (2013.01); *C12N 5/0641* (2013.01); *G01N 33/56966* (2013.01); *G01N 2500/04* (2013.01); *G01N 2500/10* (2013.01)

(58) Field of Classification Search
CPC .. C12N 5/0607; C12N 5/0641; C12N 5/0619; C12N 5/0645; C12N 2500/25; C12N 2500/42; C12N 2501/13; C12N 2501/39; C12N 2501/41; C12N 2501/60; C12N 2506/02; C12N 2506/115; C12N 2506/45; C12N 2510/00; G01N 33/5073; G01N 33/56966; G01N 2500/04; G01N 2500/10; G01N 2800/2835; G01N 2800/52
See application file for complete search history.

(56) References Cited

U.S. PATENT DOCUMENTS 5,843,780 A 12/1998 Thomson
8,048,999 B2 11/2011 Yamanaka
2004/0121461 A1 6/2004 Honmou
2004/0136973 A1 7/2004 Huberman
2009/0068742 A1 3/2009 Yamanaka
2012/0142093 A1 6/2012 Morizane

FOREIGN PATENT DOCUMENTS

JP 2010260873 A2 11/2010
WO 2007069666 A1 6/2007
WO 2011019092 A1 2/2011
WO 2013025963 A2 2/2013

OTHER PUBLICATIONS

Kay, Nature Reviews Genetics, advance online publication, pp. 1-13, published online Apr. 6, 2011.*
Gonzalez et al., PNAS, 106(22): 8918-8922, 2009.*
Karumbayaram et al., Disease Models and Mechanisms, 2: 189-195, 2009.*
Wobus et al. Physiol. Rev., 85: 635-678 (2005).*
Llaguno et al., Cancer Cell, 15(10): 45-56, 2009.*
Lee, PNAS, 109(9): 3383-3388, 2012, including Supplementary Materials and Methods.*
Mariani et al., Gene, 563: 109-114, 2015.*
Extended European Search Report dated Jan. 3, 2017 issued in the corresponding European patent application No. 14769825.2.
Hester M E et al., "Rapid and efficient generation of functional motor neurons from human pluripotent stem cells using gene delivered transcription factor codes," Molecular Therapy, vol. 19, No. 10, pp. 1905-1912, Oct. 2011.; Cited in EESR.
International Search Report dated Jun. 24, 2014 filed in PCT/JP2014/058142.
Watanabe,K., et al., "Directed differentiation of telencephalic precursors from embryonic stem cells," Nat. Neurosci., 8:288-296, 2005.; English abstract only; Cited in Specification.
Kawasaki, H., et al., "Induction of midbrain dopaminergic neurons from ES cells by stromal cell-derived inducing activity," Neuron, 28:31-40, 2000.; English abstract only; Cited in Specification.
Chambers, S.M., et al., "Highly efficient neural conversion of human ES and iPS cells by dual inhibition of SMAD signaling," Nat. Biotechnol., 27:275-280, 2009.; English abstract only; Cited in Specification.

(Continued)

*Primary Examiner* — Thaian N Ton
(74) *Attorney, Agent, or Firm* — Rankin, Hill & Clark LLP

(57) ABSTRACT

The present invention aims to provide a method of producing motor neurons/neurons that sufficiently reproduce intrinsic properties of motor neurons/neurons, especially of the motor neurons/neurons in patients, from pluripotent stem cells promptly and synchronically, and a pluripotent stem cell capable of differentiating into a neuron or a motor neuron promptly and synchronically after a drug treatment. A method of generating a motor neuron from a pluripotent stem cell, comprising the following steps in order from (1) to (2):
(1) introducing one or more nucleic acids encoding Lhx3, Ngn2, and Isl1 into a pluripotent stem cell; and
(2) maintaining expression of the Lhx3, Ngn2, and Isl1 for three days or more.

7 Claims, 19 Drawing Sheets

(56) References Cited

OTHER PUBLICATIONS

Hester, M.E., et al., "Rapid and efficient generation of functional motor neurons from human pluripotent stem cells using gene delivered transcription factor codes," Mol. Therapy, 19:1905-1912, 2011.; English abstract only; Cited in Specification.

Pang, Z.P., et al., "Induction of human neuronal cells by defined transcription factors," Nature, 476:220-223, 2011.; English abstract only; Cited in Specification.

Lee Seunghee et al., "Fusion protein Isl1-Lhx3 specifies motor neuron fate by inducing motor neuron genes and concomitantly suppressing the interneuron programs," PNAS, 2012, vol. 109 No. 9, pp. 3383-3388.; Cited in International Search Report.

Thoma Eva C. et al., "Ectopic Expression of Neurogenin 2 Alone is Sufficient to Induce Differentiation of Embryonic Stem Cells into Mature Neurons," PLoS One, 2012, vol. 7, Issue 6, pp. 1-13.; Cited in International Search Report.

Naoki Yahata et al., Idenshi Igaku MOOK, vol. 22, pp. 98-102, 2012.; Brief description in English included.; Cited in International Search Report.

Wilson Matthew H et al., PiggyBac Transposon-mediated Gene Transfer in Human Cells, Molecular Therapy, vol. 15, No. 1, pp. 139-145, 2007.; Cited in International Search Report.

Lai Helen C. et al., "Neurogenesis or Neuronal Specification: Phosphorylation Strikes Again!" Neuron 58, 2008, pp. 3-5.; Cited in International Search Report.

Mazzoni Esteban O et al., "Synergistic binding of transcription factors to cell-specific enhancers programs motor identity," Nature Neuroscience, vol. 16, No. 9, 2013, total 11 pages.; Cited in International Search Report.

Furler, S. et al., "Recombinant AAV vectors containing the foot and mouth disease virus 2A sequence confer efficient bicistronic gene expression in cultured cells and rat substantia nigra neurons", Gene Therapy, 2001, vol. 8, p. 864-873, Nature Publishing Group, United Kingdom.

Hasegawa, Kouichi et al., "Efficient Multicistronic Expression of a Transgene in Human Embryonic Stem Cells", Stem Cells, 2007, vol. 25, p. 1707-1712, www.StemCells.com, Wiley Online, USA.

Szymczak, Andrea L. et al., "Correction of multi-gene deficiency in vivo using a single 'self-cleaving' 2A peptide-based retroviral vector", Nature Biotechnology, 2004, vol. 22 No. 5, p. 589-594, Nature Publishing Group, United Kingdom.

Aoki, Masashi et al., "Amyotrophic lateral sclerosis with the SOD1 mutations", Clinical Neurology, 2008, vol. 48, p. 966-969, Elsevier, The Netherlands.; English Abstract.

* cited by examiner

[Fig. 1]
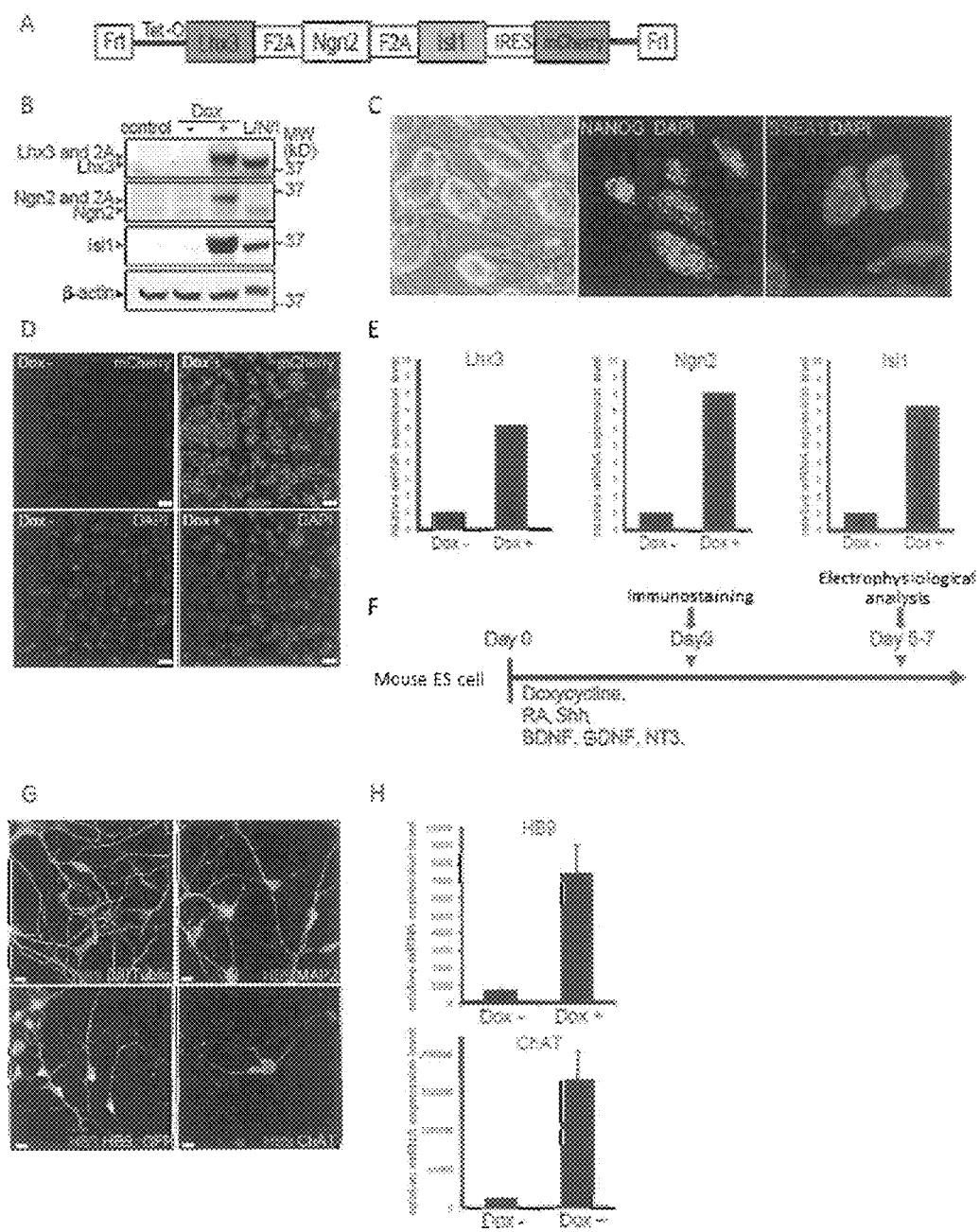

[Fig. 2]
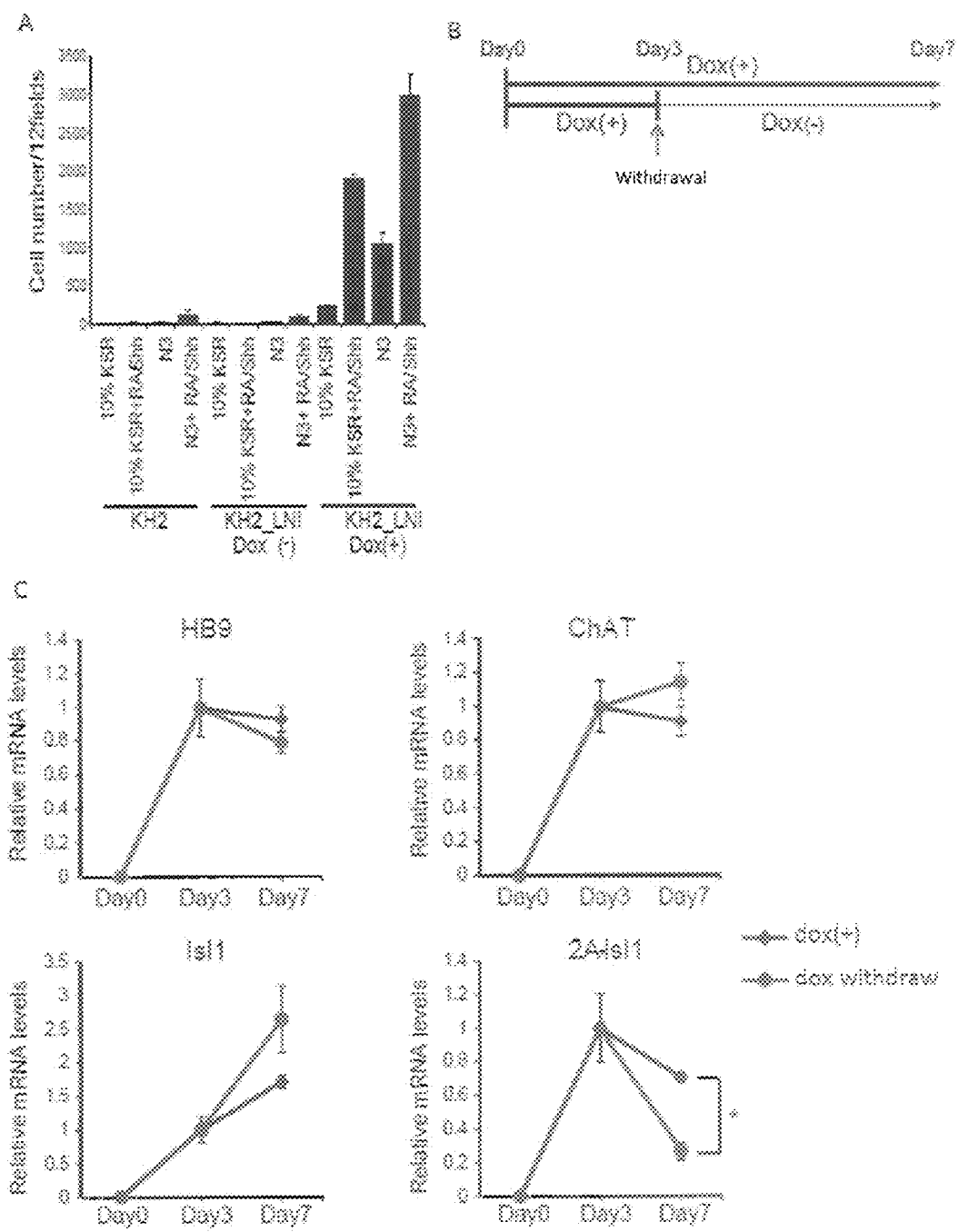

[Fig. 3]
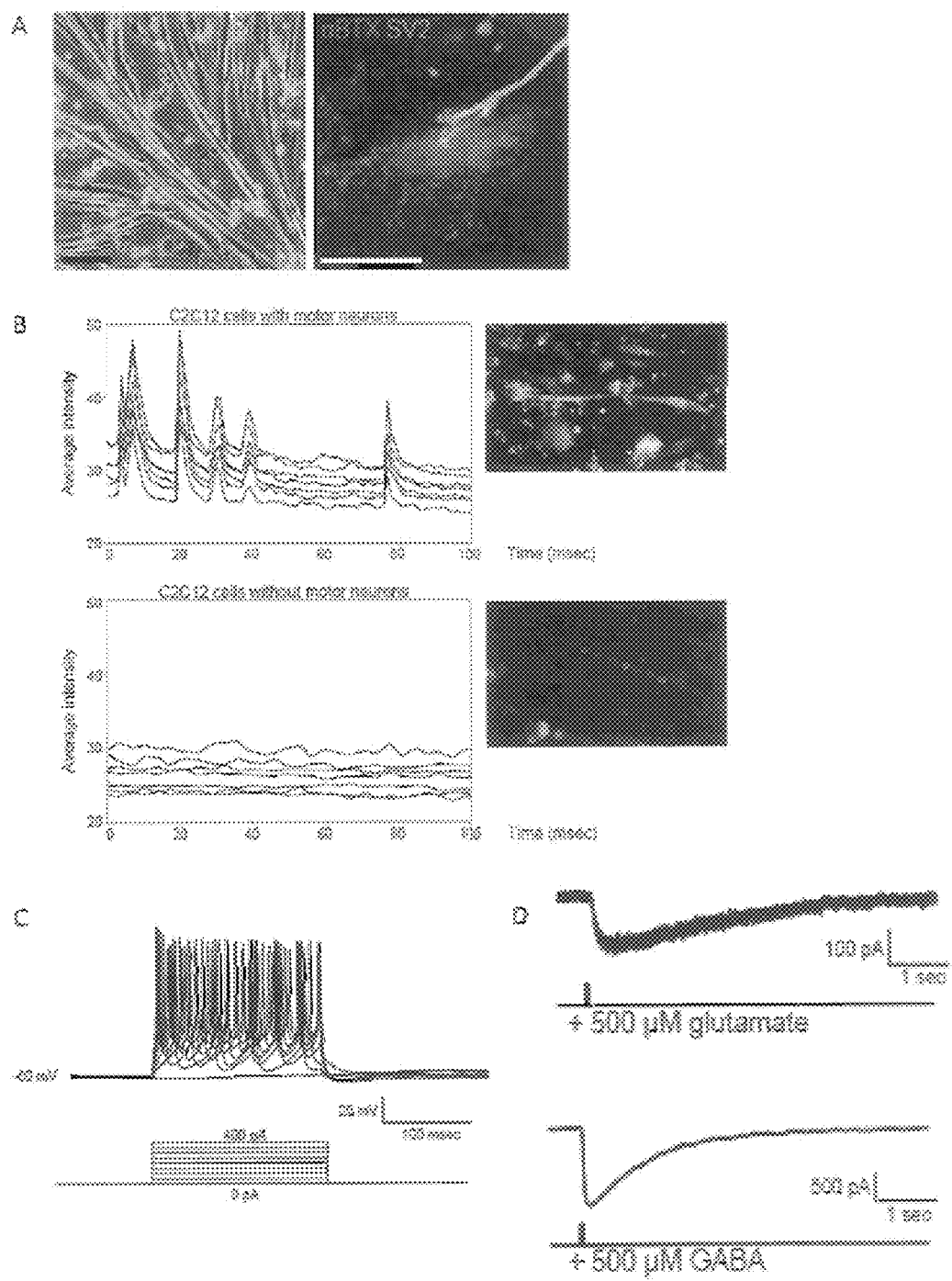

[Fig. 4]
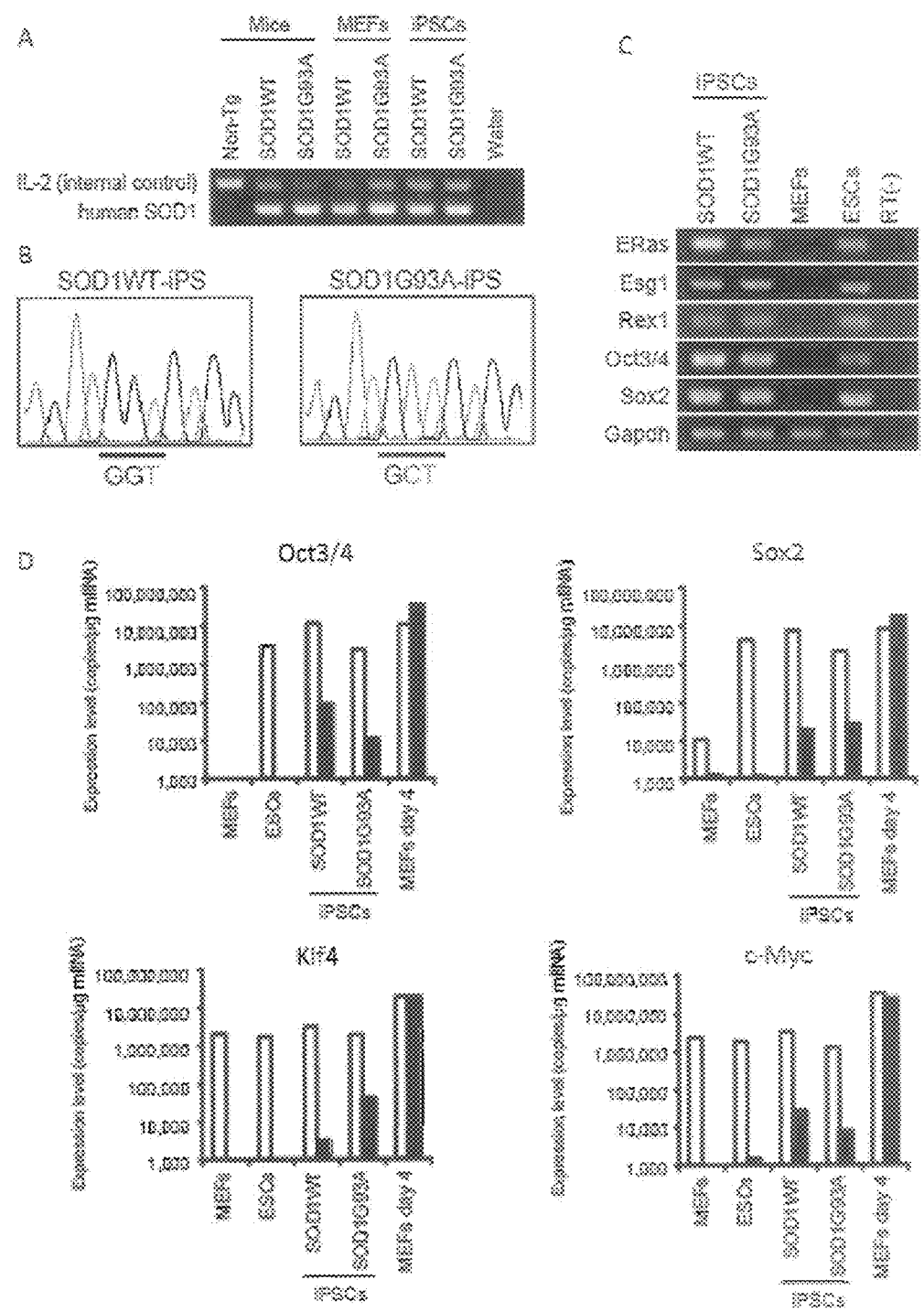

[Fig. 5]
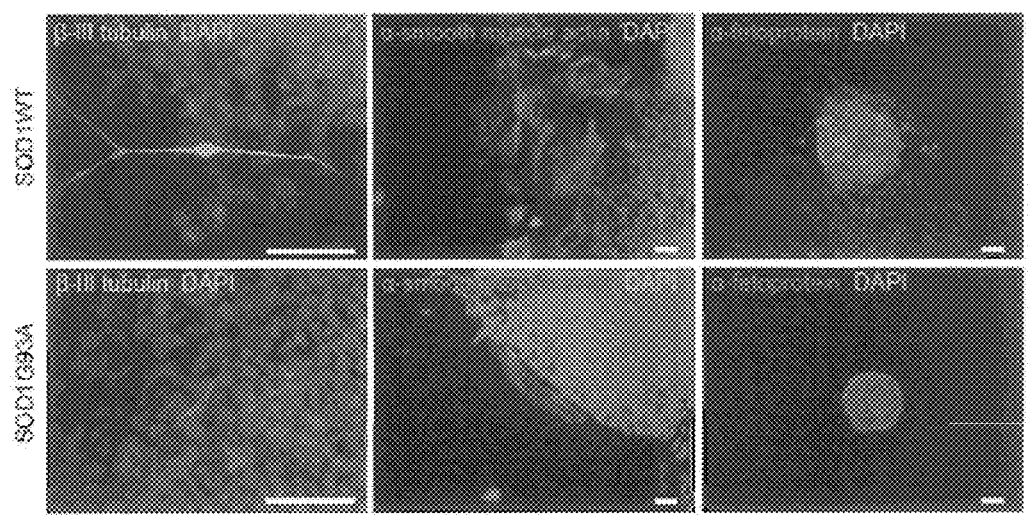

[Fig. 6]
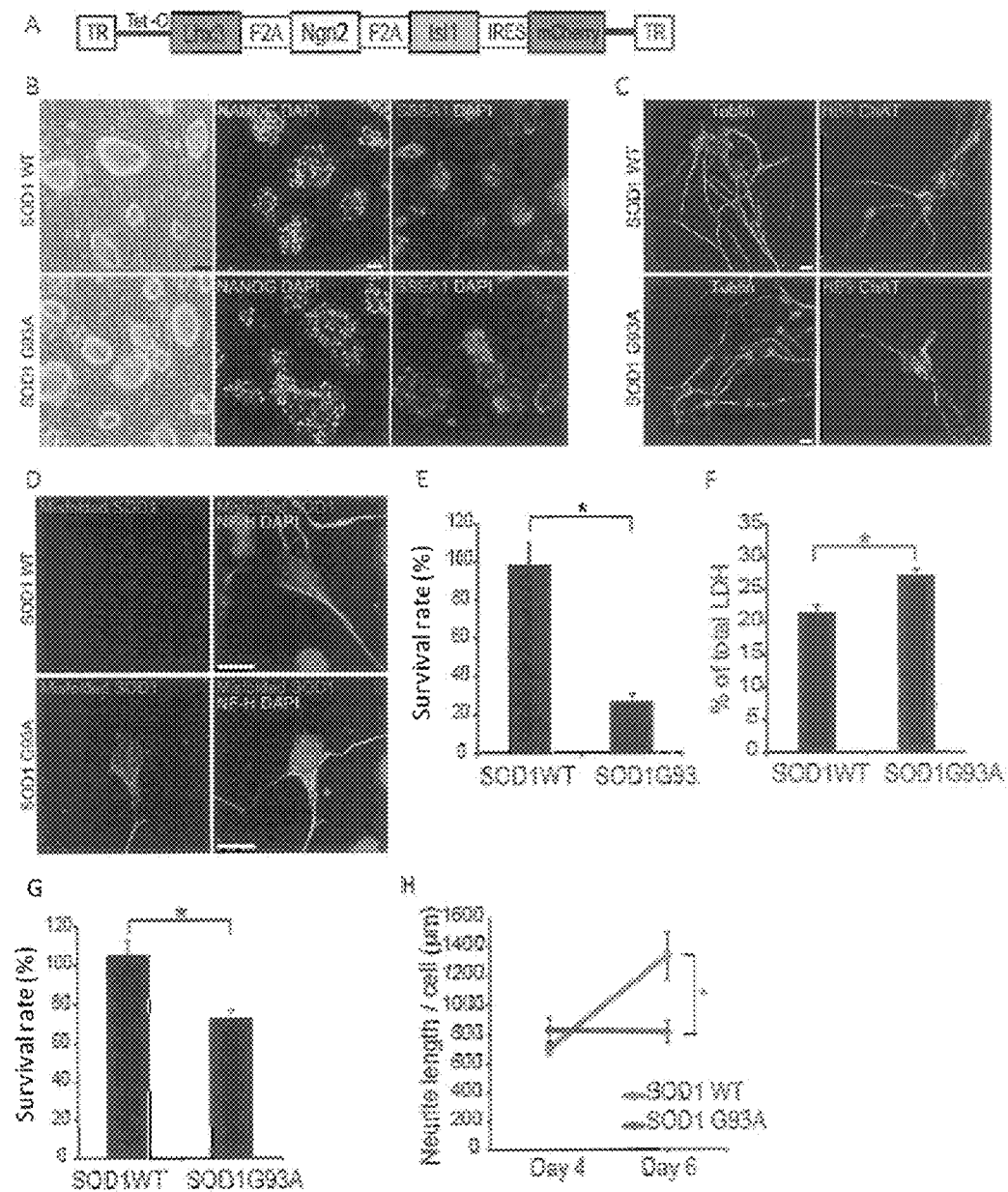

[Fig. 7]
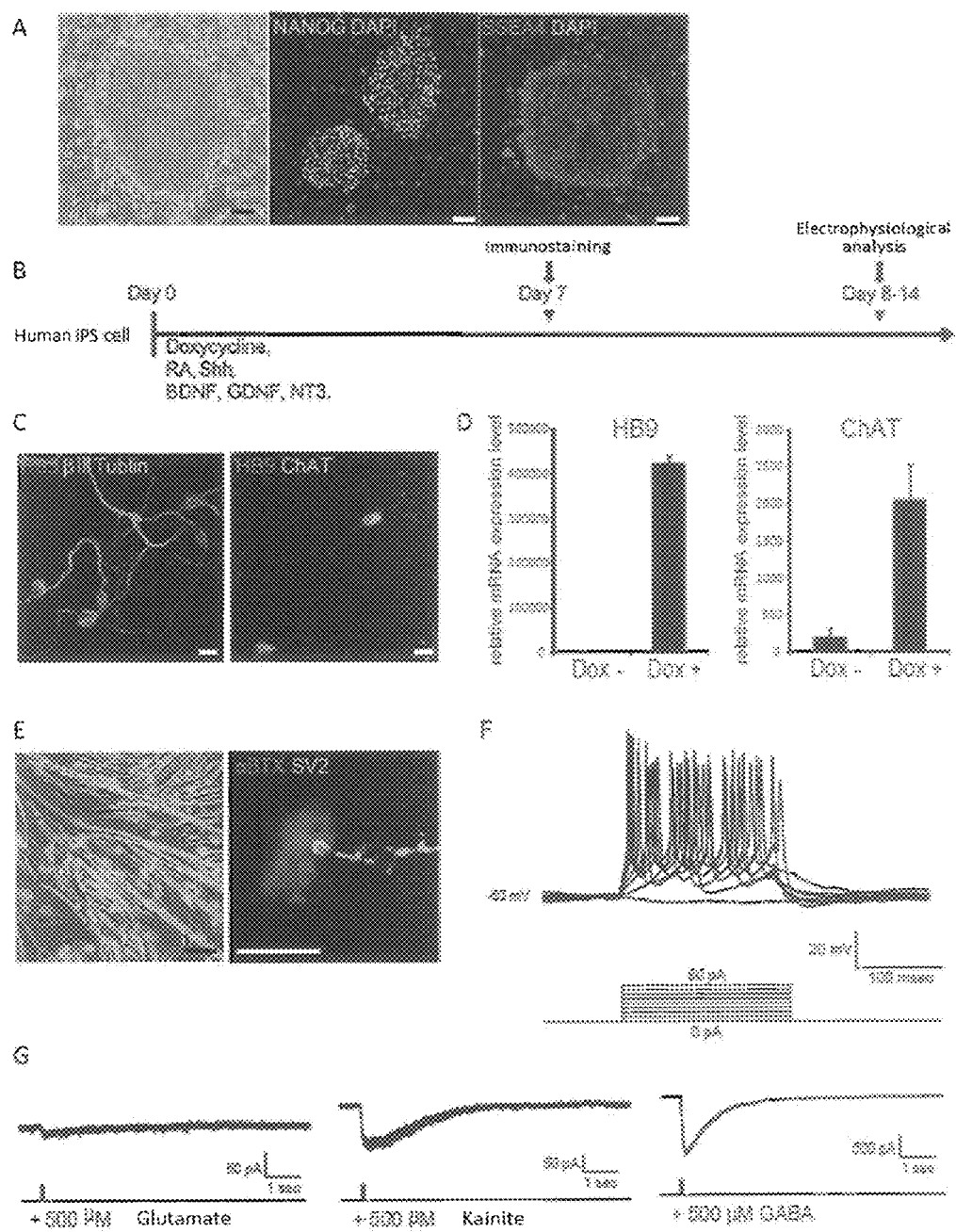

[Fig. 8]
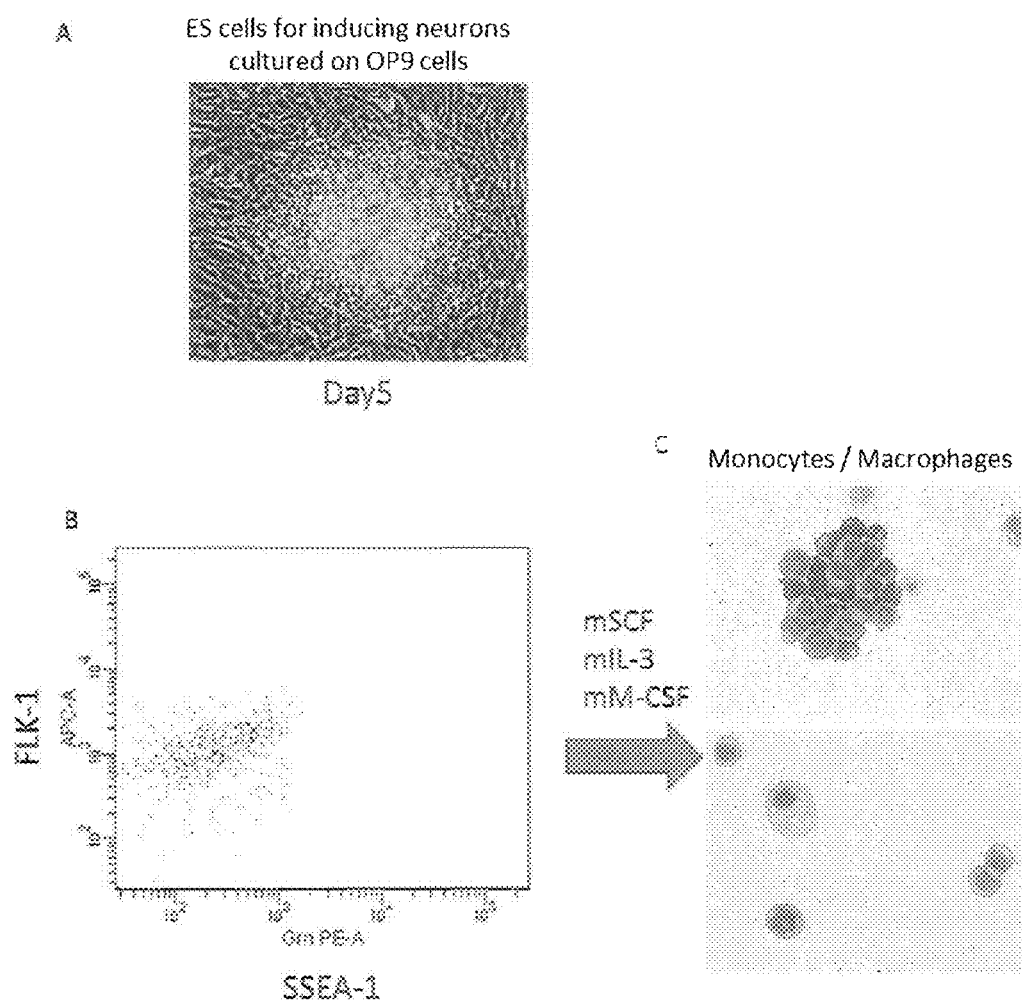

[Fig. 9]
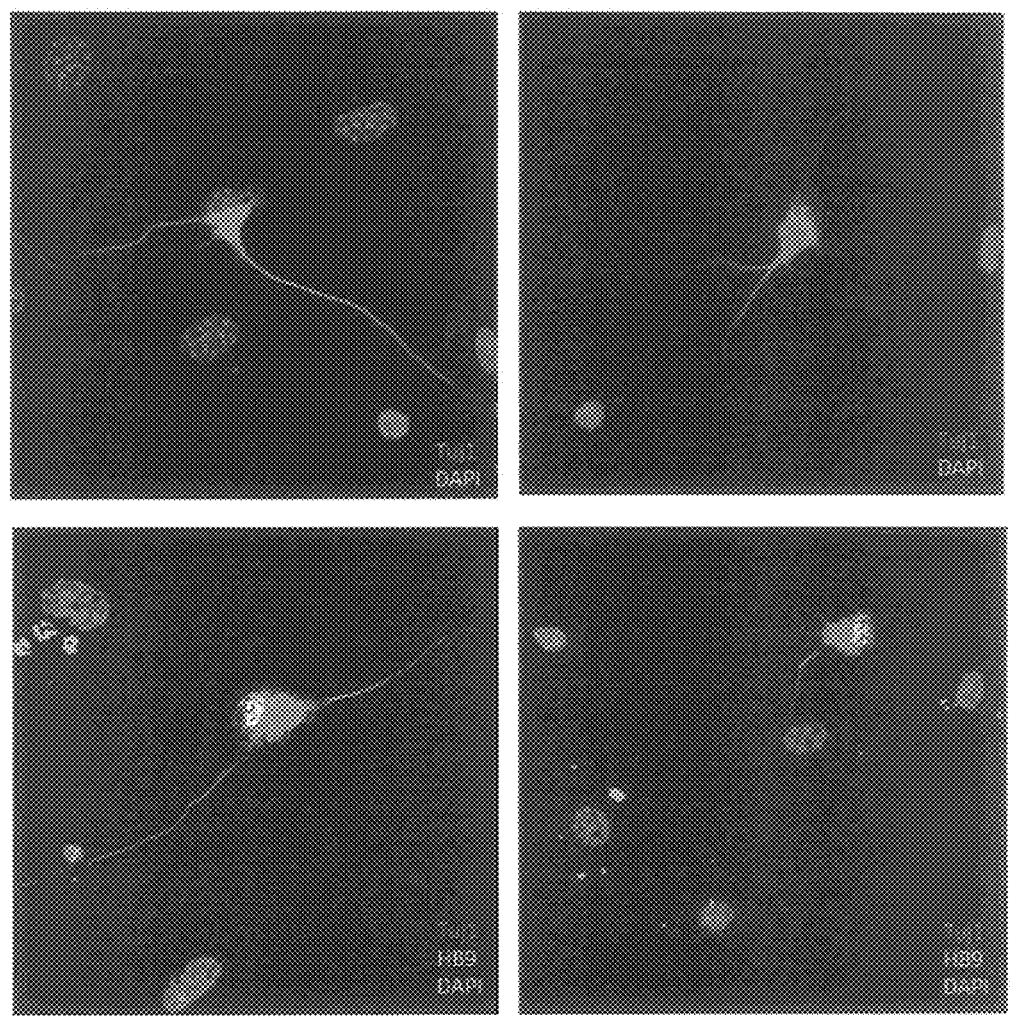

[Fig. 10]
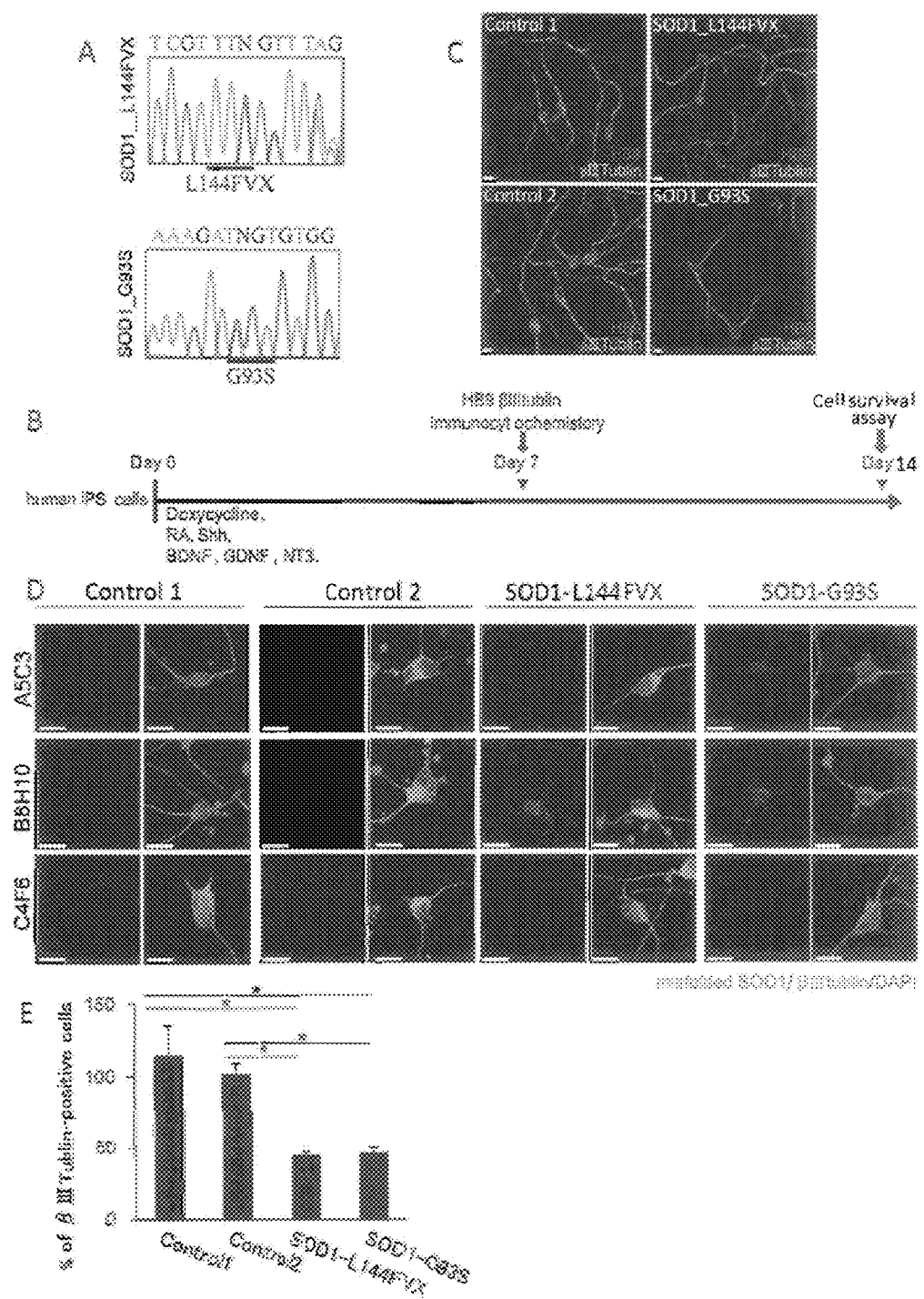

[Fig. 11]
A : Induction of mouse MN (0 – 72 hr)
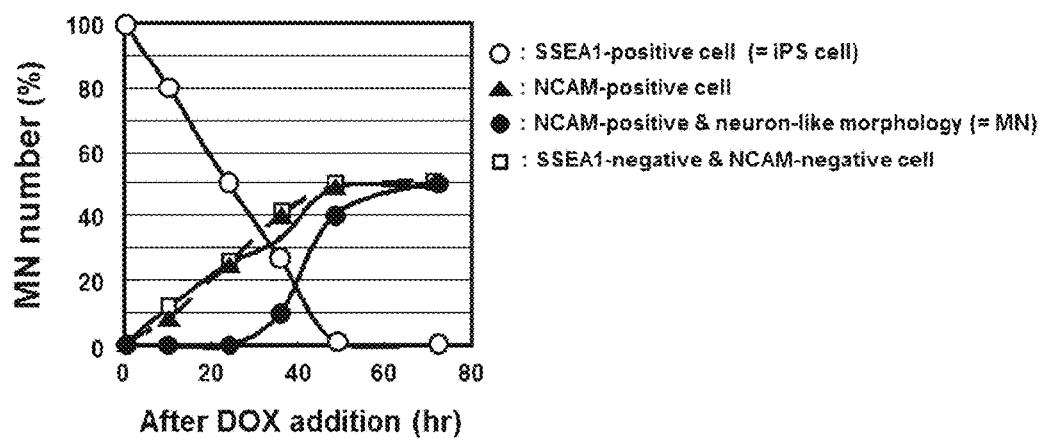
B : Induction of human MN (Day0 – Day7)
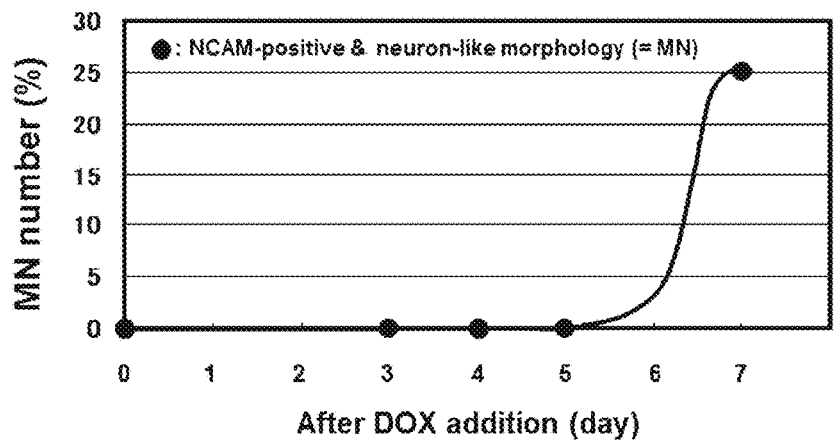

[Fig. 12]
A : Induction of mouse MN (Day0 – Day10)
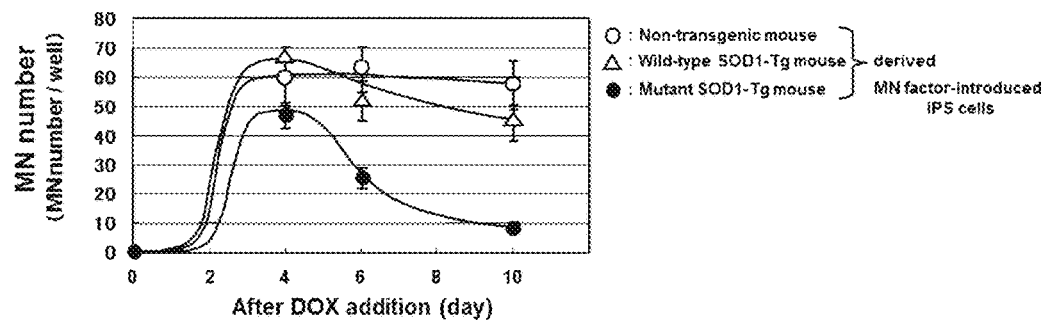
B : Induction of human MN (Day0-Day14)
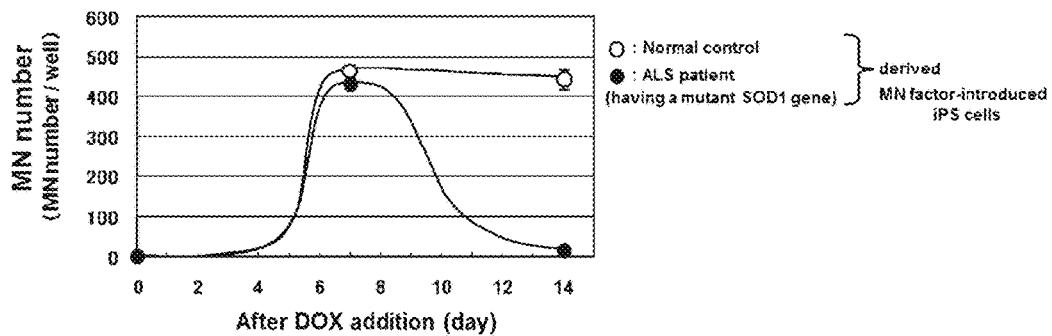

[Fig. 13]
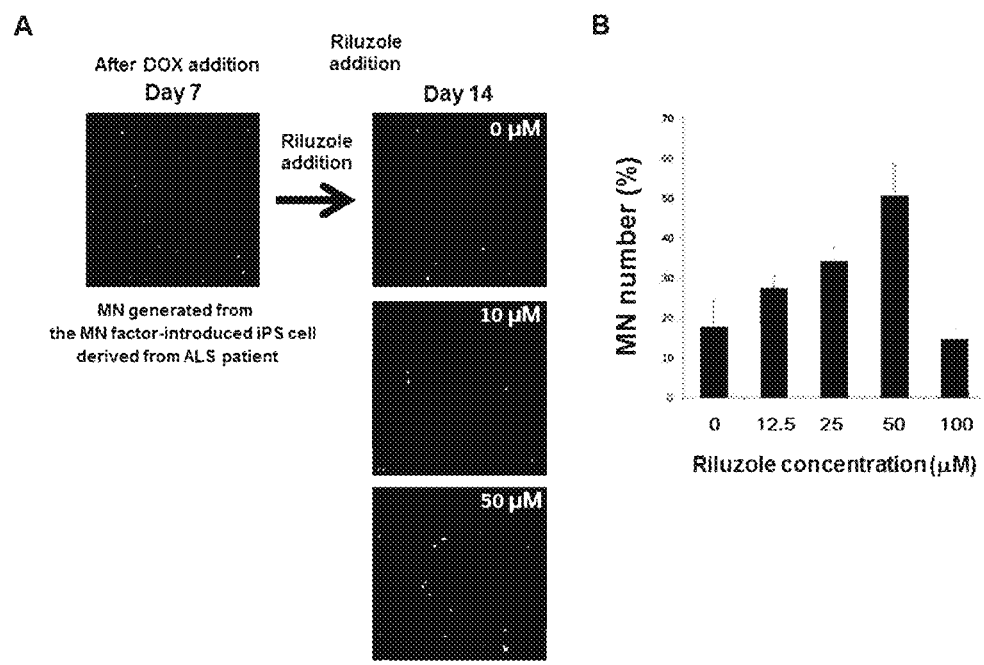

[Fig. 14]
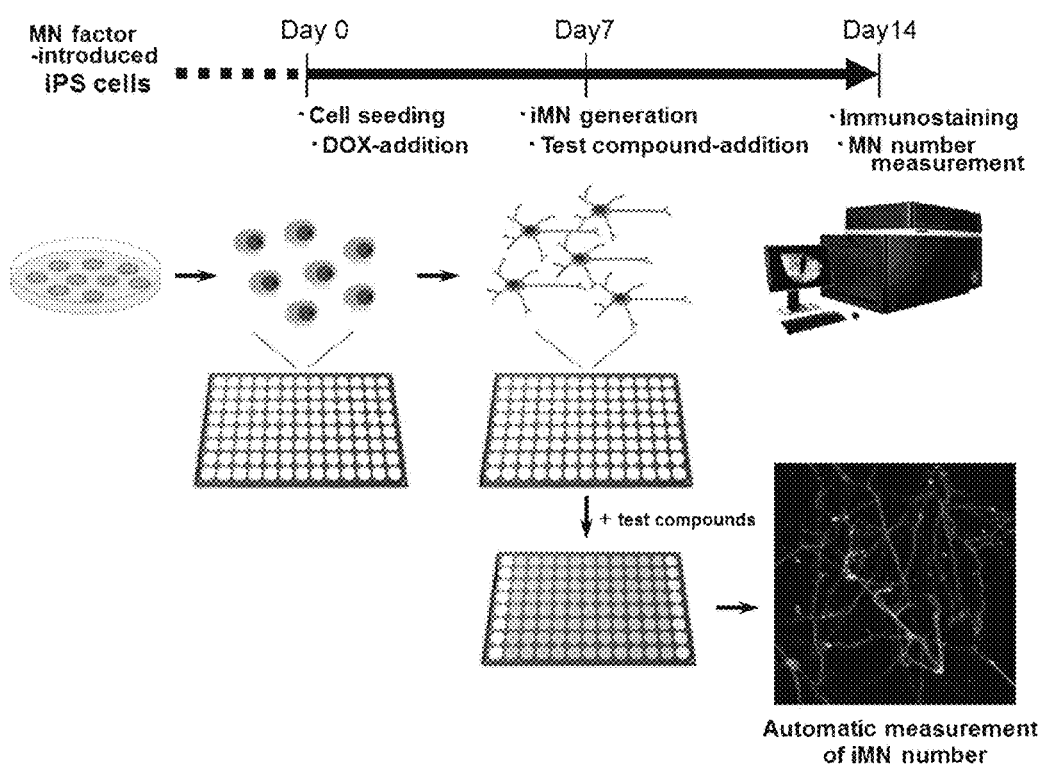

[Fig. 15]
A : Evaluation of accuracy (Z'-score)
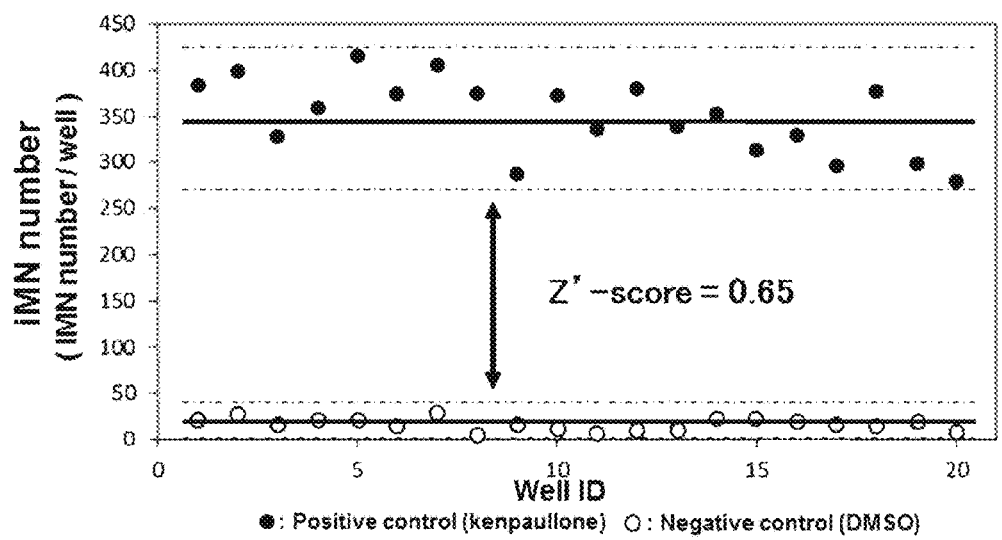
B : Screening results of existing drugs
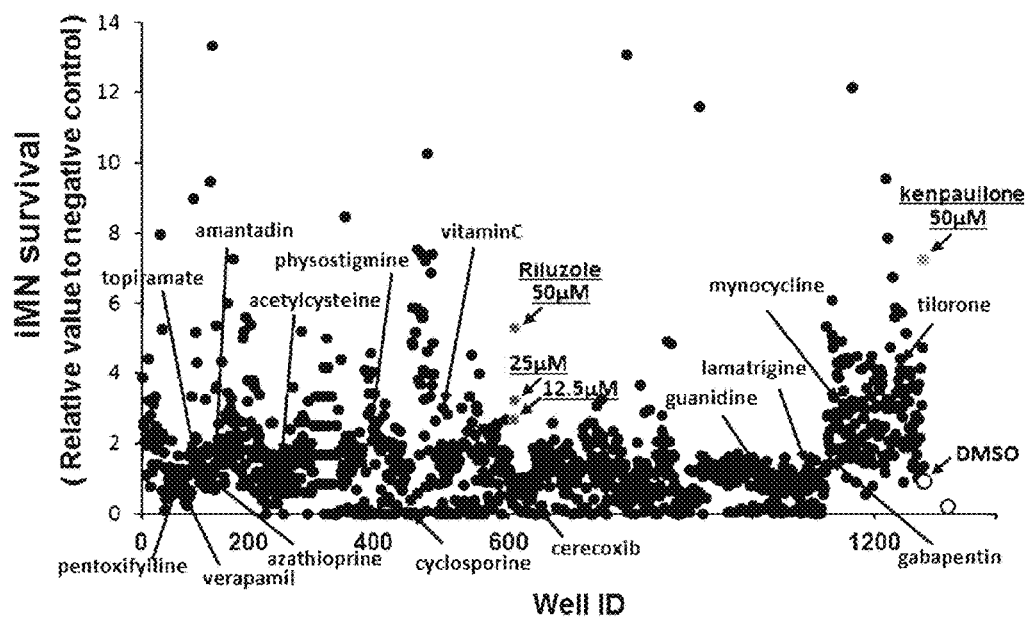

[Fig. 16]
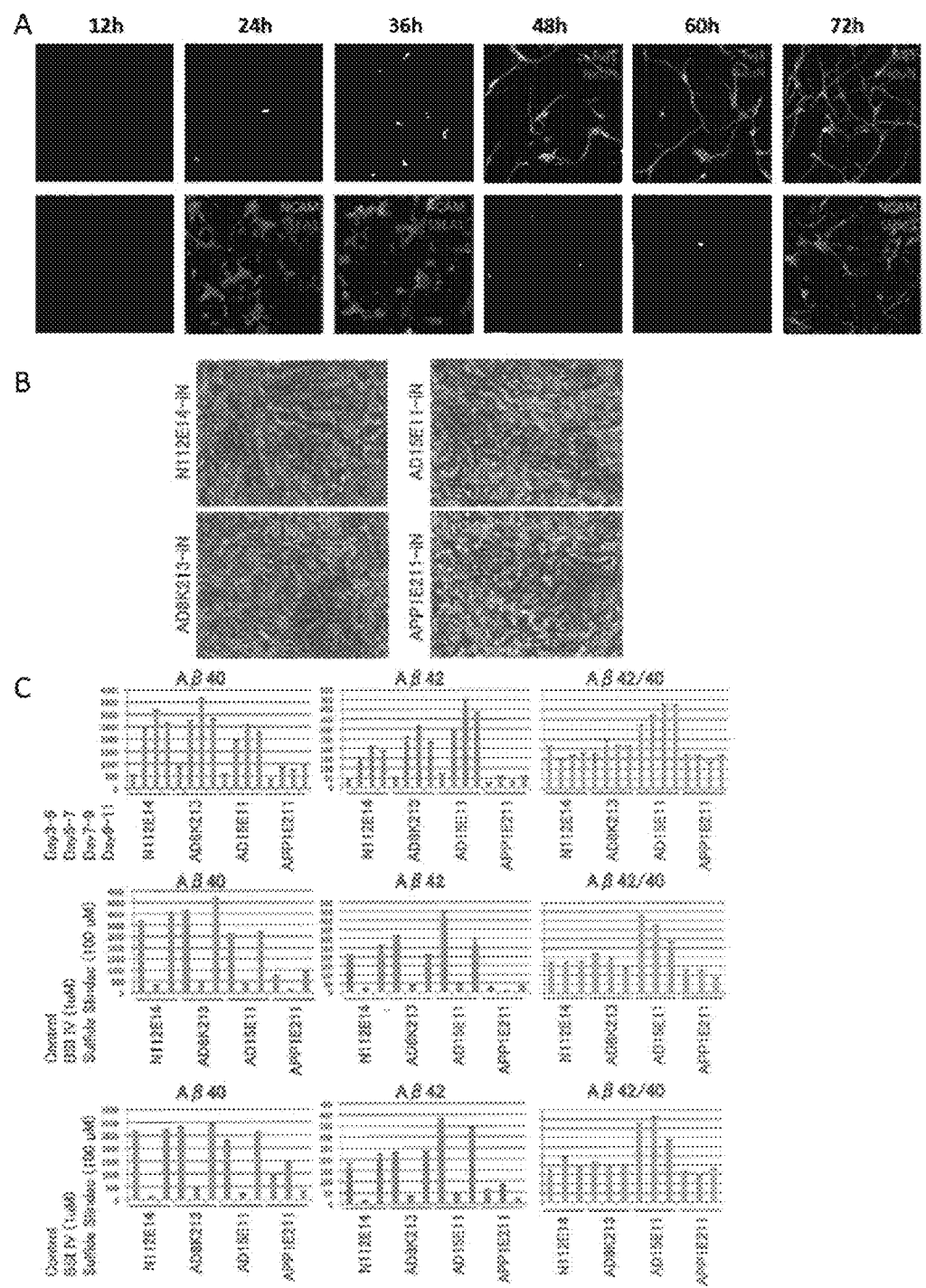

[Fig. 17]
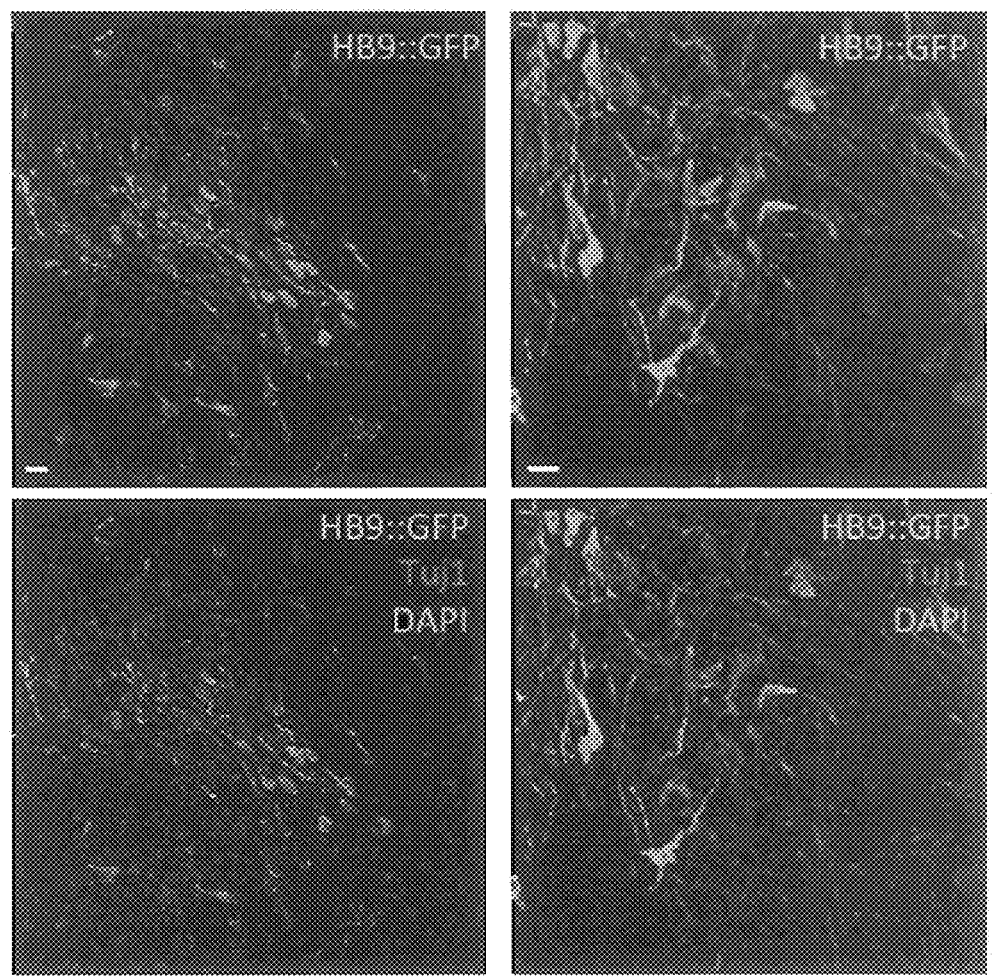

[Fig. 18]
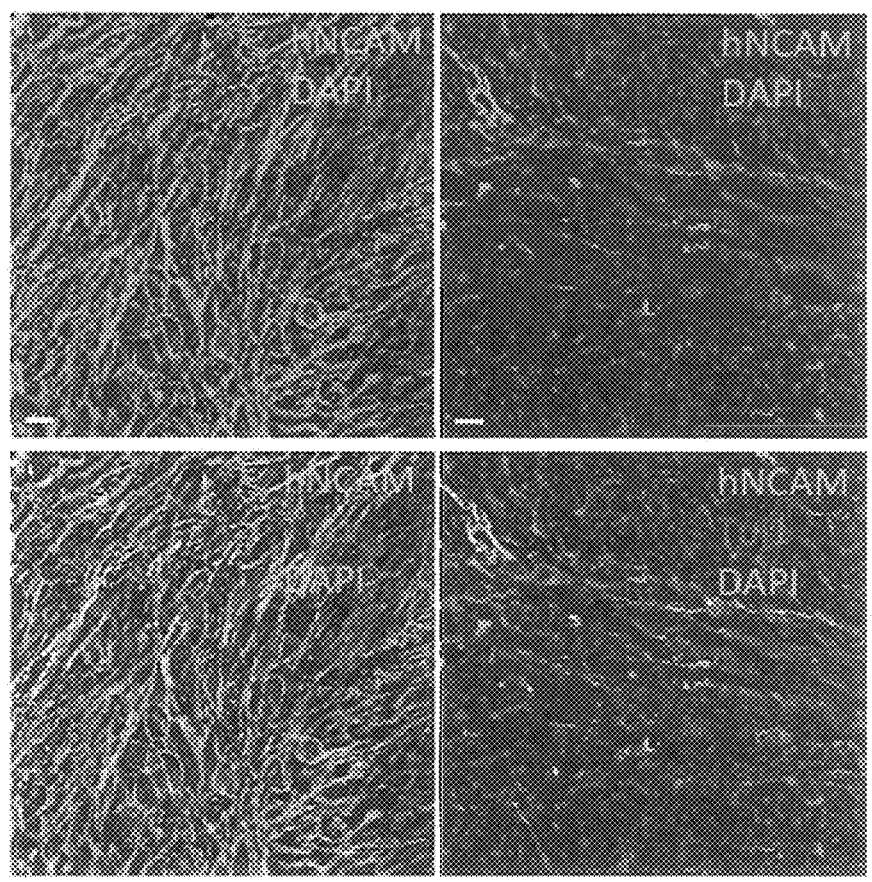

[Fig. 19]
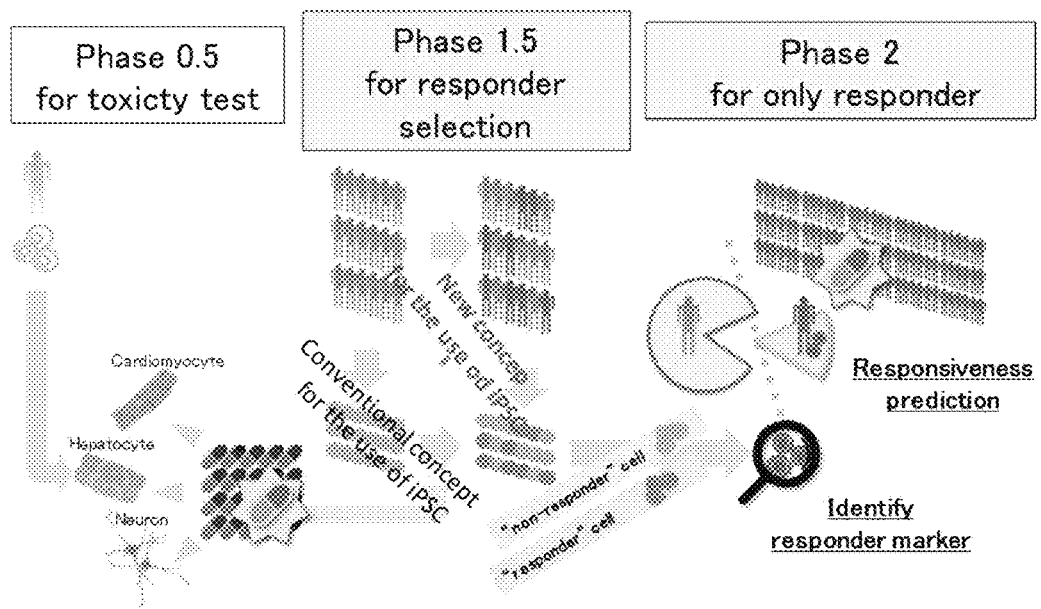

INDUCTION OF MOTOR NEURONS FROM PLURIPOTENT STEM CELLS

RELATED APPLICATIONS

This application claims the priority of Japanese Patent Applications No. 2013-58922 filed on Mar. 21, 2013, No. 2013-159375 filed on Jul. 31, 2013, and No. 2014-5507 filed on Jan. 15, 2014, which are incorporated herein by reference.

TECHNICAL FIELD

The present invention relates to a method of generating a neuron or a motor neuron from a pluripotent stem cell. Furthermore, the present invention relates to a pluripotent stem cell capable of differentiating into a neuron or a motor neuron immediately after a drug treatment.

BACKGROUND ART

Since neurons cannot be collected from a patient with neurodegenerative disease or spinal cord injury resulting from a damage in specific neurons, studies regarding the pathogenic mechanism thereof and the development of a therapeutic method therefor largely depend on an analysis system using model animals. However, in recent years, a case in which a drug that has been effective for a model animal does not show effectiveness in human clinical trials has frequently occurred, and thus, the limitation of studies using animal models has been pointed out. Hence, it has been strongly expected that human-derived neurons, which are produced from human-derived pluripotent stem cells (i.e., embryonic stem cells (ES cells) or induced pluripotent stem cells (iPS cells) as a result of differentiation; see Patent Literatures 1 and 2), will be used as an analysis system, a drug screening system, and further, a cell preparation.

As methods of inducing differentiation of pluripotent stem cells into neural cells, methods of determining cell fates by on extrinsic signals from outside of the cells, such as a method which comprises forming an embryoid body (a cell mass comprising neural progenitor cells) in a serum-free medium and then allowing it to differentiate into neural cells (SFEB method) (Non Patent Literature 1), a method which comprises culturing embryonic stem cells on stromal cells and then allowing the cultured cells to differentiate into neural cells (SDIA method) (Non Patent Literature 2), a method which comprises culturing the pluripotent stem cells with a drug on matrigel (Non Patent Literature 3), and a method using a low molecular weight compound as an alternative to cytokine (Patent Literature 1), have been mainly used so far. However, these methods have been problematic in that it takes a long period of time, such as several months, to obtain neurons of interest, and also in that since the synchrony in differentiation is extremely low, a uniform cell population cannot be obtained. These problems have been pointed out as causes for insufficient reproducibility in data, when the neurons obtained by the above described methods are used in drug screening or cell transplantation. Moreover, there have been reported many cases in which the neurons obtained by these methods do not sufficiently possess intrinsic properties of neurons, or do not reproduce a phenomenon characteristic to the disease (a pathological hallmark) when prepared from pluripotent stem cells derived from a patient with neurodegenerative disease.

Hence, a method of producing neurons from pluripotent stem cells in a short time has been attempted by introducing a forcible expression of certain transcription factors that are scheduled to be expressed in neuronal cell lineage in the process of development. Non Patent Literature 4 discloses a method in which human-derived embryonic stem cells or induced pluripotent stem cells are differentiated into neural progenitor cells by the SFEB method, and then, three types of (motor) neuron lineage-specific transcription factors (Ngn2, Lhx3, and Isl1) are introduced and allowed to express in the neural progenitor cells, so that motor neurons can be obtained 11 days after the introduction. In addition, Non Patent Literature 5 discloses a method in which three types of neuron lineage-specific transcription factors (Ascl1, Brn2, and Mytl1) are introduced and allowed to express in human embryonic stem cells, so that neurons can be obtained approximately 6 days after the introduction.

Thus, a neuron whose differentiation has been induced by the expression of an exogenous gene(s) is referred to as "induced neuron (which is abbreviated as "iN")," in order to distinguish a neuron whose differentiation has been induced by a signal from the outside of the cells. When the neuron is a motor neuron, the motor neuron is referred to as "induced motor neuron (which is abbreviated as "iMN")". As described above, iMN and iN are obtained in an extremely short time, in comparison to the conventional method for producing motor neurons/neurons. However, it cannot be said that the synchrony in differentiation is sufficient, and further, there are harsh opinions regarding the level of reproducibility of the original properties of motor neurons/neurons (in particular, when iMN or iN is derived from a patient with a disease).

Accordingly, a method of producing a motor neuron or a neuron, that sufficiently possesses an intrinsic property of motor neurons/neurons, including a pathological property in patients, from a pluripotent stem cell promptly and synchronically, has been sought-after.

CITATION LIST

Patent Literature

[PTL 1] U.S. Pat. No. 5,843,780
[PTL 2] WO2007/069666
[PTL 3] WO2011/019092

Non Patent Literature

[NPL 1] Watanabe, K., et al., Nat. Neurosci., 8:288-296, 2005.
[NPL 2] Kawasaki, H., et al., Neuron, 28:31-40, 2000).
[NPL 3] Chambers, S. M., et al., Nat.Biotechnol., 27:275-280, 2009.
[NPL 4] Hester, M. E., et al., Mol. Therapy, 19:1905-1912, 2011.
[NPL 5] Pang, Z. P., et al., Nature, 476:220-223, 2012.

SUMMARY OF INVENTION

Technical Problem

The present invention was made in view of the above-described circumstances, and an object is to provide a method of producing motor neurons/neurons that sufficiently reproduce intrinsic properties of motor neurons/neurons, especially of the motor neurons/neurons in patients, from pluripotent stem cells promptly and synchronically.

Furthermore, the present invention aims to provide the pluripotent stem cells capable of differentiating into neurons or motor neurons immediately after a drug treatment.

Solution to Problem

The present inventors have diligently studied to achieve the above-described objects and discovered that an introduction of Ngn2, Lhx3, and Isl1 genes into a pluripotent stem cell followed by an induction of the expression of said genes causes a more prompt and synchronized differentiation into a motor neuron, than when those genes are introduced into a neural progenitor cell and the gene expression is induced. Moreover, it was clarified that a motor neuron generated from an iPS cell derived from a patient with amyotrophic lateral sclerosis (ALS) using the present method autonomously undergoes cell death, and the cell death can be efficiently suppressed by an ALS therapeutic agent.

Furthermore, the present inventors discovered that, among the above three genes, an introduction of Ngn2 gene alone into a pluripotent stem cell followed by an induction of the expression of said gene causes a prompt and synchronized differentiation into a neuron. In addition, it was clarified that a neuron generated from an iPS cell derived from a patient with Alzheimer's type dementia produces Aβ peptide in a manner characteristic to the disease.

Based on those findings, the present inventors completed the invention.

That is, the present invention provides the following.

[1] A method of generating a motor neuron from a pluripotent stem cell, comprising the following steps in order from (1) to (2):

(1) introducing one or more nucleic acids encoding Lhx3, Ngn2, and Isl1 into a pluripotent stem cell;

(2) maintaining the expression of Lhx3, Ngn2, and Isl1 for three days or more.

[2] The method according to [1], wherein said nucleic acids are introduced into the cell using a transposon.

[3] The method according to [2], wherein said transposon is a piggyBac transposon.

[4] The method according to any of [1] to [3], wherein the expression of Lhx3, Ngn2, and Isl1 is driven by a drug-responsive promoter.

[5] The method according to [4], wherein said drug-responsive promoter is a tetracycline-responsive promoter.

[6] The method according to [1], wherein Lhx3, Ngn2, and Isl1 are polycistronically expressed from the nucleic acid.

[7] The method according to [6], wherein the nucleic acid encoding Lhx3, Ngn2, or Isl1 is connected via a nucleic acid encoding a 2A sequence.

[8] The method according to any of [1] to [7], wherein the expression of Lhx3, Ngn2, and Isl1 is maintained for 7 days or more in step (2).

[9] The method according to any of [6] to [8], wherein step (2) further comprises steps of introducing the cell obtained in step (1) into an animal body, and bringing the cell into contact with an agent corresponding to the drug-responsive promoters in the animal body.

[10] The method according to any of [1] to [9], wherein step (1) further comprises a step of inducing differentiation of the pluripotent stem cell in which said nucleic acid has been introduced, into blood cells.

[11] The method according to [10], wherein said blood cells are monocytes and/or macrophages.

[12] The method according to [10] or [11], wherein said step of inducing differentiation of the pluripotent stem cell into blood cells consists of culturing the pluripotent stem cell together with bone marrow-derived stromal cells in the presence of a stem cell factor, a macrophage-colony stimulating factor, and an interleukin-3.

[13] The method according to any of [1] to [12], wherein said pluripotent stem cell is an induced pluripotent stem cell derived from a human.

[14] The method according to any of [1] to [13], wherein said pluripotent stem cell has one or more mutant SOD1 genes.

[15] A method of identifying a marker specific to a subject for whom an investigational agent for motor neuron diseases or nerve injury has been confirmed to be effective (namely, a responder) or ineffective (namely, a non-responder), comprising the following steps of (1) to (3):

(1) producing induced pluripotent stem cells from somatic cells isolated from a responder and a non-responder;

(2) generating motor neurons from the induced pluripotent stem cells obtained in step (1), by the method according to any of [1]-[8];

(3) measuring an amount of gene products in the motor neurons derived from the responder and the non-responder, which were obtained in step (2); and (4) identifying a gene product which amount is higher in the motor neurons derived from the responder than in the motor neurons derived from the non-responder as the responder-specific marker, or a gene product which amount is lower in the motor neurons derived from the responder than in the motor neurons derived from the non-responder as the non-responder-specific marker.

[16] A method of selecting a subject for whom a therapeutic agent is effective, comprising the following steps of (1) to (3):

(1) producing induced pluripotent stem cells from somatic cells isolated from a subject;

(2) generating motor neurons from the induced pluripotent stem cells obtained in step (1), by the method according to any of [1]-[8];

(3) detecting the presence or absence of a marker in the motor neurons obtained in step (2), wherein the marker has been identified as a responder-specific or a non-responder-specific marker by the method according to [15]; and (4) selecting a subject as the subject for whom the therapeutic agent corresponding to said marker is effective, when the responder-specific marker has been detected, or the non-responder-specific marker has not been detected in the motor neurons derived from said subject.

[17] A pluripotent stem cell in which one or more exogenous nucleic acids encoding Lhx3, Ngn2, and Isl1 have been inserted into the chromosome.

[18] The pluripotent stem cell according to [17], wherein said nucleic acids express Lhx3, Ngn2, and Isl1 in a polycistronic manner under the control of an inducible promoter.

[19] The pluripotent stem cell according to [18], wherein said nucleic acids have been inserted into the chromosome by a transposon.

[20] The pluripotent stem cell according to [19], wherein said transposon is a piggyBac transposon.

[21] The pluripotent stem cell according to any of [17] to [20], wherein said nucleic acid is functionally connected to a drug-responsive promoter.

[22] The pluripotent stem cell according to [21], wherein said drug-responsive promoter is a tetracycline-responsive promoter.

[23] The pluripotent stem cell according to any of [18] to [22], wherein the nucleic acid encoding Lhx3, Ngn2, or Isl1 is connected via a nucleic acid encoding 2A sequence.

[24] The pluripotent stem cell according to any of [17] to [23], wherein said pluripotent stem cell is an induced pluripotent stem cell derived from a human.

[25] The pluripotent stem cell according to any of [17] to [24], wherein said pluripotent stem cell has one or more mutant SOD1 genes.

[26] Blood cells differentiated from the pluripotent stem cell according to any of [17]-[24].

[27] The blood cells according to [26], wherein said blood cells are monocytes and/or macrophages.

[28] A therapeutic composition for motor neuron disease or nerve injury, comprising a pluripotent stem cell according to any of [17]-[24] as an effective ingredient.

[29] The therapeutic composition according to [28], wherein said motor neuron disease is amyotrophic lateral sclerosis.

[30] A therapeutic composition for motor neuron disease or nerve injury, comprising the blood cells according to [26] or [27] as an effective ingredient.

[31] The therapeutic composition according to [30], wherein said motor neuron disease is amyotrophic lateral sclerosis.

[32] A method for screening a therapeutic agent for amyotrophic lateral sclerosis, comprising the following steps of (1) to (5):
(1) generating motor neurons from induced pluripotent stem cells by the method according to any of [1]-[8], wherein the induced pluripotent stem cells have been produced from somatic cells isolated from a patient with amyotrophic lateral sclerosis;
(2) bringing a test substance into contact with the motor neurons obtained in step (1);
(3) culturing the motor neurons which have been contacted with the substance in step (2) and the motor neurons which have not been contacted with the substance (i.e., control cells);
(4) measuring the cell number and/or the neurite length of the motor neurons obtained through step (3);
(5) selecting a test substance as the therapeutic agent for amyotrophic lateral sclerosis, when the value of the cell number and/or the neurite length of the motor neurons which have been contacted with said substance is higher than the value of the control cells.

[33] The method according to [32], wherein said somatic cells have one or more mutations in SOD1 gene.

[34] A method of generating a neuron from a pluripotent stem cell, comprising the following steps in order from (1) to (2):
(1) introducing a nucleic acid encoding Ngn2 into a pluripotent stem cell using a transposon; and
(2) inducing an activation of the promotor and maintaining expression of the Ngn2 for three days or more.

[35] The method according to [34], wherein said transposon is a piggyBac transposon.

[36] The method according to [34] or [35], wherein the expression of Ngn2 is driven by a drug-responsive promoter.

[37] The method according to [36], wherein said drug-responsive promoter is a tetracycline-responsive promoter.

[38] The method according to any of [34] to [37], wherein the expression of Ngn2 is maintained for 7 days or more in step (2).

[39] The method according to any of [34] to [38], wherein step (2) further comprises steps of introducing the cells obtained in step (1) into an animal body, and subsequently bringing an agent corresponding to the drug-responsive promoter into contact with the cells in the animal body.

[40] The method according to any of [34] to [39], wherein said pluripotent stem cells are induced pluripotent stem cells derived from a human.

[41] The method according to [40], wherein said human-derived induced pluripotent stem cells have been produced from somatic cells isolated from a patient with Alzheimer's disease.

[42] The method according to [40], wherein said human-derived induced pluripotent stem cells have one or more mutations in presenilin 1 gene.

[43] A method of identifying a marker specific to a subject for whom an investigational agent for Alzheimer's disease has been confirmed to be effective (namely, a responder) or ineffective (namely, a non-responder), comprising the following steps in order (1) to (3):
(1) producing induced pluripotent stem cells from somatic cells isolated from a responder and a non-responder;
(2) generating neurons from the induced pluripotent stem cells obtained in step (1), by the method according to any of [34]-[38];
(3) measuring the amount of gene products in the neurons derived from the responder and the non-responder, which were obtained in step (2); and
(4) identifying a gene product which amount is higher in the neurons derived from the responder than in the neurons derived from the non-responder as the responder-specific marker, or a gene product which amount is lower in the neurons derived from the responder than in the neurons derived from the non-responder as the non-responder-specific marker.

[44] A method of selecting a subject for whom a therapeutic agent is effective, comprising the following steps of (1) to (3):
(1) producing induced pluripotent stem cells from somatic cells isolated from a subject;
(2) generating neurons from the induced pluripotent stem cells obtained in step (1), by the method according to any of [34]-[38];
(3) detecting the presence or absence of the a marker in the neurons obtained in step (2), wherein the marker has been identified as a responder-specific or a non-responder-specific marker by the method according to [43]; and
(4) selecting the subject as the subject for whom the therapeutic agent corresponding to said marker is effective, when the responder-specific marker is detected, or the non-responder-specific marker is not detected in the neurons derived from said subject.

[45] A pluripotent stem cell in which an exogenous nucleic acid encoding Ngn2 has been inserted in the chromosome by a transposon.

[46] The pluripotent stem cell according to [45], wherein said transposon is a piggyBac transposon.

[47] The pluripotent stem cell according to [45] or [46], wherein said nucleic acid is functionally connected to a drug-responsive promoter.

[48] The pluripotent stem cell according to [47], wherein said drug-responsive promoter is a tetracycline-responsive promoter.

[49] The pluripotent stem cell according to any of [45] to [48], wherein said pluripotent stem cell is an induced pluripotent stem cell derived from a human.

[50] The pluripotent stem cell according to [49], wherein said human-derived induced pluripotent stem cell has been produced from a somatic cell isolated from a patient with Alzheimer's disease.

[51] The pluripotent stem cell according to [49], wherein said human-derived induced pluripotent stem cell has one or more mutations in presenilin 1 gene.

[52] A method for screening a therapeutic agent for Alzheimer's disease, comprising the following steps in order (1) to (4):

(1) generating neurons from induced pluripotent stem cells by the method according to any of [34]-[38], wherein the induced pluripotent stem cells have been produced from somatic cells isolated from a patient with Alzheimer's disease;

(2) bringing a test substance into contact with the neurons obtained in step (1);

(3) culturing the neurons which have been contacted with the substance in step (2) and the neurons which have not been contacted with the substance (i.e., control cells), and measuring the amount of Aβ42 in the medium;

(4) selecting a test substance as the therapeutic agent for Alzheimer's disease, when the amount of Aβ42 in the medium of the neurons which have been contacted with said substance is lower than the amount of Aβ42 in the medium of control cells.

[53] The method according to [52], wherein step (3) further comprises a step of measuring the amount of Aβ40 in the medium, and step (4) comprises a step of selecting a test substance as the therapeutic agent for Alzheimer's disease, when the ratio of the amount of Aβ42 to that of Aβ40 (i.e., the amount of Aβ42/the amount of Aβ40) in the medium of the neurons which have been contacted with said substance is lower than that of control cells.

Advantageous Effects of Invention

According to the present invention, a motor neuron or a neuron having a property similar to that of a native motor neuron or a neuron, respectively, can be generated from a pluripotent stem cell promptly and synchronically. In particular, a motor neuron and a neuron generated from pluripotent stem cells derived from a patient with neurodegenerative disease according to the present method are extremely preferable as a screening system for a therapeutic agent for the disease, since said neurons can sufficiently reproduce a phenomenon characteristic to the disease.

Moreover, the present invention provides a pluripotent stem cell and a blood cell, which are capable of differentiating into a motor neuron or a neuron promptly and synchronically by a treatment with a drug and the like. Since said pluripotent stem cell and blood cell can be induced to differentiate into a motor neuron or a neuron in a living body, said cells can be preferably used as a composition for treating neurodegenerative disease or nerve injury (a transplantation therapy agent).

BRIEF DESCRIPTION OF DRAWINGS

FIG. 1A shows a schematic view of the tetracycline-inducible MN factor expression vector used in Example 1 (a part). In the figure, Tet-O represents tetracycline responsive promoter with TRE, Lhx3, Ngn2, Isl1, mCherry represents coding sequence of each gene, and Frt represents the target sequence of the Flippase recombinase. FIG. 1B shows the results of measurement of expression level of Lhx3, Ngn2, Isl1 proteins (Western blot) in the 293T cells that were transfected with the vector described in FIG. 1A and cultured in the presence (DOX+) or absence (DOX−) of DOX for 24 hours. FIG. 1C shows the images of immunostaining for undifferentiation markers (Nanog and SSEA1) of the mouse ES cells in which the vector described in FIG. 1A has been introduced. FIG. 1D shows the image of fluorescence microscopic of mCherry in the mouse ES cells in which the vector described in FIG. 1A has been introduced (right) or not introduced (left). The cells were cultured in the presence (DOX+) or absence (DOX−) of DOX for 18 hours prior to the analysis. FIG. 1E shows the results of real-time PCR measuring mRNA level of Lhx3, Ngn2 and Isl1 in the mouse ES cells in which the vector described in FIG. 1A has been introduced. The cells were cultured in the presence (DOX+) or absence (DOX−) of DOX for 18 hours prior to the measurement. FIG. 1F shows the timeline of differentiating mouse-derived ES cells into motor neurons (iMN). FIG. 1G shows the images of immunostaining (double immunostaining for HB9 and one selected from β-III tubulin, MAP2, and ChAT) of the mouse ES cells in which the vector described in FIG. 1A has been introduced. The cells were cultured in the presence (DOX+) or absence (DOX−) of DOX for 3 days prior to the immunostaining. FIG. 1H shows the results of real-time PCR measuring mRNA level of HB9 and ChAT in the mouse ES cells in which the vector described in FIG. 1A has been introduced. The cells were cultured in the presence (DOX+) or absence (DOX−) of DOX prior to the measurement.

FIG. 2A shows the results of investigation of the medium type suitable for inducing differentiation of the mouse ES cells in which the vector described in FIG. 1A has been introduced into iMN. FIG. 2B shows the experimental design for studying the period of DOX treatment. FIG. 2C shows the results of real-time PCR measuring mRNA level of each gene in the cells at Day7 in FIG. 2B. "Dox withdraw" represents the cells cultured in the DOX-containing medium for the first 3 days but in the DOX-free medium from Day3 to Day7, and "dox (+)" represents the cells cultured for 7 days in the DOX containing medium.

FIG. 3A shows the phase contrast image (left) and immunostaining image for αBTX/SV2 (right) of co-culture of C2C12 cells and motor neurons induced from the mouse ES cells in which the vector described in FIG. 1A has been introduced. The induction of differentiation of the mouse ES cells was carried out in the presence of C2C12 cells by adding DOX into the co-culture medium. FIG. 3B shows the results of calcium imaging in the co-culture of FIG. 3A. FIG. 3C shows the recordings measured by patch clamp method (current clamp). FIG. 3D shows the records of inward currents (voltage clamp) evoked by the addition of a neurotransmitter (glutamate and GABA).

FIG. 4A shows the results of analysis by the PCR method for the presence of human SOD1 gene (exogenouse gene) in the tissues prepared from transgenic mice having wild-type human SOD1 gene (SOD1WT) or mutant human SOD1 gene (SOD1G93A), MEF prepared from the mice, and iPS cells established from the MEF. FIG. 4B shows the results of sequencing of the mutation site of the exogenous human SOD1 genes in the iPS. FIG. 4C shows the results of measurement by quantitative PCR method of the expression level of ES cell marker genes (Eras, Esg1, Rex1, Oct3/4 and Sox2) in the mouse iPS cells established above. FIG. 4D shows the results of measurement by quantitative PCR method of the expression level of reprogramming factors (Oct3/4, Sox2, Klf4 and c-Myc) in the mouse iPS cells established above.

FIG. 5 shows the images of immunostaining for three germ layers marker (ectoderm (β-III tubulin), mesoderm (α-smooth muscle actin), and endoderm (α-fetoprotein) in the cells differentiated from the established mouse iPS cells by in vitro differentiation.

FIG. 6A shows a schematic view of the tetracycline-inducible MN factor expression vector used in Example 2 to 8 (a part). In the figure, TR represents target sequences of piggyBac transposase (i.e., inverted terminal repeat sequences). FIG. 6B shows the images of immunostaining for undifferentiation markers (Nanog and SSEA1) of the mouse iPS cells (which is abbreviated as WT-derived mouse iPS cells or G93A-derived mouse iPS cells in the present specification) in which the vector described in FIG. 6A has been introduced. FIG. 6C shows the images of immunostaining for β-III tubulin, or HB9 and ChAT, in the mouse iPS cells in which the vector described in FIG. 6A has been introduced. The iPS cells were cultured in the DOX medium for 3 days prior to the immunostaining. FIG. 6D shows the images of immunostaining for misfolded SOD1, or misfolded SOD1 and Neurofilament (NF-H) with DAPI-staining, in the mouse iPS cells in which the vector described in FIG. 6A has been introduced. The iPS cells were cultured in the DOX medium for 3 days prior to the immunostaining. FIG. 6E shows the measurement of survival of motor neurons (i.e., the number of HB9 and β-III tubulin-positive cells on the 6th day after DOX addition/the number of HB9 and β-III tubulin-positive cells on the 4th day after DOX addition) that were differentiated (in the absence of astrocytes) from the mouse iPS cells in which the vector described in FIG. 6A has been introduced. FIG. 6F shows the measurement of the ratio of LDH level in the medium on the 6th day to the level on the 4th day after DOX addition in the mouse iPS cells in which the vector described in FIG. 6A had been introduced. FIG. 6G shows the measurement of survival of motor neurons (i.e., the number of HB9 and β-III tubulin-positive cells on the 6th day after DOX addition/the number of HB9 and β-III tubulin-positive cells on the 4th day after DOX addition) that were differentiated (in the presence of astrocytes) from the mouse iPS cells (SOD1WT and SOD1G93A) in which the vector described in FIG. 6A has been introduced. FIG. 6H shows the measurement of the average value of neurite length of motor neurons differentiated from the mouse iPS cells (SOD1WT and SOD1G93A) in which the vector described in FIG. 6A has been introduced on the 4th day and the 6th day after DOX addition.

FIG. 7A shows the images of immunostaining for undifferentiation markers (Nanog and SSEA1) of the human normal control-derived iPS cells in which the vector described in FIG. 6A has been introduced. FIG. 7B shows the timeline of differentiating human-derived iPS cells in FIG. 7A into motor neurons (iMN). FIG. 7C shows the images of fluorescence microscopy (HB9) and immunostaining for β-III tubulin, or ChAT in the iPS cells described in FIG. 7A. FIG. 7D shows the results of measurement of expression level of HB9 and ChAT by PCR in the human iPS cells in which the vector described in FIG. 6A has been introduced and cultured in the presence (DOX+) or absence (DOX−) of DOX. FIG. 7E shows the phase contrast image (left) and immunostaining image for αBTX/SV2 (right) of co-culture of C2C12 cells and motor neurons induced from the human iPS cells in which the vector described in FIG. 6A has been introduced. FIG. 7F shows the recordings measured by patch clamp method (current clamp). FIG. 7G shows the records of inward currents (voltage clamp) evoked by the addition of a neurotransmitter (glutamate, kainite, and GABA).

FIG. 8A shows the image of the mouse ES cells in which the vector described in FIG. 1A has been introduced and cultured on OP9 cells for 5 days. FLK-1 is a marker of mesoderm, and SSEA-1 is a marker of undifferentiated cells. FIG. 8B shows the results of FACS analysis of the mouse ES cells in which the vector described in FIG. 1A has been introduced and cultured on OP9 cells for 5 days. FIG. 8C shows the images of staining of monocytes or macrophages differentiated from of the mouse ES cells in which the vector described in FIG. 1A had been introduced.

FIG. 9 shows the images of immunostaining of neurons induced from the blood cells that had differentiated from the mouse ES cells in which the vector described in FIG. 1A had been introduced. In the figure, Tuj1 positive indicates neurons, and HB9 positive indicates motor neurons.

FIG. 10A shows the results of sequencing of (the mutation site of) SOD1 gene in the iPS cells established from human ALS patients having L144FVX mutation (the upper figure: SOD1-L144FVX) or G93S mutation (the lower figure: SOD1-G93S) in SOD1 gene. FIG. 10B shows the timeline of differentiating human-derived iPS cells in FIG. 10A into motor neurons with the experimental design. Cell survival assay was carried out by measuring the change in cell number from Day7 to Day14. FIG. 10C shows the images of immunostaining of motor neurons at Day 7 after induced from each iPS cell.

FIG. 10D shows the measurement of survival of motor neurons from Day 7 to Day 14 after the induction of differentiation (i.e., the number of β-III tubulin-positive cells on the 14th day/the number of β-III tubulin-positive cells on the 7th day after the induction).

FIG. 11A shows the results of measurement of the number of cells expressing undifferentiation marker (SSES1) or neuron-specific marker (NCAM), and/or having neuron-like morphology, in the culture of the normal mouse-derived iPS cells in which the vector described in FIG. 6A has been introduced, up to the 72 hours after DOX addition. FIG. 11B shows the results of measurement of the number of cells expressing neuron-specific marker (NCAM) and having neuron-like morphology (i.e., iMN) in the culture of the normal control-derived human iPS cells in which the vector described in FIG. 6A has been introduced, up to the 7th day after DOX addition.

FIG. 12A shows the results of measurement of iMN number up to the 10th day after DOX addition, in the culture of iPS cells derived from 3 types of mice in which the vector described in FIG. 6A has been introduced (non-transgenic mouse, wild-type SOD1 transgenic mice, and mutant SOD1 transgenic mice). The vertical axis represents the number of iMN per culture well.

FIG. 13A shows the images of immunostaining for β-III tubulin of the iPS cells derived from ALS patient having L144FVX mutant SOD1 gene, in which the vector described in FIG. 6A has been introduced. Riluzole-treatment (0, 10, 50 μM) started at Day 7 and immunostaining was carried out at Day 14 after the addition of DOX. FIG. 13B shows the results of measurement of the number of iMN at Day 14 after DOX addition in the culture described in FIG. 13A. The vertical axis represents a percentage of the iMN of total cells in the well.

FIG. 14: shows an overview of a drug screening system using the MN factor-introduced iPS cells according to the present invention.

FIG. 15A shows the results of evaluation of accuracy of the screening system described in FIG. 14. FIG. 15B shows the results of studying approximately 1200 types of existing drug compounds using the screening system evaluated in FIG. 15A. The vertical axis represents a relative value of the number of iMN in the well applied with each compound with respect to the number of iMN in the negative control wells.

FIG. 16A shows the images of immunostaining for undifferentiation markers (Nanog and SSEA1) and neuron-specific markers (Tuj1, NCAM) of the N factor-induced human-derived iPS cells after DOX addition. FIG. 16B shows the phase contrast images of the cells on the day 11 after initiation of the induction of Ngn2 expression. Cell death was hardly observed and therefore, the culture could be used for analysis. FIG. 16C shows the results of measurement of the amount of Aβ40 and Aβ42 peptides in the conditioned medium. The upper case indicates the amount derived from the culture from Day 3 to Day 5, from Day 5 to Day 7, from Day7 to Day 9, and from Day 9 to Day 11 after the induction of Ngn2 expression, respectively. The middle and lower cases indicate the amount derived from the culture into which BSI IV or Sulfide Slindac was added, from Day7 to Day 9 (middle case), and from Day 9 to Day 11 (lower case) after the induction of Ngn2 expression, respectively.

FIG. 17 shows the images of fluorescence microscopy (HB9::GFP) and immunostaining of the injection site of the NOG mouse into which the HB9::GFP and MN factor-introduced mouse ES cells had been transplanted into the spinal cord. The NOG mouse had been orally administered DOX for 2 weeks prior to the analysis. GFP-positive cells represent the transplanted mouse ES cell-derived motor neurons (iMN), since the expression of GFP was cooperated with that of HB9.

FIG. 18 shows the images of immunostaining of the injection site in the NOG mouse into which the N factor-introduced human iPS cells had been transplanted into hippocampus. The NOG mouse had been orally administered DOX for 4 weeks prior to immunostaining. hNCAM-positive cells represent the transplanted human iPS cell-derived neurons (iN).

FIG. 19 shows a diagram explaining more accurate clinical trials utilizing the iPS cells provided by the present invention.

DESCRIPTION OF EMBODIMENTS

Hereinafter, the preferred embodiments of the present invention will be explained.

In the present specification, a motor neuron(s) or a neuron(s) produced by the method according to the present invention is sometimes referred to as iMN or iN, respectively, in order to distinguish a native motor neuron(s) or a neuron(s). Also, a set of Lhx3, Ngn2, and Isl1 genes is sometimes referred to as a motor neural-inducing factor (abbreviated to "MN factor"), and Ngn2 gene alone is sometimes referred to as a neural-inducing factor (abbreviated to "N factor").

<Method of Generating a Motor Neuron or a Neuron from a Pluripotent Stem Cell>

The present invention provides a method of inducing a prompt and synchronized differentiation of a pluripotent stem cell into a motor neuron, by introducing one or more nucleic acids encoding Lhx3, Ngn2, and Isl1 into a pluripotent stem cell and maintaining the expression of the three genes for 3 days or more. The expression of the three genes can be induced, either under culture or in an animal body. Moreover, the pluripotent stem cell into which the three genes has been introduced may be induced to differentiate into a blood cell under culture, and thereafter, may be induced to differentiate into a motor neuron by inducing the expression of the three genes, so that a motor neuron can be produced from the pluripotent stem cell via the blood cell.

The present invention further provides a method of inducing a prompt and synchronized differentiation of a pluripotent stem cell into a neuron, by introducing a nucleic acid encoding Ngn2 into a pluripotent stem cell using a transposon and maintaining the expression of said gene for 3 days or more. The expression of Ngn2 gene can be induced, either under culture or in an animal body.

Hereafter, a technique of constituting these methods will be described in detail.

<Pluripotent Stem Cells>

In the present invention, the pluripotent stem cell means a stem cell that has a pluripotency of differentiating into all types of cells present in a living body and also has a proliferating ability. Examples of the pluripotent stem cells include, but are not limited to, embryonic stem (ES) cells, nuclear transfer embryonic stem (ntES) cells derived from a cloned embryo obtained by nuclear transfer, spermatogonial stem cells ("GS cells"), embryonic germ cells ("EG cells"), induced pluripotent stem (iPS) cells, and pluripotent cells derived from cultured fibroblasts or bone marrow stem cells (Muse cells). Among these cells, pluripotent stem cells preferably used in the present invention include ES cells, ntES cells, and iPS cells. Hereinafter, each of these stem cells will be described.

(A) Embryonic Stem Cells

ES cell is a stem cell having a pluripotency and a proliferating ability associated with self-replication, which has been established from an inner cell mass of an early embryo (e.g., a blastocyst) of a mammal such as a human or a mouse.

The ES cell is a stem cell derived from an embryo from the inner cell mass of a blastocyst that is an embryo after the 8-cell stage and morula stage of a fertilized egg, and this cell has an ability to differentiate into all types of cells constituting an adult body, namely, differentiation pluripotency, and proliferating ability associated with self-replication. The ES cells were discovered in a mouse in 1981 (M. J. Evans and M. H. Kaufman (1981), Nature 292:154-156), and thereafter, the ES cell line was also established in primates such as a human and a monkey (J. A. Thomson et al. (1998), Science 282:1145-1147; J. A. Thomson et al. (1995), Proc. Natl. Acad. Sci. USA, 92:7844-7848;J. A. Thomson et al. (1996), Biol. Reprod., 55:254-259; J. A. Thomson and VS. Marshall (1998), Curr. Top. Dev. Biol., 38:133-165).

The ES cells can be established by extracting an inner cell mass from the blastocyst of the fertilized egg of a target animal and then culturing the inner cell mass on a fibroblast feeder. In addition, retention of the cells by subculture can be carried out using a culture, to which a substance such as a leukemia inhibitory factor (LIF) or a basic fibroblast growth factor (bFGF) has been added. Methods for establishing and retaining the ES cells of a human and a monkey are described, for example, in U.S. Pat. No. 5,843,780; Thomson J A, et al. (1995), Proc Natl. Acad. Sci. USA. 92:7844-7848; Thomson J A, et al. (1998), Science. 282: 1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444:481-485; etc.

As a culture used to produce ES cells, for example, a DMEM/F-12 culture, to which 0.1 mM 2-mercaptoethanol, 0.1 mM non-essential amino acid, 2 mM L-glutamic acid, 20% KSR and 4 ng/ml bFGF have been replenished, is used, and human ES cells can be retained at 37° C. in a wet atmosphere of 2% $CO_2$/98% air (O. Fumitaka et al. (2008), Nat. Biotechnol., 26:215-224). Moreover, the ES cells need to be subcultured every 3 or 4 days, and the subculture can be carried out, for example, using 0.25% trypsin and 0.1 mg/ml collagenase IV in PBS that contains 1 mM CaCl$_2$) and 20% KSR.

The ES cells can be generally selected by a Real-Time PCR method, using the expression of a gene marker such as alkaline phosphatase, Oct-3/4 or Nanog, as an indicator. In particular, when human ES cells are selected, the expression of a gene marker specific to undifferentiated cells, such as OCT-3/4, NANOG, or ECAD, can be used as an indicator (E. Kroon et al. (2008), Nat. Biotechnol., 26:443-452).

Human ES cell lines, for example WA01 (H1) and WA09 (H9) are available from WiCell Reserch Institute, and KhES-1, KhES-2 and KhES-3 are available from the Kyoto University Institute for Frontier Medical Sciences (Kyoto, Japan).

(B) Spermatogonial Stem Cells

Spermatogonial stem cell is a pluripotent stem cell derived from testis, which serves as an origin for formation of the sperm. The cell can be induced to differentiate into cells of various lines, as well as ES cells, and has properties such that if the cell is transplanted, for example, in a mouse blastocyst, a chimeric mouse can be produced (M. Kanatsu-Shinohara et al, Biol Reprod, 69: 612-616, 2003; K. Shinohara et al, Cell, 119: 1001-1012, 2004). The spermatogonial stem cells are able to self-replicate in a culture medium containing glial cell line-derived neurotrophic factor (GDNF), and such spermatogonial stem cells can also be obtained by repeating subculture under the same culture conditions as those of ES cells cells (Takebayashi Masanori et al. (2008), Experimental Medicine, Vol. 26, No. 5 (special edition), 41-46 pages, Yodosha (Tokyo, Japan), 2008).

(C) Embryonic Germ Cells

Embryonic germ cell is established from a primordial germ cell at embryonic stage and has a pluripotency similar to ES cells. The embryonic germ cell can be established by culturing primordial germ cells in the presence of substances such as LIF, bFGF, stem cell factor, etc. (Y. Matsui et al (1992), Cell, 70: 841-847; J L Resnick et al (1992), Nature, 359: 550-551).

(D) Induced Pluripotent Stem Cells

Induced pluripotent stem (iPS) cell is an artificial stem cell derived from a somatic cell, which can be produced by introducing a specific reprogramming factor in the form of a DNA or protein into a somatic cell, and show almost equivalent property (e.g., pluripotent differentiation and proliferation potency based on self-renewal) as ES cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO2007/069666). The reprogramming factor may be constituted with a gene specifically expressed by ES cell, a gene product or non-coding RNA thereof, a gene playing an important role for the maintenance of undifferentiation of ES cell, a gene product or non-coding RNA thereof, or a low molecular weight compound. Examples of the gene contained in the reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, Glis1 and the like. These reprogramming factors may be used alone or in combination. Examples of the combination of the reprogramming factors include combinations described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, *Mali* P, et al. (2010), Stem Cells. 28:713-720, and Maekawa M, et al. (2011), Nature. 474:225-9.

Examples of the above-mentioned reprogramming factor include, but are not limited to, factors used for enhancing the establishment efficiency, such as histone deacetylase (HDAC) inhibitors [e.g., low-molecular inhibitors such as valproic acid (VPA), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], MEK inhibitor (e.g., PD184352, PD98059, U0126, SL327 and PD0325901), Glycogen synthase kinase-3 inhibitor (e.g., Bio and CHIR99021), DNA methyl transferase inhibitors (e.g., 5-azacytidine), histone methyl transferase inhibitors [for example, low-molecular inhibitors such as BIX-01294, and nucleic acid-based expression inhibitors such as siRNAs and shRNAs against Suv39h1, Suv39h2, SetDB1 and G9a], L-channel calcium agonist (e.g., Bayk8644), butyric acid, TGFβ inhibitor or ALK5 inhibitor (e.g., LY364947, SB431542, 616453 and A-83-01), p53 inhibitor (e.g., siRNA and shRNA against p53), ARID3A inhibitor (e.g., siRNA and shRNA against ARID3A), miRNA such as miR-291-3p, miR-294, miR-295, mir-302 and the like, Wnt Signaling activating agent (e.g., soluble Wnt3a), neuropeptide Y, prostaglandins (e.g., prostaglandin E2 and prostaglandin J2), hTERT, SV40LT, UTF1, IRX6, GLIS1, PITX2, DMRTB1 and the like. In the present specification, these factors used for enhancing the establishment efficiency are not particularly 5 distinguished from the reprogramming factor.

When in the form of a protein, a reprogramming factor may be introduced into a somatic cell by a method, for example, lipofection, fusion with cell penetrating peptide (e.g., TAT derived from HIV and polyarginine), microinjection and the like.

When in the form of a DNA, a reprogramming factor may be introduced into a somatic cell by the method of, for example, vector of virus, plasmid, artificial chromosome and the like, lipofection, liposome, microinjection and the like. Examples of the virus vector include retrovirus vector, lentivirus vector (Cell, 126, pp. 663-676, 2006; Cell, 131, pp. 861-872, 2007; Science, 318, pp. 1917-1920, 2007), adenovirus vector (Science, 322, 945-949, 2008), adeno-associated virus vector, vector of Hemagglutinating Virus of Japan (WO 2010/008054) and the like. Examples of the artificial chromosome vector include human artificial chromosome (HAC), yeast artificial chromosome (YAC), bacterial artificial chromosome (BAC, PAC) and the like. As the plasmid, plasmids for mammalian cells can be used (Science, 322:949-953, 2008). The vector can contain regulatory sequences of promoter, enhancer, ribosome binding sequence, terminator, polyadenylation site and the like so that a nuclear reprogramming substance can be expressed and further, where necessary, a selection marker sequence of a drug resistance gene (e.g., kanamycin resistance gene, ampicillin resistance gene, puromycin resistance gene and the like), thymidine kinase gene, diphtheria toxin gene and the like, a reporter gene sequence of green fluorescent protein (GFP), β glucuronidase (GUS), FLAG and the like, and the like. Moreover, the above-mentioned vector may have a LoxP sequence before and after thereof to simultaneously cut out a gene encoding a reprogramming factor or a gene encoding a reprogramming factor bound to the promoter, after introduction into a somatic cell.

When in the form of RNA, for example, it may be introduced into a somatic cell by a means of lipofection, microinjection and the like, and RNA incorporating 5-methylcytidine and pseudouridine (TriLink Biotechnologies) may be used to suppress degradation (Warren L, (2010) Cell Stem Cell. 7:618-630).

Examples of the culture medium for inducing iPS cell include 10 to 15% FBS-containing DMEM, DMEM/F12 or DME culture medium (these culture media can further contain LIF, penicillin/streptomycin, puromycin, L-glutamine, nonessential amino acids, β-mercaptoethanol and the like as appropriate) or a commercially available culture medium [for example, culture medium for mouse ES cell culture (TX-WES culture medium, Thromb-X), culture medium for primate ES cell (culture medium for primate ES/iPS cell, Reprocell), serum-free medium (mTeSR, Stemcell Technologies)] and the like.

Examples of the culture method include contacting a somatic cell with a reprogramming factor on 10% FBS-containing DMEM or DMEM/F12 culture medium at 37° C. in the presence of 5% CO2 and culturing for about 4 to 7 days, thereafter reseeding the cells on feeder cells (e.g., mitomycin C-treated STO cells, SNL cells etc.), and culturing the cells in a bFGF-containing culture medium for primate ES cell from about 10 days after the contact of the somatic cell and the reprogramming factor, whereby ES-like colonies can be obtained after about 30 to about 45 days or longer from the contact.

Alternatively, the cells are cultured on feeder cells (e.g., mitomycin C-treated STO cells, SNL cells etc.) at 37° C. in the presence of 5% CO2 in a 10% FBS-containing DMEM culture medium (which can further contain LIF, penicillin/streptomycin, puromycin, L-glutamine, nonessential amino acids, β-mercaptoethanol and the like as appropriate), whereby ES-like colonies can be obtained after about 25 to about 30 days or longer. Desirably, a method using a somatic cell itself to be reprogrammed, or an extracellular substrate (e.g., Laminin-5 (WO2009/123349) and Matrigel (BD)), instead of the feeder cells (Takahashi K, et al. (2009), PLoS One. 4:e8067 or WO2010/137746).

Besides the above, a culture method using a serum-free medium can also be recited as an example (Sun N, et al. (2009), Proc Natl Acad Sci USA. 106:15720-15725). Furthermore, to enhance establishment efficiency, an iPS cell may be established under hypoxic conditions (oxygen concentration of not less than 0.1% and not more than 15%) (Yoshida Y, et al. (2009), Cell Stem Cell. 5:237-241 or WO2010/013845), can be mentioned.

The culture medium is exchanged with a fresh culture medium once a day between the above-mentioned cultures, from day 2 from the start of the culture. While the cell number of the somatic cells used for nuclear reprogramming is not limited, it is about $5 \times 10^3$ to about $5 \times 10^6$ cells per 100 cm2 culture dish.

The iPS cell can be selected based on the shape of the formed colony. When a drug resistance gene which is expressed in association with a gene (e.g., Oct3/4, Nanog) expressed when a somatic cell is reprogrammed is introduced as a marker gene, an established iPS cell can be selected by culturing in a culture medium (selection culture medium) containing a corresponding drug. When the marker gene is a fluorescent protein gene, iPS cell can be selected by observation with a fluorescence microscope, when it is a luminescent enzyme gene, iPS cell can be selected by adding a luminescent substrate, and when it is a chromogenic enzyme gene, iPS cell can be selected by adding a chromogenic substrate.

The term "somatic cells" used in the present specification means any animal cells (preferably, cells of mammals inclusive of human) excluding germ line cells and totipotent cells such as ovum, oocyte, ES cells and the like. Somatic cells unlimitatively encompass any of somatic cells of fetuses, somatic cells of neonates, and mature healthy or pathogenic somatic cells, and any of primary cultured cells, passage cells, and established lines of cells. Specific examples of the somatic cells include (1) tissue stem cells (somatic stem cells) such as neural stem cell, hematopoietic stem cell, mesenchymal stem cell, dental pulp stem cell and the like, (2) tissue progenitor cells, (3) differentiated cells such as lymphocyte, epithelial cell, endothelial cell, myocyte, fibroblast (skin cells etc.), hair cell, hepatocyte, gastric mucosal cell, enterocyte, splenocyte, pancreatic cell (pancreatic exocrine cell etc.), brain cell, lung cell, renal cell and adipocyte and the like, and the like.

Furthermore, from the viewpoint of preparation of model cells for a pathological condition, diseased somatic cells may also be used. An example of the concerned disease is neurodegenerative disease. When model cells for a pathological condition are prepared by applying the method for producing motor neurons described above, iPS cells may be produced using somatic cells derived from a patient with motor neuron disease. The term "motor neuron disease" is used herein to mean a disease caused by degeneration of motor neurons, and examples of the motor neuron disease include amyotrophic lateral sclerosis (ALS), spinal muscular atrophy (SMA), and spinal and bulbar muscular atrophy. Examples of somatic cells derived from a patient with amyotrophic lateral sclerosis include somatic cells mutated in SOD1 gene. More specific examples include SOD1 gene having a mutation such as G93A, G93S and L144FVX, but the examples are not particularly limited thereto. Likewise, when model cells for a pathological condition are prepared by applying the method for producing neurons described above, iPS cells may also be produced using somatic cells derived from a patient with neurodegenerative disease. The term "neurodegenerative disease" is used herein to mean a disease caused by degeneration or deficit of neurons, and examples of the neurodegenerative disease include Alzheimer-type dementia, Parkinson's disease, Lewy body dementia, Huntington's disease, and spinocerebellar degeneration. Examples of the somatic cells derived from a patient with Alzheimer-type dementia include somatic cells having a mutation in presenilin 1 gene or presenilin 2 gene. Regarding the mutation in presenilin 1, to date, 30 or more mutations have been reported (Price D L, Sisodia S S., Annu Rev Neurosci. 1998; 21: 479-505.). An example of the mutation in Presenilin 1 is a substitution of alanine or glutamic acid for D257 or D385, but the example is not particularly limited thereto.

(E) Cloned Embryo-Derived E S Cells Obtained by Nuclear Transplantation

The nt ES cells are ES cells derived from a cloned embryo, which are prepared by a nuclear transplantation technique, and have almost the same properties as those of fertilized egg-derived ES cells (T. Wakayama et al. (2001), Science, 292:740-743; S. Wakayama et al. (2005), Biol. Reprod., 72:932-936; J. Byrne et al. (2007), Nature, 450: 497-502). That is to say, nt ES (nuclear transfer ES) cells are ES cells established from the inner cell mass of a blastocyst derived from a cloned embryo obtained by substituting the nucleus of an unfertilized egg with the nucleus of a somatic cell. For preparation of such nt ES cells, a combination of a nuclear transplantation technique (J. B. Cibelli et al. (1998), Nature Biotechnol., 16:642-646) with the ES cell preparation technique (as described above) is (Wakayama Sayaka et al. (2008), Experimental Medicine, Vol. 26, No. 5 (special edition), 47-52 pages). In nuclear transplantation, the nucleus of a somatic cell is injected into the enucleated unfertilized egg of a mammal, and the egg is then cultured for several hours, so that it can be initialized.

(F) Multilineage-Differentiating Stress Enduring Cells (Muse Cells)

Muse cells are pluripotent stem cells prepared by the method described in WO2011/007900. In particular, a trypsinization of fibroblasts or bone marrow stromal cells for a long time, preferably for 8 hours or 16 hours, followed by suspension culture, can result in a production of SSEA-3 and CD105-positive cells having a pluripotency, i.e., Muse cells.

In the present invention, from the viewpoint of producing a cell model for disease, pluripotent stem cells in which a causative gene(s) for disease has been introduced can be utilized. As such causative genes, for the case of amyotrophic lateral sclerosis model cell, SOD1, C9ORF72, TDP43, FUS, PRN1, EPH4N, ANG, UBQLN and HNPNPA are exemplified, and pluripotent stem cells having these mutant genes are preferentially used. For example, an iPS cell generated by introducing a mutant SOD1 gene (A4V, G37R, G41D, H46R, G85R, D90A, G93A, G93S, I112T, I113T, L114F or S134N mutation is exemplified), and an iPS cell generated from a somatic cell isolated from a patient with amyotrophic lateral sclerosis can be mentioned. For the case of Alzheimer's type dementia model, somatic cell having one or more mutations in presenilin 1 or presenilin 2 gene are exemplified, and pluripotent stem cells having such mutant gene are desirable. As an example of a pluripotent stem cell having a mutant gene, an iPS cell generated from a somatic cell isolated from a patient with Alzheimer's type dementia can be mentioned.

In the present invention, the amyotrophic lateral sclerosis model cell or Alzheimer's dementia model cells includes motor neurons or neurons that is generated from pluripotent stem cells by the method described above. In the present invention, a preferred cell model for disease is a murine or human cell.

<Motor Neurons>

In the present invention, a motor neuron is defined as a cell that expresses one or more marker genes for motor neurons, such as HB9 and ChAT (choline acetyltransferase), or a cell that expresses one or more marker genes for neurons, such as βIII tubulin, NCAM, and MAP2, and has one or more neurite and a sufficiently thickened cell body. This is because we have been confirmed that a cell that expresses one or more marker genes for neurons and has a neurite and a sufficiently thickened cell body expresses HB9 or ChAT. Accordingly, the criteria for determining a motor neuron generated by the method according to the present invention (namely, iMN) complies with this definition. In the present invention, a generation/production of a motor neuron means an acquisition of a cell population containing a cell satisfying the definition, and it preferably means that a cell population containing 5%, 15%, or 20% or more of the cell is obtained.

<Neurons>

In the present invention, a neuron is defined as a cell that expresses one or more marker genes for neurons, such as β-III tubulin, NCAM, and MAP2, and has one or more neurite. Accordingly, the criteria for determining a neuron generated by the method according to the present invention (namely, iN) complies with this definition. In the present invention, a generation/production of a neuron means an acquisition of a cell population containing a cell satisfying the definition, and it preferably means that a cell population containing 50%, 60%, 70%, 80%, or 90% or more of the cell is obtained.

Incidentally, since Tuj1 is an anti-β-III tubulin antibody, a cell expressing the β-III tubulin is sometimes referred to as Tuj1-positive cell.

<Nucleic acids encoding Lhx3, Ngn2, and Isl1>

In the present invention, Lhx3 means an Lhx3 (LIM homeobox 3) gene and an Lhx3 protein. In addition, a nucleic acid encoding Lhx3 may be a gene encoded by a polynucleotide having NCBI Accession No. NM_001039653 (mouse) or NM_014564 or NM_178138 (human), and a transcript variant, a splicing variant and a homolog thereof, or a nucleic acid having a complementary relationship to these nucleic acids to such an extent that it is able to hybridize under stringent conditions with the complementary strand sequences of the nucleic acids.

Moreover, in the present invention, Ngn2 means an Ngn2 (Neurogenin 2) gene and an Ngn2 protein. In addition, a nucleic acid encoding Ngn2 may be a polynucleotide having NCBI Accession No. NM_009718 (mouse) or NM_024019 (human), or a transcript variant, a splicing variant and a homolog thereof, or a nucleic acid having a complementary relationship to these nucleic acids to such an extent that it is able to hybridize under stringent conditions with the complementary strand sequences of the nucleic acids.

Furthermore, in the present invention, Isl1 means an Isl1 (Islet 1) gene and an Isl1 protein. In addition, a nucleic acid encoding Isl1 may be a polynucleotide having NCBI Accession No. NM_021459 (mouse) or NM_002202 (human), or a transcript variant, a splicing variant and a homolog thereof, or a nucleic acid having a complementary relationship to these nucleic acids to such an extent that it is able to hybridize under stringent conditions with the complementary strand sequences of the nucleic acids.

In the above description, stringent conditions can be determined based on the melting temperature (Tm) of a complex or a probe-binding nucleic acid, as taught in Berger and Kimmel(1987, Guide to Molecular Cloning Techniques Methods in Enzymology, Vol. 152, Academic Press, San Diego Calif.). For example, washing conditions after completion of the hybridization can generally be conditions such as "1×SSC, 0.1% SDS, and 37° C." A complementary strand preferably maintains a hybridized state with a plus strand as a target, even if it has been washed under the above described conditions. More stringent hybridization conditions can be conditions in which the plus strand and the complementary strand can maintain a hybridized state, even after completion of the washing under washing conditions such as "0.5×SSC, 0.1% SDS, and 42° C.," and further stringent hybridization conditions can be conditions in which the plus strand and the complementary strand can maintain a hybridized state, even after completion of the washing under washing conditions such as "0.1×SSC, 0.1% SDS, and 65° C.," although the conditions are not particularly limited thereto. Specifically, examples of such a complementary strand include a strand consisting of a nucleotide sequence having a completely complementary relationship with the nucleotide sequence of the target plus strand, and a strand consisting of a nucleotide sequence having an identity of at least 90%, preferably 95% or more, more preferably 97% or more, even more preferably 98% or more, and particularly preferably 99% or more with the above described strand.

In the present invention, the nucleic acid encoding Lhx3, the nucleic acid encoding Ngn2, and the nucleic acid encoding Isl1 may be DNA, or RNA, or chimeric DNA/RNA. Moreover, the nucleic acid may be either a double strand or a single strand. When the nucleic acid is a double strand, it may be any one of double-stranded DNA, double-stranded RNA, and a DNA-RNA hybrid. Preferably, it is double-stranded DNA or single-stranded RNA. For instance, when the nucleic acids encoding Lhx3, Ngn2, and Isl1 are double-stranded DNA (there may be a case in which they are referred to as an Lhx3 gene, an Ngn2 gene, and an Isl1 gene in the present description), the nucleic acids can be introduced into a pluripotent stem cell in a form in which they are inserted in a suitable expression vector. On the other hand, when the nucleic acids encoding Lhx3, Ngn2, and Isl1 are single-stranded RNA, the RNA may be RNA comprising 5-methylcytidine and pseudouridine (TriLink Biotechnologies) or may also be a modified RNA that has been treated with phosphatase, in order to suppress decomposition of the RNA. It is to be noted that RNA encoding Lhx3 and an Lhx3 protein may be comprehensively referred to as an Lhx3 gene product in the present description (the same applies to Ngn2 and Isl1).

In the method for producing motor neurons or neurons of the present invention, nucleic acids encoding other transcription factors associated with neurogenesis may be introduced, together with an MN factor or an N factor, into pluripotent stem cells, as long as they do not inhibit an induction of motor neurons by the MN factor or an induction of neurons by the N factor. Examples of such a transcription factor include a nucleic acid encoding Ascl1, a nucleic acid encoding Brn2, a nucleic acid encoding Mytl1, and a nucleic acid encoding HB9.

<Method for Introducing Nucleic Acid into a Pluripotent Stem Cell>

The method for introducing a nucleic acid encoding Lhx3, a nucleic acid encoding Ngn2, and a nucleic acid encoding Isl1 into a pluripotent stem cell is not particularly limited, and for example, the following method can be applied.

When the nucleic acid is in the form of DNA, it is introduced into a vector such as a virus, a plasmid or an artificial chromosome, and it can be then introduced into a pluripotent stem cell by a method such as lipofection, liposome, or microinjection.

Examples of the virus vector include a retrovirus vector, a lentivirus vector, an adenovirus vector, an adeno-associated virus vector, and a Sendai virus vector. As a plasmid vector, a plasmid for mammalian cells can be used. Examples of the artificial chromosome vector include a human artificial chromosome (HAC), a yeast artificial chromosome (YAC), and a bacterial artificial chromosome (BAC, PAC). Among these vectors, a plasmid vector and an artificial chromosome vector are preferable, and a plasmid vector is most preferable.

These vectors may comprise regulatory sequences such as a promoter, an enhancer, a ribosome binding sequence, a terminator and a polyadenylation site, so that the Lhx3, Ngn2, or Isl1 gene can be expressed. Moreover, as necessary, these vectors may also comprise selection marker sequences such as drug resistance genes (e.g., a kanamycin resistance gene, an ampicillin resistance gene, a puromycin resistance gene, etc.), a thymidine kinase gene and a diphtheria toxin gene, and reporter gene sequences such as a fluorescent protein, $\beta$-glucuronidase (GUS) and FLAG.

In another aspect, in order to insert the nucleic acid encoding the gene into a chromosome, or in order to cleave the nucleic acid inserted in the chromosome, as necessary, the vector may have a transposon sequence before and after this expression cassette (a gene expression unit involving a promoter, a gene sequence and a terminator). The type of such a transposon sequence is not particularly limited, and an example of the transposon sequence is piggyBac. In order to introduce the expression cassette into a chromosome using transposon, it is desired to introduce transposase, together with a vector having the expression cassette, into the cell. In the present invention, for introduction of transposase, the above described vector may comprise a nucleic acid encoding the transposase, or it may also be possible that another vector is allowed to comprise a nucleic acid encoding the transposase and this vector is then introduced into the cell, simultaneously with the vector having the expression cassette. Otherwise, a gene product encoding the transposase may directly be introduced into the cell. In the present invention, preferred transposase is transposase corresponding to the above described transposon sequence, and it is preferably piggyBac transposase.

In the present invention, in order to allow Lhx3, Ngn2, and Isl1 to simultaneously express, an embodiment in which the three genes are allowed to express in a polycistronic manner may be adopted. As an example, IRES or a 2A-coding sequence is inserted between sequences encoding Lhx3, Ngn2, and Isl1, so that the three genes can be expressed in a polycistronic manner (Nat. Biotech., 5, 589-594, 2004). The used 2A-coding sequence may be derived from all types of viruses (J. General Virology, 89, 1036-1042, 2008), and it is preferably a 2A-coding sequence derived from foot and mouth disease virus (FMDV).

When the neural-inducing factor is in the form of RNA, it may be introduced into a pluripotent stem cell, for example, by a method such as electroporation, lipofection or microinjection.

When the neural-inducing factor is in the form of a protein, it may be introduced into a pluripotent stem cell, for example, by a method such as lipofection, fusion with a cell membrane permeable peptide (e.g., HIV-derived TAT and polyarginine), or microinjection.

<Induction of Expression of Lhx3, Ngn2, and Isl1>

The nucleic acid encoding Lhx3, the nucleic acid encoding Ngn2, and the nucleic acid encoding Isl1 may be operably linked to an inducible promoter, so that the expression of Lhx3, Ngn2, and Isl1 can be induced at a desired time. Such an inducible promoter can be a drug responsive promoter, and a preferred example of such a drug responsive promoter is a tetracycline-responsive promoter (a CMV minimal promoter having a tetracycline-responsive element (TRE) consisting of seven consecutive tetO sequences). The promoter is activated by the supply of tetracycline or a derivative thereof under the conditions in which a reverse tetracycline-controlled transactivator (rtTA: a fusion protein composed of reverse tetR (rTetR) and VP16AD) has been expressed. Accordingly, when a tetracycline-responsive promoter is used to induce the expression of the gene, it is more preferable to use a vector that is also capable of expressing such an activator. As a derivative of the tetracycline, doxycycline (hereinafter abbreviated as DOX in the present application) can be preferably used.

Moreover, examples of an expression induction system, in which a drug responsive promoter other than the above described drug responsive promoter is used, include an expression induction system in which an estrogen-responsive promoter is used (e.g., WO2006/129735), a Rheo-Switch mammal-inducible expression system (New England Biolabs) in which a promoter induced by RSL1 is used, a Q-mate system (Krackeler Scientific) or a Cumate-inducible expression system (National Research Council (NRC)) in which a promoter induced by cumate is used, and a GenoStat-inducible expression system (Upstate cell signaling solutions) in which a promoter having an ecdysone-responsive sequence is used.

When an expression vector comprising an expression induction system that is based on the above described drug responsive promoter (i.e., a drug response-inducing vector) is used, the expression of Lhx3, Ngn2, and Isl1 can be maintained by continuously adding a drug capable of inducing the activation of the promoter (e.g., tetracycline or DOX in the case of a vector comprising the tetracycline-responsive promoter) to a medium for a desired period of time. Thereafter, by removing the drug from the medium (e.g., by replacing the medium with a medium that does not contain the drug), the expression of the gene can be terminated.

Moreover, the expression of Lhx3, Ngn2, and Isl1 may also be induced by converting a connection between a nucleotide encoding the genes and a constitutive promotor from an inoperable manner in which the promotor cannot operate the expression of the genes into an operable manner in which the promotor can operate the expression at a desired time. For example, a method comprises a step of disposing certain nucleotide (e.g., a nucleotide encoding a drug resistance gene or a sequence inducing transcription termination) flanked with LoxP sequences between the constitutive promoter and the nucleotide encoding the genes, and a subsequent step of allowing Cre to act thereon at a desired time to remove the nucleotide flanked with the LoxP sequences, so as to convert the connection manner to an operable connection manner, can be mentioned. Furthermore, FRT sequences or transposon sequences may be used instead of the LoxP sequences, and FLP (flipase) or the transposon may be used instead of the Cre. An example of a transposon that can be preferably used for this purpose is a piggyBac transposon.

Examples of the constitutive promoter that can be used for the purpose include an SV40 promoter, an LTR promoter, a CMV (cytomegalovirus) promoter, an RSV (Rous sarcoma virus) promoter, MoMuLV (Moloney mouse leukemia virus) LTR, an HSV-TK (herpes simplex virus thymidine kinase) promoter, an EF-alpha promoter, and a CAG promoter.

As described above, when the expression has been induced by converting the connection mode using Cre, FLP, or transposon, it is also possible to terminate the expression of the gene by allowing the Cre, FLP, or transposon to act on the gene again after a desired period of time, so as to re-introduce the nucleotide flanked with the above described sequences (LoxP sequences, FRT sequences, or transposon sequences).

In another aspect, it is also possible to control the expression period of the gene by using a vector that can easily disappear from the inside of the cell, such as an adenovirus vector, an adeno-associated virus vector, a Sendai virus vector, a plasmid, or an episomal vector.

Upon production of a motor neuron, the expression of the introduced Lhx3, Ngn2, and Isl1 is preferably maintained for 3 days or more. The effects of the present invention can be obtained for any one of 4 days, 5 days, 6 days, and 7 days, and the expression period is particularly preferably 7 days. Even if the expression is maintained for a long period of time, there are no disadvantages for production of a motor neuron. The expression period is preferably 3 days or more and 14 days or less, and particularly preferably 7 days or more and 14 days or less.

Upon production of neurons as well, in the expression of the introduced Ngn2 the effects of the present invention can be obtained for any one of 3 days, 4 days, 5 days, 6 days, and 7 days. Even if the expression is maintained for a long period of time, there are no disadvantages for production of neurons. The expression period is preferably 3 days or more and 14 days or less, and most preferably 7 days or more and 14 days or less.

<Culture Conditions>

In the present invention, as a medium to be used for inducing differentiation of the pluripotent stem cells in which one or more nucleic acid encoding Lhx3, Ngn2, and Isl1 has been introduced, into motor neurons in the culture, a basal medium supplemented with a retinoic acid, SHH signal stimulants, and neurotrophic factors can be used. Examples of the basal medium include Glasgow's Minimal Essential Medium (GMEM), IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (Life Technologies), and the mixtures thereof, etc. The basal medium may contain serum or it may be serum-free. If necessary, the medium may contain one or more serum replacement such as, for example, Knockout Serum Replacement (KSR) (serum substitute for FBS in ES cell culture), N2 supplement (Invitrogen), B27 supplement (Invitrogen), albumin, transferrin, apotransferrin, fatty acids, insulin, collagen precursor, trace elements, 2-mercaptoethanol, and 3'-thiol glycerol. The medium may also contain one or more substances such as, for example, lipids, amino acids, L-glutamine, Glutamax (Invitrogen), nonessential amino acids, vitamins, growth factors, small molecule compounds, antibiotics, antioxidants, pyruvic acid, buffering agents, inorganic salts, selenate, progesterone, and putrescine, if necessary.

Among those media, in the present invention, a mixed medium of DMEM and F12 supplemented with insulin, apotransferrin, selenate, progesterone, and putrescine is preferred, and N3 medium (DMEM/F12 supplemented with 100 μg/ml apotransferrin, 5 μg/ml insulin, 30 nM selenite, 20 nM progesterone, and 100 nM putrescine) is particularly preferred. The N3 medium supplemented with 1 μM retinoic acid (RA), 1 μM sonic hedgehog (Shh), 10 ng/ml BDNF, 10 ng/ml GDNF, and 10 ng/ml NT3 can be preferably used as a differentiation-inducing culture medium for a differentiation into motor neurons.

Incidentally, in the case of using N2 medium instead of the N3 medium, the level of synchronization in the iMN differentiation or the cell death of iMN derived from ALS model mouse may decrease.

In the present invention, a SHH (Sonic hedgehog) signal stimulating agent is defined as a substance that causes a disinhibition of Smoothened (Smo) resulting from SHH-binding to its receptor, Patched (Ptch1), and subsequent an activation of Gli2. For example, SHH, Hh-Ag1.5 (Li, X., et al., Nature Biotechnology, 23:215-221, 2005), Smoothened Agonist, SAG (N-Methyl-N-(3-pyridinylbenzyl)-N'-(3-chlorobenzo [b] thiophene-2-carbonyl)-1,4-diaminocyclohexane), 20a-hydroxycholesterol, Purmorphamine, and the derivatives thereof, etc. are mentioned (Stanton B Z, Peng L F, Mol Biosyst 6:44-54, 2010).

SHH-signaling stimulant to be used in the present invention may be Purmorphamine, preferably.

The concentration of Purmorphamine in the culture medium is not particularly limited as long as it can activates Gli2, and, for example, can be appropriately selected in the following ranges, 1 nM or more, 10 nM or more, 50 nM or more, 100 nM or more, 500 nM or more, and 750 nM or more, or at least 1 µM, 50 µM or less, 40 µM or less, 30 µM or less, 25 µM or less, 20 µM or less, and 15 µM or less. It is generally used at 1 µM, 2 µM, 3 µM, 4 µM, 5 µM, 6 µM, 7 µM, 8 µM, 9 µM, or 10 µM, but not limited thereto. Preferably, it is 2 µM.

In the present invention, a neurotrophic factor is a ligand of a membrane receptor which plays a crucial role in maintaining survival and function of motor neurons. For example, Nerve Growth Factor (NGF), Brain-derived Neurotrophic Factor (BDNF), Neurotrophin 3 (NT-3), Neurotrophin 4/5 (NT-4/5), Neurotrophin 6 (NT-6), basic FGF, acidic FGF, FGF-5, Epidermal Growth Factor (EGF), Hepatocyte Growth Factor (HGF), Insulin, Insulin Like Growth Factor 1 (IGF 1), Insulin Like Growth Factor 2 (IGF 2), Glia cell line-derived Neurotrophic Factor (GDNF), TGF-b2, TGF-b3, Interleukin 6 (IL-6), like Ciliary Neurotrophic Factor (CNTF), and LIF, etc. are mentioned. A preferred neurotrophic factor in the present invention is a factor selected from the group consisting of GDNF, and BDNF.

In the present invention, as a medium to be used for inducing differentiation of the pluripotent stem cells in which a nucleic acid encoding Ngn2 has been introduced, into motor neurons in the culture, a basal medium alone, or a basal medium supplemented with neurotrophic factors can be used. Examples of the basal medium include Glasgow's Minimal Essential Medium (GMEM), IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (Life Technologies), and the mixtures thereof, etc. The basal medium may contain serum or it may be serum-free. If necessary, the medium may contain one or more serum replacement such as, for example, Knockout Serum Replacement (KSR) (serum substitute for FBS in ES cell culture), N2 supplement (Invitrogen), B27 supplement (Invitrogen), albumin, transferrin, apotransferrin, fatty acids, insulin, collagen precursor, trace elements, 2-mercaptoethanol, and 3'-thiol glycerol. The medium may also contain one or more substances such as, for example, lipids, amino acids, L-glutamine, Glutamax (Invitrogen), nonessential amino acids, vitamins, growth factors, small molecule compounds, antibiotics, antioxidants, pyruvic acid, buffering agents, inorganic salts, selenate, progesterone, and putrescine, if necessary.

Among those media, in the present invention, Neurobasal Medium supplemented with B27 supplement, or a mixed medium of DMEM and F12 supplemented with insulin, apotransferrin, selenate, progesterone, and putrescine is preferred.

Incidentally, in the case of using N2 medium instead of the N3 medium, the level of synchronization in the iMN differentiation or the cell death of iMN derived from ALS model mouse may decrease.

In the method according to the present invention, it is possible to induce the differentiation into neurons without co-culturing with mouse cells, in particular, mouse glial cells. Therefore, for the purpose of avoiding any contamination, it is preferred not to co-culture with mouse cells.

The culturing temperature for inducing differentiation into motor neurons or neurons is not particularly limited, and about 30 to 40° C., preferably about 37° C., in an air atmosphere containing $CO_2$. The $CO_2$ concentration is preferably about 5%.

<Cell Culture Comprising Neuromuscular Junction>

In the present invention, myotube cells can be added in the step of producing motor neurons from pluripotent stem cells, to obtain a cell culture having a neuromuscular junction, in which the myotube cells are connected with the motor neurons. The neuromuscular junction means a structure in which acetylcholine is released from the projection end of a motor neuron and a receptor expressed in myotube cells can receive it. The presence of such a neuromuscular junction can be confirmed, for example, by performing immunostaining or fluorescence microscope observation, and then by observing co-localization of a synaptic vesicle protein (e.g., SV2) expressed by a motor neuron and an acetylcholine receptor expressed by a myotube cell. The cell culture comprising the neuromuscular junction is extremely useful as a pathological model system of a pathological condition caused by the hypoplasia of a neuromuscular junction (e.g., myasthenia gravis and Lambert-Eaton myasthenia).

<Pluripotent Stem Cell, into Chromosome of which Exogenous Nucleic Acid is Inserted>

According to the present invention, a pluripotent stem cell, into the chromosome of which a nucleic acid encoding Lhx3, a nucleic acid encoding Ngn2, and an exogenous nucleic acid encoding Isl1 have been inserted, is provided. The nucleic acids are preferably under the control of an inducible promoter, and more preferably under the control of a drug responsive promoter. The pluripotent stem cell is a cell capable of differentiating into a motor neuron promptly and synchronously in contact with a drug to which the promoter is responsive.

Moreover, according to the present invention, a pluripotent stem cell, into the chromosome of which an exogenous nucleic acid encoding Ngn2 has been inserted, is provided. The nucleic acid is preferably under the control of an inducible promoter, and more preferably under the control of a drug responsive promoter. The pluripotent stem cell is a cell capable of differentiating into a neuron promptly and synchronously in contact with a drug to which the promoter is responsive.

The pluripotent stem cell, into the chromosome of which the above nucleic acid has been inserted, can proliferate without losing its undifferentiation ability and high proliferating ability. Furthermore, these cells can be stably maintained as a cell line, since said abilities are not impaired even if preserved in a frozen state.

When the pluripotent stem cell, into the chromosome of which the exogenous nucleic acid has been inserted, is derived from a patient with neurodegenerative disease, it can be preferably used as a screening system for therapeutic agents for the disease. On the other hand, when the pluripotent stem cell, into the chromosome of which the exogenous nucleic acid has been inserted, is derived from a healthy subject, it can be preferably used as a therapeutic composition for motor neuron disease or nerve injury, or for producing a model animal that retains human-derived motor neurons/neurons. Hereinafter, each intended use will be described in detail.

<Method for Screening a Therapeutic Agent for Amyotrophic Lateral Sclerosis>

The present invention provides a method for screening a therapeutic agent for amyotrophic lateral sclerosis, including the following steps (1) to (5):

(1) generating motor neurons from induced pluripotent stem cells by the method described above, wherein the induced pluripotent stem cells have been produced from somatic cells isolated from a patient with amyotrophic lateral sclerosis;

(2) bringing a test substance into contact with the motor neurons obtained in step (1);

(3) culturing the motor neurons which have been contacted with the substance in step (2) and the motor neurons which have not been contacted with the substance (i.e., control cells);

(4) measuring the cell number and/or the neurite length of the motor neurons obtained through step (3);

(5) selecting a test substance as the therapeutic agent for amyotrophic lateral sclerosis, when the value of the cell number and/or the neurite length of the motor neurons which have been contacted with said substance is higher than the value of the control cells.

In the present invention, a pluripotent stem cell derived from a patient with familial or sporadic amyotrophic lateral sclerosis can be used as an ALS patient-derived pluripotent stem cell. A pluripotent stem cell derived from a familial ALS patient is preferable, and a pluripotent stem cell derived from a familial ALS patient having one or more mutations in SOD1 gene is more preferable.

In the present invention, a test substance (i.e., the candidate agent) may be cell extracts, cell culture supernatants, microbial fermentation products, extracts from marine organism, plant extracts, purified or crude proteins, peptides, non-peptide compounds, synthetic low molecular compounds, and natural compounds, etc., for example.

In the present invention, the test substance may be obtained by using any of a number of approaches in combinatorial library methods known in the art, such as (1) the biological library method, (2) the synthetic library method using deconvolution, (3) the "one-bead one-compound" library method and (4) the synthetic library method using affinity chromatography selection. Application of the biological library method using affinity chromatography selection is limited to peptide libraries, but the other 4 types of approaches can be applied to low-molecular compound libraries of peptides, non-peptide oligomers or compounds (Lam, Anticancer Drug Des. 12:145-67, 1997). Examples of synthetic methods of molecular libraries can be found in the art (DeWitt et al. (1993) Proc. Natl. Acad. Sci. USA 90; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). The compound libraries may be prepared as solutions (see Houghten, Bio/Techniques 13: 412-21, 1992) or beads (Lam, Nature 354:82-4, 1991), chips (Fodor, Nature 364: 555-6, 1993), bacteria (U.S. Pat. No. 5,223,409 B), spores (U.S. Pat. Nos. 5,571,698 B, 5,403,484 B and U.S. Pat. No. 5,223,409 B), plasmids (Cull et al. (1992) Proc. Natl. Acad. Sci. USA 89: 1865-9) or phages (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US 2002103360 B).

In the screening method of a therapeutic agent for amyotrophic lateral sclerosis according to the present invention, motor neurons may be used in mixed with other types of cells.

In the present invention, a measurement of the number of motor neurons may be carried out by immunostaining the cells by a method well known to those skilled in the art, followed by counting the number of cells expressing one or more marker genes for neurons or motor neurons, such as HB9, β-III tubulin, and ChAT. The counting may be carried out using an automated cell counting device (e.g., IN Cell Analyzer). Alternatively, the number of cells may be calculated as the reciprocal of the number of dead cells. Measurement of the number of dead cells can be carried out, for example, by a method of measuring the activity of LDH, MTT method, WST-1 method, a method of measuring the absorbance using WST-8 method or, a method of counting cell number using a flow cytometer after staining the cells with TO (thiazole orange), PI (propidium iodide), 7AAD, calcein AM, or ethidium homodimer 1 (EthD-1). The counting may be carried out automatically using an automated cell counting device (e.g., IN Cell Analyzer).

In the present invention, the cell number and/or the neurite length of the motor neurons which have been contacted with the test substance may be determined as "high", when the value of the cell number and/or the neurite length is 1.5 times or more, 1.6 times or more, 1.7 times or more, 1.8 times or more, 1.9 times or more, or 2 times or more than the value of the control cells. Note that the control cells in the present method include the motor neurons which have not been contacted with test substances, and the motor neurons which have been contacted with an agent that had been confirmed as non-effective.

In the present invention, the culture in step (3) may be carried out in the presence of said test substance. The culture period is not particularly limited as long as the cell number can be measured, and the period is, for example, one day or more, 2 days or more, 3 days or more, 4 or more days, 5 days or more, 6 days or more, 7 days or more, 8 days or more, 9 days or more, or 10 days or more, and most preferably 7 days.

Measuring the length of neurites can be carried out by visual observation, or by the use of cell imaging device (e.g., IN Cell Analyzer). In the method, the length of neurites may be measured as an area of neurites on the image. Also, for detecting motor neurons specifically, a vector encoding a fluorescent substance (e.g., GFP, etc.) driven by HB9 promotor may be introduced into the pluripotent stem cells in step (1), and then, step (2) to (5) may be performed.

<Method for Screening a Therapeutic Agent for Alzheimer's Type Dementia>

The present invention provides a method for screening a therapeutic agent for Alzheimer's disease, involving the following steps:

(1) generating neurons from induced pluripotent stem cells by the method described above, wherein the induced pluripotent stem cells have been produced from somatic cells isolated from a patient with Alzheimer's disease;

(2) bringing a test substance into contact with the neurons obtained in step (1);

(3) culturing the neurons which have been contacted with the substance in step (2) and the neurons which have not been contacted with the substance (i.e., control cells), and measuring the amount of Aβ42 in the medium;

(4) selecting a test substance as the therapeutic agent for Alzheimer's disease, when the amount of Aβ42 in the medium of the neurons which have been contacted with said substance is lower than the amount of Aβ42 in the medium of control cells.

In the present invention, a pluripotent stem cell derived from a patient with familial or sporadic Alzheimer's disease can be used as an Alzheimer's disease patient-derived pluripotent stem cell. A pluripotent stem cell derived from a familial ALS patient is preferable, and a pluripotent stem cell derived from a familial ALS patient having one or more mutations in presenilin 1 gene is more preferable.

In the present invention, a measurement of the amount of Aβ42 in culture medium may be carried out by a method well known to those skilled in the art, for example, but not limited to, by ELISA using supernatant of the medium. The ELISA may be performed by the use of, for example, MSD Abeta 3 plex (38, 40, 42) assay plate (Meso Scale Discovery), and the human/rat β-amyloid (42) ELISA Kit Wako (WAKO), etc.

As an index, a value obtained by dividing the amount of Aβ42 by the amount of Aβ40 (Aβ42/Aβ40) can also be used as well as the the amount of Aβ42. A supernatant of culture, for example, a supernatant of 2 day-culture (a medium recovered 2 days after the last medium exchange), may be subjected to the measurement.

In the screening method of a therapeutic agent for Alzheimer's disease, a test substance similar to that described in the screening method of a therapeutic agent for amyotrophic lateral sclerosis can be used as a test substance (i.e., candidate agent).

<Therapeutic Composition for Motor Neuron Disease or Nerve Injury>

A pluripotent stem cell, which is derived from a healthy subject and into the chromosome of which an exogenous nucleic acid (in which a nucleic acid encoding Lhx3, a nucleic acid encoding Ngn2, and a nucleic acid encoding Isl1 are connected via a nucleic acid encoding a 2A sequence so as to be one continuous nucleic acid, and the continuous nucleic acid is operably connected to a drug responsive promoter) has been introduced according to the method of the present invention, and a motor neuron (including those at a differentiation stage in mid-course) obtained by inducing differentiation of the pluripotent stem cell, can be used as therapeutic compositions (transplantation therapy agents) for motor neuron disease or nerve injury. A preferred target disease is a disease caused by the defect or injury of motor neurons. Examples of such a disease include amyotrophic lateral sclerosis (ALS), spinal muscular atrophy (SMA), and spinal and bulbar muscular atrophy.

Taking into consideration the high graft survival rate of thereof, the cells used as therapeutic composition are preferably the pluripotent stem cells and/or cells in a mid-course of differentiation into motor neurons, and more preferably the pluripotent stem cells.

The therapeutic composition of the present invention can be produced in the form of a parenteral preparation such as an injection, a suspension, or drops, by mixing the pluripotent stem cells and/or the motor neurons with a pharmaceutically acceptable carrier according to an ordinary means. Examples of a pharmaceutically acceptable carrier that can be comprised in the parenteral preparation include a normal saline and an aqueous solution for injection such as an isotonic solution comprising glucose or other auxiliary drugs (e.g., D-sorbitol, D-mannitol, sodium chloride, etc.). The preparation may be mixed, for example, with a buffer agent (e.g., a phosphate buffer, a sodium acetate buffer), a soothing agent (e.g., benzalkonium chloride, procaine hydrochloride, etc.), a stabilizer (e.g., human serum albumin, polyethylene glycol, etc.), a preservative, an antioxidant, and the like. For instance, when the present therapeutic composition is formulated in the form of an aqueous suspension, the cells may be suspended in the aqueous solution to a concentration of approximately $1 \times 10^5$ to $1 \times 10^8$ cells/mL.

Transplantation of the therapeutic composition can be carried out, for example, by injecting the aqueous suspension into the lesion site of neurodegeneration or nerve damage. The number of cells to be administered can be appropriately changed depending on the degree of the lesion and the like. For example, in the case of a human ALS patient, approximately $1 \times 10^5$ to $1 \times 10^8$ cells can be administered to the patient. By administering a drug, to which the drug responsive promoter is responsive, to the transplant patient, the pluripotent stem cell and/or motor neurons (in the mid-course of differentiation) can be converted to motor neurons in the lesion site, so that the lesion site can be treated. For example, when a tetracycline-responsive promoter is used as a drug responsive promoter, tetracycline or DOX is administered to the transplant patient in a pharmaceutically acceptable amount that is sufficient for the activation of the promoter, simultaneously with or before the transplantation, so that the treatment can be effectively carried out. The tetracycline or DOX may be administered, either in the form of a parenteral preparation such as an injection, a suspension or drops, or in the form of an oral preparation.

Moreover, the transplantation therapy may be used in combination with drug therapy. When the target disease is ALS, examples of the combined drug include the existing therapeutic drug for ALS, Riluzole (trade name: Rilutek (registered trademark) (Sanofi)), a 1,3-diphenyl urea derivative or a multikinase inhibitor described in WO2012/029994, an HMG-CoA reductase inhibitor described in WO2011/074690, and anacardic acid (Egawa, N et al., Sci Transl Med. 4(145): 145 ra104. doi: 10. 1126). These drugs can be used, for example, at a dose and/or by an administration route that are commonly used for the treatment of ALS.

Likewise, a pluripotent stem cell, which is derived from a healthy subject and into the chromosome of which an exogenous nucleic acid (in which a nucleic acid encoding Ngn2 is operably connected to a drug responsive promoter) is introduced according to the method of the present invention, and a neuron (including those at a differentiation stage in mid-course) obtained by inducing differentiation of the pluripotent stem cell, can be used as a transplantation therapy agent for neurodegenerative disease or nerve injury. A preferred target disease is Alzheimer-type dementia or the like. The pluripotent stem cell and/or the neuron have the same aspects as those of the above described pluripotent stem cell, into the chromosome of which an exogenous nucleic acid (in which a nucleic acid encoding Lhx3, a nucleic acid encoding Ngn2, and a nucleic acid encoding Isl1 are connected via a nucleic acid encoding a 2A sequence so as to be one continuous nucleic acid, and the continuous nucleic acid is operably connected to a drug responsive promoter) is introduced, and/or the above described motor neuron. The present pluripotent stem cell and/or neuron can be used as transplantation therapy agents for the disease or nerve injury.

<Blood Cell Obtained from Pluripotent Stem Cell, in Chromosome of which Exogenous Nucleic Acid is Inserted>

In the present invention, as a method of generating a motor neuron or a neuron from a pluripotent stem cell, the pluripotent stem cell according to the present invention, in chromosome of which the exogenous nucleic acid is inserted, may be induced to differentiate into a somatic cell, and then, the somatic cell may be induced to differentiate into a motor neuron or a neuron by contacting the somatic cell with a drug corresponding to the drug responsive promoter. The somatic cell to be differentiated from the pluripotent stem cell according to the present invention, is not particularly limited, and can be desirably a cell having a migration ability, such as a microglia or a blood cell. The somatic cells are particularly preferably monocytes and/or macrophages.

The present invention provides a blood cell that is induced from the pluripotent stem cells having the exogenous nucleic acid (in which a nucleic acid encoding Lhx3, a nucleic acid encoding Ngn2, and a nucleic acid encoding Isl1 are connected via a nucleic acid encoding a 2A sequence so as to be one continuous nucleic acid, and the continuous nucleic acid is operably connected to a drug responsive promoter) in the chromosome thereof. The blood cell is a cell capable of converting to a motor neuron in contact with a drug to which the promoter is responsive. Blood cells, and in particular, inflammatory cells can migrate into an affected ares of motor neuron disease or nerve injury and are predisposed to accumulate in the sites where motor neurons have disappeared. Thus, by converting those inflammatory cells to motor neurons in the defective sites, motor neurons can be effectively replenished.

Therefore, a blood cell obtained by inducing differentiation from the pluripotent stem cell, which is derived from a healthy subject and which has the exogenous nucleic acid (in which a nucleic acid encoding Lhx3, a nucleic acid encoding Ngn2, and a nucleic acid encoding Isl1 are connected via a nucleic acid encoding a 2A sequence so as to be one continuous nucleic acid, and the continuous nucleic acid is operably connected to a drug responsive promoter) in the chromosome thereof, is extremely useful as a transplantation therapy agent for motor neuron disease or nerve injury. The target disease may be a disease developing a pathological condition due to a defect or an injury of motor neurons. Examples of such disease include amyotrophic lateral sclerosis (ALS), spinal muscular atrophy (SMA), and spinal and bulbar muscular atrophy.

In the present invention, examples of the blood cells include monocytes, macrophages, neutrophils, eosinophils, basophiles, and lymphocytes. The blood cells are preferably monocytes or macrophages.

The blood cells can be obtained by inducing differentiation using methods well known to a person skilled in the art, for example, the methods described in Senju et al. Stem Cells, 27:1021-1031, 2009, WO2006/022330, WO2012/074106, Saeki K et al., Stem Cells. 27:59-67, 2009, Nishimura T et al. Cell Stem Cell. 12:114-126, 2013.

The blood cells can be also obtained, without any particular limitation, by culturing the pluripotent stem cells on OP9 cells (Nakano T, et al. Science 265:1098-1101, 1994), or forming an embryoid body, and collecting blood cells produced in a culture, and then isolating desired blood cells using each marker (e.g., CD68, CD14, CD11c, CD11b, CD32, CD43, CD69, CD44, CD154, CD19, CD20, CD4, CD8, etc.) as an indicator. In the present invention, preferred blood cells are monocytes and/or macrophages that express at least CD14, and such blood cells can be produced, for example, with reference to the method described in WO2012/115276, as appropriate. A method involving a step of co-culturing pluripotent stem cells with bone marrow-derived stromal cells and, a subsequent step of culturing the cells in the presence of a stem cell factor, a macrophage-colony stimulating factor, and interleukin-3, is more preferable.

The blood cell obtained as above can be suspended in the above described aqueous solution, and can be administered as a parenteral preparation into the body of a patient, for example, by intravenous injection or intra-arterial injection. Thereafter, as described above, a drug to which the drug responsive promoter is responsive can be administered to the above administered patient, so that the blood cells can be converted to motor neurons and thereby the treatment can be carried out. When a tetracycline-responsive promoter is used as a drug responsive promoter for example, tetracycline or DOX can be administered to the patient in the same manner as described above. When an affected are/site-specific replenishment of motor neurons is expected, tetracycline or DOX may be locally administered to the area/site. Alternatively, after the blood cells that have been administered into the blood accumulate in the affected area (the defective site lacking motor neurons) has elapsed, tetracycline or DOX may be locally administered to the area/site.

A therapeutic composition involving the blood cell as an active ingredient may be administered by multiple-dose administration, as necessary, or it can also be prepared to the form of a sustained-release preparation by a method known per se and can be then used. Furthermore, the therapeutic composition may be used in combination with other therapeutic agents for neurodegenerative disease or nerve injury, as described above, as appropriate.

At present, only Riluzole has been approved as a therapeutic agent for ALS. In recent years, it has been reported that Riluzole promotes phosphorylation of a cAMP responsive element (CRE)-binding protein (CREB), and thereby, activates a promoter of a glial cell-derived neurotrophic factor (GDNF) gene (a promoter having CRE) and induces the expression of the gene (Tsuchioka, M et al., Brain Res. 1384: 1-8 2011). Accordingly, in the present invention, if a promoter having one or more of the CRE were to be used as a drug responsive promoter and if a pluripotent stem cell, into the chromosome of which an exogenous nucleic acid comprising a nucleic acid encoding an MN factor that has been operably connected to the promoter is inserted, were to be produced, it would be anticipated that the expression of the MN factor will be induced by contacting the pluripotent stem cell with Riluzole. Therefore, if a therapeutic composition comprising, as active ingredients, such pluripotent stem cells and/or blood cells differentiated from the pluripotent stem cells were to be produced, motor neurons would be replenished to ALS patients by the combined use of the therapeutic composition and Riluzole (without addition of drugs such as tetracycline), and it would be anticipated that therapeutic effects will be obtained.

<Model Animal Having Human-Derived Motor Neurons/Neurons>

In the present invention, the method of producing a motor neuron or a neuron can further comprise a step of introducing the pluripotent stem cell, in which the motor neural-inducing factor or the neural-inducing factor that can be induced by the above described drug responsive promoter has been inserted, into an animal body, and a subsequent step of bringing a drug corresponding to the drug responsive promoter into contact with the pluripotent stem cell in the animal body, so as to produce a motor neuron or a neuron in the animal body. In the present invention, the animal means a mammal, and it is more preferably a mammal such as a human, a mouse or a rat.

Moreover, in the present invention, an animal into which a human-derived motor neuron or neuron is grafted can be produced by transplanting the pluripotent stem cell, in the chromosome of which the exogenous nucleic acid has been inserted, and/or the cells obtained by inducing differentiation from the pluripotent stem cells, into an animal. The animal is a preferred model animal that can be used to analyze the influence of a drug or external stress on human motor neurons or neurons in a more natural condition.

<Method of Identifying Therapeutic Effect-Specific Marker>

The present invention provides a method of identifying or detecting a marker specific to a subject for whom an investigational agent for motor neuron diseases or nerve injury has been confirmed to be effective (namely, a responder) or ineffective (namely, a non-responder).

The present method can be achieved by a method involving the following steps of (1) to (4):

(1) producing induced pluripotent stem cells from somatic cells isolated from a responder or a non-responder;

(2) generating motor neurons from the induced pluripotent stem cells obtained in step (1), by the above described method;

(3) measuring the amount of gene products in the motor neurons derived from the responder and the non-responder, which were obtained in step (2); and (4) identifying a gene product which amount is higher in the motor neurons derived from the responder than in the motor neurons derived from the non-responder as the responder-specific marker, or a gene product which amount is lower in the motor neurons derived from the responder than in the motor neurons derived from the non-responder as the non-responder-specific marker.

In the present invention, the specific marker means a gene product, which is able to distinguish a subject who has responded to treatment from a subject who has not responded to treatment, and whose expression level in the target cells (which are herein motor neurons derived from the responder) is different the level in the control cells. Examples of such a gene product include mRNA, MicroRNA, and a protein. In the present invention, the gene product may be any given gene product, and when the gene product is mRNA, an example of the mRNA is mRNA equipped in a DNA microarray chip used in gene expression differential analysis. An example of the DNA microarray chip is a DNA microarray chip commercially available from Agilent Technologies or GE Healthcare Biosciences. An example of the protein is a cell surface protein. An example of such a cell surface protein is a protein contained in BD Lyoplate (Registered Trademark) available from Japan BD.

The investigational agent for motor neuron disease or nerve injury means any given drug that is considered to have therapeutic effects on motor neuron disease or nerve injury. Examples of the investigational agent include Riluzole, pentoxifylline, verapamil, azathioprine, topiramate, amantadine, acetylcysteine, Fisosuchimin, vitamin C, cyclosporine, celecoxib, guanidine, lamotrigine, minocycline, tilorone, gabapentine and kenpaullone, but the examples are not limited thereto.

In the present invention, measurement of the expression of the gene product can be carried out by a method well known to those skilled in the art, for example, PCR, Northern blotting, Western blotting, immunostaining, microarray method, and the like.

The present invention provides a method of identifying or detecting a marker specific to a subject for whom an investigational agent for Alzheimer-type dementia has been confirmed to be effective (namely, a responder) or ineffective (namely, a non-responder).

The present method comprises the following steps (1) to (4):

(1) producing induced pluripotent stem cells from somatic cells isolated from a responder or a non-responder;

(2) generating neurons from the induced pluripotent stem cells obtained in step (1), by the method described above;

(3) measuring the amount of gene products in the neurons derived from the responder and the non-responder, which were obtained in step (2); and (4) identifying a gene product which amount is higher in the neurons derived from the responder than in the neurons derived from the non-responder as the responder-specific marker, or a gene product which amount is lower in the neurons derived from the responder than in the neurons derived from the non-responder as the non-responder-specific marker.

The investigational agent for Alzheimer-type dementia means any given drug that is assumed to have therapeutic effects on Alzheimer-type dementia, and examples of the investigational new drug include donepezil hydrochloride, memantine and galantamine, but the examples are not limited thereto.

<A Method of Selecting a Subject for Whom a Therapeutic Agent is Effective>

The present invention further provides a method of selecting a target, for whom a therapeutic agent is effective, using the corresponding markers specific to responder or non-responder described above.

In the present invention, the method of selecting a target for whom a therapeutic agent is effective is characterized by having the following steps (1) to (3):

(1) producing induced pluripotent stem cells from somatic cells isolated from a subject;

(2) generating motor neurons from the induced pluripotent stem cells obtained in step (1), by the method described above;

(3) detecting the presence or absence of a marker in the motor neurons obtained in step (2), wherein the marker has been identified as a responder-specific or a non-responder-specific marker by the method described above; and (4) selecting a subject as the subject for whom the therapeutic agent corresponding to said marker is effective, when the responder-specific marker has been detected, or the non-responder-specific marker has not been detected in the motor neurons derived from said subject.

The present invention further provides a method of selecting a subject for whom a therapeutic agent is effective, involving the following steps:

(1) producing induced pluripotent stem cells from somatic cells isolated from a subject;

(2) generating neurons from the induced pluripotent stem cells obtained in step (1), by the method described above;

(3) detecting the presence or absence of the a marker in the neurons obtained in step (2), wherein the marker has been identified as a responder-specific or a non-responder-specific marker by the method described above; and (4) selecting the subject as the subject for whom the therapeutic agent corresponding to said marker is effective, when the responder-specific marker is detected, or the non-responder-specific marker is not detected in the neurons derived from said subject.

EXAMPLES

The present invention is described below in more detail by way of Examples, but the scope of the present invention is not limited to the Examples.

Hereafter, a vector that expresses Lhx3, Ngn2, and Isl1 in response to tetracycline is sometimes referred to as "tetracycline-inducible MN factor expression vector", and a vector that expresses Ngn2 in response to tetracycline is sometimes referred to as "tetracycline-inducible N factor expression vector". Moreover, the region flanked with two Frt sequences or transposon sequences in said vector is sometimes referred to as "MN factor expression cassette" or "N factor expression cassette", respectively. Furthermore, a cell in which the MN factor expression cassette or the N factor expression cassette has been inserted in the chromosome thereof is sometimes referred to as "MN factor-introduced cell" or "N factor-introduced cell", respectively.

In the following examples, doxycycline (hereinafter abbreviated as DOX) was added to the medium for the purpose of inducing the activation of tetracycline-responsive promoter at a final concentration of 1 μg/ml, unless otherwise noted.

Example 1: Generation of Motor Neurons (iMN) from Mouse-Derived Pluripotent Stem Cells As described, regarding a method of generating iMN from pluripotent stem cells, Non Patent Literature 4 discloses a method comprising introducing Lhx3, Ngn2, and Isl1 genes into neural progenitor cells using adenovirus vectors (Non Patent Literature 4). In the method, it takes about 10 days to obtain neural progenitor cells from pluripotent stem cells, and then, additional 11 days are needed to obtain iMN from the neural progenitor cells. Among the three genes, Lhx3 and Ngn2 are transcription factors which expression is induced on and after the stage of neural progenitor cells when pluripotent stem cells are induced to differentiate into motor neurons by a conventional method Non Patent Literature 4).

Although those transcription factors were not expected to operate in undifferentiated cells, we assessed the effects of those genes when introduced into murine ES cells.

KH2 cell line was used as a mouse-derived ES cell line, which possesses Frt sequences downstream of ColA1 locus and expresses M2rtTA, a reverse tetracycline transactivator, under the control of endogenous R26 promoter (Beard C, et al, Genesis 2006; 44: 23-28). We constructed a tetracycline-inducible MN factor expression vector, in which a sequence encoding Lhx3, Ngn2, or Isl1 is linked via a 2A sequence and further linked to a sequence encoding mCherry via an IRES sequence, and the polynucleotide encoding said four genes resulting is functionally joined to a tetracycline inducible promoter (A part of the vector, a region flanked with the FRT sequences is shown in FIG. 1A), by modifying the pDEST31 expression vector (Invitrogen Life Technologies, Inc.). The tetracycline-inducible MN factor expression vector can express Lhx3, Ngn2, Isl1, and mCherry in a polycistronic manner in response to tetracycline. Since the vector has two Frt sequences upstream and downstream of the expression cassette encoding the above four genes, introducing the vector together with a nucleic acid encoding flipase into KH2 cells can easily results in production of a cell in which the region flanked with two Frt sequences (i.e., the expression cassette for MN factor) has been inserted in its chromosome.

This vector was introduced into 293T cells by lipofection method, and then DOX was added into the medium. The analysis at 24 hours after the addition of DOX revealed that the expression of Lhx3, Ngn2, and Isl1 proteins was induced (FIG. 1B).

<Introduction of DNA into Mouse-Derived E S Cells>

The tetracycline-inducible MN factor expression vector was introduced together with a nucleic acid encoding flipase into KH2 cells by electroporation method, and then, the KH2 cells in which the MN factor expression cassette had been inserted in the chromosome (namely, MN factor-introduced mouse ES cells) were selected. The cells were cultured on MEF (mouse embryonic fibroblasts) feeder cells in the medium for mouse ES cells (15% FBS/DMEM supplemented with LIF, β-mercaptoethanol, L-glutamine, nonessential amino acids and penicillin/streptomycin). Immunostaining analysis detected expression of marker genes for undifferentiated cells (NANOG and SSEA1), indicating that those cells maintained pluripotency (FIG. 1C). Furthermore, the fluorescence of mCherry was detected specifically in the DOX-treated groups (FIG. 1D), indicating that the gene expression was induced by DOX addition. In addition, synthesis of Isl1, Lhx3, and Ngn2 mRNAs was confirmed to be induced by DOX addition (FIG. 1E).

<Induction of Lhx3, Ngn2, and Isl1 Gene Expression>

Then, we induced the expression of Lhx3, Ngn2, and Isl1 genes in the MN factor-introduced mouse ES cells, according to the procedures described in FIG. 1F. The cells were dissociated using 0.25% trypsin, seeded into Matrigel-coated dishes, and then, cultured in the medium containing DOX (i.e., N3 medium supplemented with 1 μg/ml DOX, 1 μM retinoic acid (RA), 1 μM sonic hedgehog (Shh), 10 ng/ml BDNF, 10 ng/ml GDNF, and 10 ng/ml NT3 (The N3 medium is DMEM/F12 medium supplemented with 100 μg/ml apotransferrin, 5 μg/ml insulin, 30 nM selenite, 20 nM progesterone, and 100 nM putrescine.)) to induce the expression of the three genes. At 36 hours after the induction, cells with neuron-like morphology were observed. At 72 after the induction, there were many cells that appeared mature neuron-like morphology and expressed motor neuron markers (HB9 and ChAT) in addition to neuronal markers (β-III tubulin and MAP2) (FIG. 1G). Real-time PCR analysis confirmed that the expression level of HB9 and ChAT increased in the DOX-added groups (FIG. 1H).

Therefore, it was revealed that an introduction of Lhx3, Ngn2, and Isl1 genes into a mouse-derived pluripotent stem cell followed by an induction of expression of the three genes results in a production of a morphologically mature motor neuron (iMN) that expresses motor neuron-specific proteins, in only 3 days.

<Conditions Suitable for the Induction of Motor Neurons>

To find more suitable condition for inducing motor neurons in the present invention, type of medium to be added by DOX was studied. The MN factor-introduced mouse ES cells were cultured in the following four types of media for 3 days in the presence or absence of DOX, then, the number of β-III tubulin-positive cells was measured.

(1) DMEM/F12 medium supplemented with 10% KSR
(2) DMEM/F12 medium supplemented with 10% KSR, 1 μM RA, and 1 μM Shh
(3) N3 medium
(4) N3 medium supplemented with 1 μM RA and 1 μM Shh In consequence, the medium (4) plus DOX led to production of the maximum number of tubulin-positive cells (FIG. 2A). Thus, the medium (4) supplemented with 10 ng/ml BDNF, 10 ng/ml GDNF, and the 10 ng/ml NT3 was used in the following Examples to induce differentiation into motor neuron in vitro, unless otherwise specified. In the following Examples, the above medium supplemented with DOX (usually 1 µg/ml, unless otherwise specified) is referred to as "DOX-containing medium".

The period of DOX treatment was also investigated (FIG. 2B). The MN factor-introduced mouse ES cells were cultured in the DOX containing medium for three days, and then the medium was replaced with the DOX containing or DOX-free medium. After additional four days of culture, the expression level of HB9, ChAT, and Isl1 was analyzed by real-time PCR method. Regarding Isl1 mRNA, since it was hard to detect the endogenous mRNA alone, the sum of the endogenous mRNA and exogenous mRNA that had been transcribed from the MN factor expression cassette ("Isl1" in FIG. 2C), and the exogenous mRNA alone ("2A-Isl1" in FIG. 2C) were independently measured. The result (FIG. 2C) shows that there was no significant difference in the expression level of motor neuron marker genes (HB9, ChAT, and Isl1) between the cells treated with DOX for 3 days (dox withdraw) and the cells treated with DOX for 7 days (dox (+)), indicating that, even if the treatment with DOX was terminated on the 3rd day, the expression level of motor neuron marker genes did not decrease thereafter. In contrast, in the cells from which DOX had been removed on the 3rd day (dox withdraw), the expression level of the "2A-Isl1" significantly decreased on the 7th day, indicating that the expression of the MN factor quickly ceased after DOX withdrawal.

Accordingly, it was clarified that a three-day induction of Lhx3, Ngn2, and Isl1 expression is sufficient to induce the differentiation of a mouse-derived pluripotent stem cell into a motor neuron.

<Evaluation of the Properties of iMN>

To assess the functional property of the motor neurons (iMN) generated from mouse ES cells using the above method, we asked whether the iMN could form synapses with C2C12 cells (mouse striated muscle-derived cell lines, Science, 230, 758-, 1985). Prior to this analysis, C2C12 cells had been cultured in DMEM/F12 medium supplemented with 0.5% FBS, 10 µg/ml insulin, 5.5 µg/ml apotransferrin, 30 nM selenite and 1 mM L-glutamine for 7 days, so as to differentiate the cells into myotubes. Then, the MN factor introduced mouse ES cells were seeded into the C2C12 myotube culture (onto the myotubes) and cultured in the DOX-containing medium to induce differentiation of the ES cells into motor neurons. Immunohistochemical staining detected co-localization of synaptic vesicle protein 2 (SV2)-positive neurites of iMN and α-bungarotoxin-labeled acetylcholine receptors (FIG. 3A). This result indicates that a motor neuron generated from a murine pluripotent stem cell by the method of the present invention (iMN) is capable of forming synapses with a muscle cell (i.e., neuromuscular junction). Furthermore, calcium imaging analysis revealed that calcium influx of the C2C12 cells significantly increased only when the C2C12 cells had been co-cultured with iMN (FIG. 3B).

Thus, it was revealed that iMN generated from a mouse-derived pluripotent stem cell by the method according to the present invention has an ability to form a functional synapse with a muscle cell, as well as a native motor neuron.

We next assessed the electrophysiological properties of iMN by visualizing the cells that became into motor neurons. A DNA fragment having GFP coding sequence functionally linked to HB9 promotor (HB9::GFP, Lee S K, et al., Development, 131:3295, 2004, for a reference) was introduced into the MN factor-introduced mouse ES using a piggyBac transposon, so that the cells could express GFP when the HB9 promoter was activated. Differentiation of the cells was induced by adding DOX to the medium, and GFP fluorescence-expressing cells (i.e., GFP-positive cells) were observed 3 days after the induction (FIG. 1G). Then, whole cell patch-clamp recordings was performed on the GFP-positive cells from the 5th day to the 7th day after DOX addition, and Na+/K+ current was observed in all of the GFP-positive cells analyzed (10 cells). Furthermore, action potential was recorded in 90% of the cells analyzed (FIG. 3C). Since an inward current was induced upon addition of glutamic acid or GABA in the medium (FIG. 3D), the iMN was found to express receptors for the excitatory and inhibitory neurotransmitters.

Thus, the iMN generated from a mouse-derived pluripotent stem cell by the method according to the present invention was found to have an electrophysiological property similar to that of a native motor neuron.

From the above results, it was clarified that a motor neuron (iMN) having morphological and functional properties similar to those of a native motor neuron can be generated from a mouse-derived pluripotent stem cell, by introducing and inducing the expression of Lhx3, Ngn2, and Isl1 genes in the pluripotent stem cell.

Example 2: Generation of Motor Neurons (iMN) from Pluripotent Stem Cells Derived from a Model Mouse for Amyotrophic Lateral Sclerosis We next generated iMN from ALS model mouse-derived pluripotent stem cells, and assessed a similarity of the iMN to original motor neurons.

<Production of iPS Cells from ALS Model Mice>

Mouse embryonic fibroblasts (MEF) were prepared from transgenic mice having a human SOD1 gene (G93A mutant SOD1 gene, or wild-type SOD1 gene), and iPS cells were produced according to the method described in Okita K et al., Nature. 2007, vol. 448, pp. 313-317. The presence of the human SOD1 gene in the iPS cells was confirmed by sequencing of the gene (FIGS. 4A and B). Moreover, these iPS cells were confirmed to express ES cell marker genes (Eras, Esg1, Rex1, Oct3/4 and Sox2), not to express reprogramming factors, and to be able to differentiate into three germ layers (FIGS. 4C, 4D and 5). Hereinafter, the iPS cell established from the transgenic mouse having the G93A mutant SOD1 gene or wild-type SOD1 gene is referred to as G93A-derived mouse iPS cells or WT-derived mouse iPS cells, respectively.

<Introduction of DNA into the iPS Cells>

We tried to introduce Lhx3, Ngn2 and Isl1 genes into the G93A-derived mouse iPS cells and the WT-derived mouse iPS cells in the same manner using adenoviral vectors as used in Non Patent Literature 4. However, most of the cell died and the synchrony in differentiation into iMN was insufficient. Thus, we had diligently studied to dissolve the problems and found that transposon-, especially piggyBac transposon-mediated gene transfer (Woltjen K, et al, Nature 2009, 458 refer to 766-70.) could minimalize the cell death rate and further improve the synchrony in differentiation into iMN. In addition to murine iPS cells, similar good results were obtained for human-derived iPS cells. Thus, in the present invention, transposon-mediated gene transfer was preferentially used for introduction of MN factor into pluripotent stem cells.

FIG. 6A shows the tetracycline-inducible MN factor expression vector that was introduced into the mouse-derived iPS cells above. Like the vectors depicted in FIG.

1A, this vector can expresses MN factor and mCherry polycistronically in response to tetracycline. Since the vector has a piggyBac transposon sequence (TR) in place of Frt sequences, introduction of this vector together with a nucleic acid encoding piggyBac transposase into cells can easily produce a cell in which the MN factor expression cassette has been integrated into the chromosome (Woltjen K, et al, Nature. 2009, 458: 766-70). Although FIG. 6A shows the vector leading to the expression of both MN factor and mCherry in a polycistronic manner, a vector lacking mCherry coding sequence is also available for the present invention. We used such mCherry-lacking vector, too.

The vector shown in FIG. 6A and a nucleic acid encoding the piggyBac transposase were introduced into the G93A-derived mouse iPS cells and WT-derived mouse iPS cells, and then the cells in which the MN factor expression cassette had been inserted in the chromosome was selected. Those cells (i.e., MN factor-introduced G93A-derived mouse iPS cells, and MN factor-introduced WT-derived mouse iPS cells) maintained the expression of undifferentiated markers (SSEA1 and NANOG) (FIG. 6B) and high proliferating ability equivalent to the iPS cells prior to the introduction of vector.

<Induction of MN Factor Expression>

The MN factor-introduced G93A-derived mouse iPS cells and MN factor-introduced WT-derived mouse iPS cells were cultured in the DOX-containing medium to induce the expression of MN factor. As well as the mouse ES cells, a large number of HB9, β-III tubulin and ChAT-positive cells was observed on the 3rd day after induction of the factor (FIG. 6C), while GFAP-, a marker of astrocytes-positive cells was not observed.

Thus, it was confirmed that, even from a mouse iPS cell that is derived from a transgenic mouse having a human SOD1 gene (G93A mutant SOD1 gene, or wild-type SOD1 gene), a motor neuron can be generated by introducing and inducing the expression of MN factor, in a brief period of 3 days after the induction.

<Evaluation of the Properties of iMN>

Transgenic mouse carrying a human G93A mutant SOD1 gene is known to develop misfolding and aggregation of the mutant SOD1 protein in motor neurons, and such abnormal events are thought to be closely related to the death of motor neurons. Then, we asked whether the iMN generated from the iPS cells derived the transgenic mouse by the method of the present invention, could develop misfolding or aggregation of the mutant SOD1 protein. Immunostaining analysis using anti misfolded SOD1 antibodies (A5C3, B8H10 and C4F6, MEDIMABS: All those antibodies can recognize misfolded wild-type and mutated SOD1 proteins) indicates that there were many aggregates recognized by those antibodies, within the iMN generated from the MN factor-introduced G93A-derived mouse iPS cells (FIG. 6D). On the other hand, no aggregates was recognized by those antibodies, in the iMN generated from the MN factor-introduced WT-derived mouse iPS cells (FIG. 6D).

Next, we assessed the presence or absence of cell death. The cells were cultured in the DOX-containing medium for 4 days and further cultured in the DOX-free medium, and the number of HB9 and β-III tubulin-positive cell (i.e., iMN number) was measured on day 4 and day 6 after the start of the DOX-treatment. FIG. 6E shows the survival rate of iMN, that was obtained by dividing the number of iMN on the 6th day by the number on the 4th day (i.e., the number of HB9 and β-III tubulin-positive cell on the 6th day/the number of HB9 and β-III tubulin-positive cell on the 4th day) after the start of the DOX-treatment. The figure indicates that the iMN generated from the MN factor-introduced G93A-derived mouse iPS cells underwent massive cell death from the 4th day to the 6th day after the induction, while the iMN generated from the MN factor-introduced WT-derived mouse iPS cells did not (FIG. 6E). In addition, measurement of LDH level in the medium on the 4th day and the 6th day after the induction revealed that the LDH level of the iMN culture from the MN factor-introduced G93A-derived mouse iPS cells culture was significantly higher than the LDH level of the iMN culture from the MN factor-introduced WT-derived mouse iPS cells culture (FIG. 6F). Furthermore, measurement of neurite length of HB9 and β-III tubulin-positive cells deom the 4th day to the 6th day after the induction revealed that the neurite length of the iMN generated from the MN factor-introduced WT-derived mouse iPS cells markedly increased (extended neurites (i.e., massive outgrowth had occurred), while the neurite length of the iMN generated from the MN factor-introduced G93A-derived mouse iPS cells did not almost increase (i.e., neurite outgrowth had stopped) (FIG. 6H).

Accordingly, it was revealed that the iMN generated from an ALS model mouse carrying a human mutant SOD1 gene by the method of the present invention autonomously develops misfolding and aggregation of SOD1 protein, and undergoes to cell death. Furthermore, LDH level in the medium or neurite length can be used as an indicator of the cell death.

It has been reported that the motor neuron death of the mice carrying human G93A mutant SOD1 gene could be alleviated when the motor neurons are coexisted with wild-type glial cells (astrocytes). Then, we induced differentiation of the MN factor-introduced G93A-derived mouse iPS cells in the presence of wild-type mouse-derived astrocytes, and then, assessed the survival rate of the iMN (i.e., the number of HB9 and β-III tubulin-positive cell on the 6th day/the number of HB9 and β-III tubulin-positive cell on the 4th day) in the same manner as described above (FIG. 6G). The results indicates the survival rate of the iMN generated from the MN factor-introduced G93A-derived mouse iPS cells in FIG. 6G (induction of differentiation in the presence astrocytes) was higher than the survival rate in FIG. 6E (induction of differentiation in the absence of astrocytes). Therefore, it was revealed that the death of the iMN generated from the MN factor-introduced G93A-derived mouse iPS cell can be alleviated when the iMN has been coexisted with wild-type astrocytes.

From the above results, by using the method according to the present invention, iMN that autonomously develops properties characteristic to ALS can be generated from the ALS model mouse-derived pluripotent stem cells.

As described above, taking the results of recent human clinical trials into consideration, there has been a growing interest in the use of human-derived neural cells as an analysis system. Therefore, we generated iMN from human pluripotent stem cells using the method according to the present invention and evaluated its properties.

Example 3: Generation of iMN from Human (Normal Control)-Derived Pluripotent Stem Cells <Introduction of DNA into Human-Derived Pluripotent Stem Cells>

MN factor-introduced normal control-derived human iPS cells was generated from human-derived iPS cells (Takahashi K, et al., Cell. 2007, vol 131, pp 861-872.) by introducing the vector shown in FIG. 6A in the same manner as described above. Then, the cells were cultured on SNL cells in the primate embryonic stem cell medium (Repro- CELL) supplemented with 4 ng/ml basic fibroblast growth factor, and confirmed to express undifferentiated markers (NANOG and SSEA4) (FIG. 7A) and maintaining the high proliferating ability equivalent to that of unintroduced iPS cells.

<Induction of MN Factor Expression>

The MN factor-introduced normal control-derived human iPS cells were dissociated using Acutase and transferred to the Matrigel-coated dish, and then cultured in the DOX-containing medium to induce differentiation into motor neurons (FIG. 7B). At 7 days after the start of the induction, a large number of HB9, β-III tubulin and ChAT-positive cells with mature neuronal-like morphology were observed (FIG. 7C). Moreover, PCR analysis revealed that the expression level of HB9 and ChAT in those cells increased by adding DOX (FIG. 7D).

Therefore, a human-derived pluripotent stem cell was found to differentiate into a morphologically mature iMN that expresses motor neuron-specific proteins, in approximately 7 days after the expression of exogenously introduced Lhx3, Ngn2, and Isl1 genes is induced.

<Characterization of iMN>

The synapse forming ability of the MN factor-introduced normal control-derived human iPS cells with the C2C12 cell was analyzed using the methods described above. At 10 days post induction of differentiation, co-localization of the SV2-positive neurites extended from the iMN and the α-bungarotoxin-labeled acetylcholine receptors was observed (FIG. 7E). We also generated HB9::GFP inserted MN factor-introduced normal control-derived human iPS cells, in the same manner as described above. The HB9::GFP inserted iPS cells were cultured in the DOX containing medium together with mouse-derived primary astrocytes for 8-14 days, then, subjected to an electrophysiological analysis with whole-cell patch-clamp recordings.

As a result, in all of the GFP-positive cells analyzed (10 cells), Na+/K+ current was observed and furthermore action potential was measured (FIG. 7F). Further, the inward current was induced upon addition of glutamic acid or GABA in the medium (FIG. 3D), thereby, those cells were confirmed to express receptors for the excitatory and inhibitory neurotransmitters (FIG. 7G).

Thus, iMN generated from a human-derived pluripotent stem cell by the method according to the present invention has electrophysiological properties similar to that of a native motor neuron.

From the above results, it was clarified that iMN with morphological and functional properties similar to a native motor neuron is obtained from a human-derived pluripotent stem cell by introducing the expression of Lhx3, Ngn2, and Isl1 genes.

Example 4: Generation of iMN from Human (ALS Patient)-Derived Pluripotent Stem Cells Next, we generated iMN from ALS patient-derived pluripotent stem and analyzed the similarity to native motor neurons.

<Production of Human-Derived iPS Cells>

Dermal fibroblasts were prepared from two normal controls (Control1 and Control2) and two ALS patients with a mutation in SOD1 gene with patient consent, and OCT3/4, SOX2, KLF4, L-MYC, LIN28, and a small haipin RNA for p53 were introduced into the fibroblasts using episomal vectors according to the method described in Okita K, et al, Nat Methods 2011, 8:409-12, to establish iPS cell lines (Kondo T, et al, Cell Stem Cell, 12:487-96, 2013). FIG. 10A shows that the iPS cells derived from ALS patients have the mutant SOD1 gene.

Note that the mutations of SOD1 gene in the two ALS patients are L144FVX mutation (causing amino acid changes at the 144th amino acid (leucine) and the following to phenylalanine-valine-stop codon, sometimes referred to as SOD1-L144FVX) and G93S mutation (causing a substitution from glycine to serine at position 93, sometimes referred to as SOD1-G93S), respectively. Hereinafter, the iPS cells established from the Control 1, the Control 2, the patient with SOD1-L144FVX mutation, and the patient with SOD1-G93S mutation are referred to as the Control 1-derived iPS cells, the Control 2-derived iPS cells, the L144FVX-derived iPS cells, and G93S-derived iPS cells, respectively.

<Introduction of DNA into Human-Derived iPS Cells>

The vector shown in FIG. 6A was introduced into the four iPS cell lines established above, and the iPS cells in which the MN factor expression cassette had been inserted in the chromosome resulting were generated. Hereinafter, the iPS cells generated from the Control 1-derived iPS cells, the Control 2-derived iPS cells, the L144FVX-derived iPS cells, and G93 S-derived iPS cells are referred to as the MN factor-introduced Control 1-derived iPS cells, the MN factor-introduced Control 2-derived iPS cells, the MN factor-introduced L144FVX-derived iPS cells, and MN factor-introduced G93 S-derived iPS cells, respectively.

<Induction of MN Factor Expression and Evaluation of Properties of the iMN>

The four types of MN factor-introduced human-derived iPS cells were cultured in the DOX-containing medium to induce the expression of the MN factor. FIG. 10B illustrates a timeline of the induction. Immunostaining analysis on the 7th day post induction revealed that approximately 50% of the cells were positive for HB9 and β-III tubulin (FIG. 10C). Further, immunostaining analysis using the anti-misfolded SOD1 antibodies detected aggregates labeled with the anti-misfolded SOD1 antibodies only in the iMN generated from the MN factor-introduced L144FVX-derived iPS cells or the MN factor-introduced G93 S-derived iPS cells (FIG. 10D). We measured the number of βIII tubulin-positive cells as the number of iMN, on the 7th day and the 14th day post induction, and calculated a survival rate of iMN by dividing the number of iMN on the 7th day by the number of iMN on the 14th day. The graph in FIG. 10E shows the survival rate of iMN, indicating that the number of iMN generated from the MN factor-introduced Control 1-derived iPS cells, or the MN factor-introduced Control 2-derived iPS cells, was almost constant from the 7th day to the 14th day after the induction. As contrasted with this, the number of iMN generated from the MN factor-introduced L144FVX-derived iPS cells, or the MN factor-introduced G93 S-derived iPS cells drastically decreased from the 7th day to the 14th day after the induction, clearly indicating that those iMN underwent cell death.

Thus, it was clarified that, even from the iPS cell derived from a familial ALS patient, as well as from the pluripotent stem cells derived from a model mice, iMN that can sufficiently reproduce properties characteristic to the disease such as misfolding/aggregation of SOD1 protein or autonomous cell death can be obtained by the method according to the present invention.

Example 5: Synchrony of Differentiation from Pluripotent Stem Cells to iMN

We next analyzed a time course of iMN generation using a method according to the present invention.

<Time Course of iMN Generation from Mouse-Derived Pluripotent Stem Cells>

We generated MN factor-introduced iPS cells from the iPS cells prepared from wild-type mouse (Takahashi K, et al, Cell 2007, 131: 861-72 reference), using the same method as used in Example 2. The resulting cells were seeded into a 96-well plate and cultured in the DOX-containing medium to induce the expression of MN factor. The cells were then subjected to immunostaining analysis and the number of SSES1 or NCAM-positive cells was measured at 10, 24, 36, 48, or 72 hours after initiation of the induction. We also measured the number of the cell that was positive for NCAM and possessed a fully thickened cell body together with neurites as the number of iMN. The total cell number was measured by DAPI staining. The results are shown in FIG. 11A.

As can be seen in FIG. 11A, after the induction start, SSES1 positive cells (i.e., cells maintaining undifferentiated status) decreased rapidly, and completely disappeared by 48 hours after the induction. In contrast, NCAM-positive cells (i.e., differentiating cells into neuronal cells) appeared immediately after the start of induction, and NCAM-positive cells having neurites and a sufficiently thickened cell body (i.e., iMN) appeared around 24 hours after the induction. The number of iMN rapidly increased from 24 to 72 hours and reached to approximately 50% of the total cells in culture by 72 hours, and afterward hardly increased. The cells that did not meet the above criteria for iMN even at 72 hours after the induction is thought to be converted into non-neuronal cells, since those cells were confirmed not to express SSES1 nor NCAM.

Accordingly, it was clarified that the differentiation from the MN factor-introduced pluripotent stem cell according to the present invention into iMN is highly synchronized. Regarding the MN factor-introduced mouse-derived pluripotent stem cell, it was demonstrated that those cells lose the nature of iPS cells immediately after induction of the differentiation, and approximately 50% of them becomes iMN from the 2nd day to the 3rd day after the induction.

<Time Course of iMN Generation from Human-Derived Pluripotent Stem Cells>

The same analysis was carried out on the MN factor-introduced Control-derived iPS cells, which had been prepared in Example 3. As shown in FIG. 11B, NCAM-positive cells having neurites and a sufficiently thickened cell body (i.e., iMN) were hardly found on the 5th day, but then sharply increased and reached approximately 25% by the 7th day after the start of the induction. Accordingly, it became clear that human-derived pluripotent stem cells are converted to iMN synchronously during a period from 5 to 7 days after induction of the expression of MN factor. Although there were a large number of cells that were positive for NCAM or βIII tubulin and had a long neurite even on the 5th day after the start of the induction, the thickness of the cell body and the expression level of HB9 of those cells were insufficient (relatively flat cell body).

From these results, it became clear that the pluripotent stem cell according to the present invention, that has the MN factor expression cassette in the chromosome thereof, promptly and synchronously differentiates into iMN, when the expression of the MN factor is induced.

As one reason for that the high synchrony could be obtained by the present method is considered to be the use of a transposon as a system of introducing the MN factor into pluripotent stem cells. In general, since a virus vector leads to a prompt and high expression of a gene of interest, it has been most preferably used for the purpose of inducing differentiation. However, contrary to expectations, when Ngn2, Lhx3, and/or Isl1 genes had been introduced and allowed to express in pluripotent stem cells in the present invention, the synchrony in differentiation became higher in the case of using a transposon compared to that of using a virus vector (data not disclosed).

In the Examples of the present application, we introduced a vector encoding a drug-responsive MN factor into pluripotent stem cells, and the resulting MN factor-introduced pluripotent stem cells (namely, heterogeneous cell population in the copy-number of the MN factor expression cassette and the inserted sites thereof) were directly used for individual experiments without isolation of clones. Therefore, in the present method, if a homogenous cell population having an identical copy-numbers of MN factor inserted in identical site (i.e., clone) is established from the heterogeneous cell population and the induction of differentiation is performed on such homogenous cells, a synchrony and efficiency in differentiation into iMN are expected to be much improved.

Example 6: Synchrony of Cell Death of ALS Patient/Model Mouse-Derived iMN

We next analyzed a time course of cell death of the iMN induced from ALS model mouse-derived iPS cells in detail.

The MN factor-introduced G93A-derived mouse iPS cells or the MN factor-introduced WT-derived mouse iPS cells, which had been prepared in Example 2, were seeded into a 96-well plate and cultured in the DOX-containing medium to induce the expression of MN factor. On the 4th, 6th, and the 10th day after the start of DOX-treatment, immunostaining (β-III tubulin) and morphological observation were carried out, and the number of iMN was counted. The results are shown in Table 1 and FIG. 12A.

TABLE 1

| Origin of iPS cell | MN number (Mean ± SE) | | |
| --- | --- | --- | --- |
| | Day 4 | Day 6 | Day 10 |
| Non-transgenic mouse | 58.4 ± 8.1 | 62.3 ± 7.6 | 57.2 ± 8.1 |
| Human wild-type SOD1-transgenic mouse | 65.8 ± 4.4 | 51.9 ± 6.8 | 44.3 ± 6.1 |
| Human mutant SOD1-transgenic mouse | 46.8 ± 4.5 | 25.6 ± 3.6 | 8.7 ± 1.8 |

As shown in Table 1 and FIG. 12A, the number of iMN that has been induced from the MN factor-introduced iPS cells derived from non-transgenic control or wild-type SOD1-transgenic mouse did not largely changed from the 4th day to the 10th day after the start of the induction of MN factor expression, indicating that those iMN hardly undergo cell death. In contrast, the number of iMN that has been differentiated from the MN factor-introduced iPS cells derived from G93A-mutant mouse decreased to approximately 54.7% by the 6th day and approximately 18.6% by the 10th day, compared with the number on the 4th day after the start of the induction of MN factor expression.

Therefore, it was clarified that the pluripotent stem cells that are derived from an ALS model mouse having a mutant human SOD1 gene and have an exogenous nucleic acid encoding MN factor under the control of an inducible promoter within the chromosome thereof, differentiate into iMN so that the number of iMN becomes the maximum from the 2nd day to the 3rd day, but thereafter, immediately start to die so that the majority of them dies from the 8th day to the 10th day after the start of induction of MN factor expression.

Furthermore, the same analysis was carried out on MN factor-introduced Control 1-derived iPS cells, and the MN factor-introduced L144FVX-derived iPS cells. The results are shown in Table 2 and FIG. 12B.

TABLE 2

| Origin of iPS cell | MN number (Mean ± SE) | |
|---|---|---|
| | Day 7 | Day 14 |
| Normal control | 463.1 ± 14.1 | 439.3 ± 24.4 |
| ALS patient with SOD1-L144FVX mutation | 424.8 ± 9.6 | 19.4 ± 3.3 |

As shown in Table 2 and FIG. 12B, when the expression of the MN factor was induced in the iPS cells derived from the normal control, the number of iMN was almost constant form the 7th day to the 14th day after the start of the induction, indicating that the iMN did not undergo cell death substantially. In contrast, when the expression of the MN factor was induced in the iPS cells derived from the ALS patient having L144FVX mutation SOD1 gene, the number of iMN became the maximum on the 7th day, but thereafter, rapidly decreased and on the on the 14th day reached to approximately 4.6% of the number on the 7th day after the start of the induction, indicating that the iMN started to die from the 7th day after the start of the induction of MN factor expression.

Incidentally, a result similar to that using MN factor-introduced L144FVX-derived iPS cells was obtained when the MN factor-introduced G93 S-derived iPS cell was used, although the result was omitted in the present specification.

From the above, it was clarified that the MN factor-introduced iPS cell prepared from a human or a mouse having a mutant SOD1 gene is autonomously directed to cell death immediately after differentiated into a motor neuron (iMN) by the induction of the MN factor expression. The motor neuron death is not due to an external death signal, but an autonomous cell death due to the expression of mutant SOD1. It has been reported that motor neurons/iMN generated from a patient having mutant SOD1 gene by a conventional method, do not undergo massive cell death autonomously, and therefore, an addition of certain factor is needed to induce the death of those cells. Furthermore, the death of those motor neurons has been proven not to be substantially suppressed by Riluzole, only approved drug for treating ALS, thereby, the differences with native (within the body of ALS patients) motor neurons has been pointed out.

Therefore, we assessed the effect of Riluzole on the death of MN according to the present invention.

Example 7: Drug Sensitivity of iMN Derived from ALS Patients

As in Example 6, the MN factor-introduced L144FVX-derived iPS cells were seeded in a 96-well and cultured in the DOX-containing medium to induce the expression of MN factor (the day is referred to as Day0). Various concentrations of Riluzole (0, 12.5, 25, 50, 100 µM) were applied on the 7th day (=Day7), and the number iMN was measured on the 14th day (=Day14) according to the above method. FIG. 13A shows the results of immunostaining of the cells using anti β-III tubulin antibody on Day7 and Day14. The results shows that cell death in Riluzole-treated wells was significantly suppressed compared to that in untreated wells.

The results of measuring the number of iMN are shown in Table 3 and FIG. 13B. It becomes clear that cell death of iMN can be suppressed by Riluzole in a concentration-dependent manner up to 50 µM.

TABLE 3

| MN number | MN number on Day 14 in Riluzole-treated well (Mean ± SD) | | | | |
|---|---|---|---|---|---|
| On Day 7 | 0 µM | 12.5 µM | 25.0 µM | 50.0 µM | 100.0 µM |
| 111.7 ± 6.8 | 26.5 ± 3.7 | 35.8 ± 3.1 | 44.5 ± 3.5 | 66.0 ± 7.7 | 19.0 ± 2.7 |

From above, it was clarified that iMN generated from the iPS cell that is derived from an ALS patient having a mutant SOD1 gene and retains the exogenous nucleic acid according to the present invention (i.e., the nucleic acid encoding MN factor driven by a drug-responsive promoter) in its chromosome undergoes cell death due to the toxicity of the mutant SOD1 gene product, as well as a motor neuron having the same mutant SOD1 gene in ALS patient, and the cell death can be efficiently suppressed by an ALS therapeutic agent (Riluzole). No system of cell death of motor neurons or iMN that can be effectively suppressed by Riluzole has been reported so far.

Thus, the cell death system of iMN according to the present invention is thought to be quite useful as a screening and evaluation system of therapeutic and prophylactic drugs for ALS.

Example 8: Drug Screening Using ALS Patient-Derived iMN

An overview of a screening system of therapeutic and prophylactic drugs for ALS, using the MN factor-introduced iPS cells having a mutant SOD1 gene according to the present invention is shown in FIG. 14.

First, the DNA shown in FIG. 6A (namely, DNA encoding MN factor driven by an inducible promoter) is introduced into an ALS patient-derived iPS cell, or a human iPS cell prepared from a cell into which a mutant gene associated with ALS has been introduced, thereby obtaining an iPS cell into which the DNA has been introduced. Resulting iPS cell can be stably maintained by culture, while maintaining undifferentiation ability, pluripotency, and high proliferating ability.

These MN factor-introduced iPS cells are seeded into a 96-well plate (=Day 0), and DOX is then added to the medium, so that differentiation of the iPS cells into iMN is induced. Six to seven days after addition of DOX, iMN is generated, but the generated iMN is promptly directed to cell death. Thus, around the 7th day after addition of DOX (=Day 7), a test compound is applied, and the number of iMN is then count around the 14th day (=Day 14), so that the cell death-suppressing effect of the test compound on the iMN can be evaluated. The number of iMN can be automatically counted using an apparatus such as a cell image analyzer.

Using the cell death system of iMN according to the present invention, the existing drugs were screened.

First, the accuracy of the present analysis system was evaluated. The iPS cells derived from an ALS patient having SOD1-L144FVX mutation, into which the MN factor had been introduced, were seeded in a 96-well plate and cultured in the DOX-containing medium, so as to induce the expression of MN factor (=Day 0). Seven days later (=Day 7), DMSO was added as a negative control, and Kenpaullone (50 µM, Cell Stem Cell, vol. 12, pp. 1-14, 2013) that was reported to increase the survival rate of MN generated from ALS patient-derived iPS cells having a mutant SOD1 gene, was added as a positive control, to a control well, respectively. On the 14th day, the cells were fixed and then immunostained for 0111 tubulin. The stained image was analyzed using IN Cell Analyzer 6000 (GE Healthcare), and the number of iMN was measured. The results are shown in FIG. 15A. The Z'-score in the present analysis was 0.65. Since the Z'-score was 0.5 or greater, it was demonstrated that a variation in the values obtained in the present experimental system is extremely small, and therefore, the present experimental system has an extremely high accuracy.

Next, using this system, existing drug compounds (approximately 1200 types) were screened. The test compound was applied to a well on Day 7, and the number of iMN was measured on Day 14. The results are shown in FIG. 15B. As is clear from FIG. 15B, it has been confirmed again that Riluzole suppresses cell death of the iMN in a concentration-dependent manner.

The existing drug compounds included several compounds that had been confirmed to have therapeutic effects on ALS model mice but had not been confirmed to have significant therapeutic effects in a clinical trial using humans. The results regarding these compounds are shown in FIG. 15B (15 types of compounds, regarding which there are no underlines below the compound names), indicating that all of these compounds could not effectively suppress cell death of the iMN.

From these results, it was clarified that a system for analyzing cell death utilized the MN factor-introduced iPS cells having a mutant SOD1 gene according to the present invention, can be a screening system for therapeutic and/or prophylactic agents for ALS, having high reliability and accuracy. Moreover, it became clear that the ALS patient-derived iMN generated by the method according to the present invention exhibits sensitivity correlating with the test results, to several types of drugs analyzed in human clinical trials.

Example 9: A Method of Generating iMN Via Blood Cells from Pluripotent Stem Cells Blood cells are most easily introduced into an individual animal. In particular, blood cells having migration capacity, such as monocytes or microphages, can autonomously migrate into the deep portion of an individual animal. Hence, the present inventors conducted studies regarding the possibility of differentiation of the DNA-introduced pluripotent stem cells according to the present invention into motor neurons via blood cells.

The MN factor-introduced mouse iPS cells, which had been prepared in Example 1, were seeded on OP9 cells (Day 0), and then cultured in αMEM containing 10% FBS. On the 5th day after initiation of the culture (FIG. 8A), Flk-1-positive and SSEA-1-negative cells were collected using FACS (FIG. 8B). The collected cells were seeded onto OP9 cells, and were then cultured in αMEM supplemented with 100 ng/ml mSCF, 20 ng/ml mIL-3 and 10 ng/ml mM-CSF. Seven days later (12th day after initiation of the culture), Giemsa staining was performed on the cells. As a result, the presence of monocytes/macrophages was found (FIG. 8C), demonstrating that the pluripotent stem cells were induced to differentiate into blood cells.

The obtained monocytes/macrophages were dissociated using accumax, were then seeded into a dish that had been coated with matrigel, and then cultured in N3 medium. On the following day, 1 µg/ml Doxycycline, 1 µM retinoic acid and 1 µM Smoothened Agonist (SAG) were added to the N3 medium, and the cells were then cultured. Eight days later, induction of neurons was evaluated by immunostaining. As a result, motor neurons were observed (FIG. 9).

Therefore, the MN factor introduced pluripotent stem cells according to the present invention after being differentiated into blood cells, and by inducing the expression of the MN factor, was shown to be differentiated into iMN in about seven days.

Therefore, it was demonstrated that the MN factor-introduced pluripotent stem cell according to the present invention is allowed to differentiate into a blood cell, and the blood cell can further differentiate into iMN in approximately 7 days when the expression of the MN factor is induced.

Example 10: Generation of iN from Mouse-Derived Pluripotent Stem Cells

In the above sections, attention has been paid on a motor neuron, which has been focused as a study target for ALS or SMA, and an invention relating to a method for producing motor neurons from pluripotent stem cells has been described. On the other hand, common neurons have a high demand for studies. Previously, the present inventors had also conducted studies regarding Alzheimer's type dementia, using neurons obtained from pluripotent stem cells over approximately 2 months according to the conventional method (adhesion method). In the process of seeking the method for producing iMN, the present inventors have found that, among the factors for inducing differentiation into motor neurons, when only the Ngn2 gene has been introduced and allowed to express in pluripotent stem cells, the cells can be induced to iN extremely promptly with high efficiency.

<DNA Encoding Ngn2 Gene Under the Control of a Tetracycline-Responsive Promoter>

As a DNA to be introduced into pluripotent stem cells, DNA having a tetracycline-inducible Ngn2 expression cassette and an rtTA expression cassette driven by EF1α promotor was constructed. In the DNA, the nucleotide encoding the above two expression cassettes is flanked with a set of Terminal repeat (TR) of piggyBac transposon, so that those expression cassettes can be inserted in chromosome by piggyBac transposon (Tanaka A, et al, PLoS One 2013, 8: e61540). Hereinafter, said DNA is referred to as "DNA encoding Ngn2 gene under the control of tetracycline-responsive promoter".

<Generation of iN from the Mouse-Derived iPS Cells>

The DNA encoding Ngn2 gene under the control of tetracycline-responsive promoter and a nucleic acid encoding transposase (Woltjen K, et al, Nature 2009, 458: 766-70) were introduced into the wild-type mouse-derived iPS cells (Takahashi K, et al, Cell 2007, 131:861-72 reference), and a stable cell line in which said DNA had been inserted in the genome was established. Subsequently, the N factor-introduced iPS cells were dissociated into single cells, seeded into matrigel (BD)-coated dishes, and cultured in the DOX-containing medium (i.e., N3 medium supplemented with 1 µg/ml DOX, 10 ng/ml BDNF, and 10 ng/ml GDNF and 10 ng/ml NT3) to induce the expression of the Ngn2. βIII tublin positive cells were slightly observed on the 2nd day, and approximately 90% of the cells became positive for βIII tublin, MAP2 and vGLT1 (i.e., glutaminergic neurons) on the 3rd day after initiation of the induction. The number of βIII tublin-positive cells no longer increased on and after the 4th day after initiation of the induction (FIG. 16A).

Accordingly, it was clarified that, when Ngn2 gene is introduced and allowed to express in mouse-derived pluripotent stem cells, almost all the cells are synchronously converted into iN from the 2nd day to the 3rd day after induction of the Ngn2 gene expression.

Example 11: Generation of iN from Human-Derived Pluripotent Stem Cells

We next attempted to generate iN from pluripotent stem cells derived from patients with Alzheimer's disease.
<Production of iPS Cells from Patients with Alzheimer's Disease>

Human-derived iPS cells (N112E14 (normal control derived), AD8K213 (derived from sporadic Alzheimer's patients), AD15E11 (presenilin (PS1) mutant), APP1E211 (APP-E693 delta)) were produced using the following method. AD8K213 and APP1E211 were produced according to the method described in Okita K, et al, Nat Methods 2011, 8:409-12, by introducing OCT3/4, SOX2, KLF4, L-MYC, LIN28, and a small haipin RNA for p53 into dermal fibroblasts that had been prepared from the patients with patient consent, using episomal vectors (Kondo T, et al, Cell Stem Cell, 12:487-96, 2013). N112E14 and AD15E11 were also produced from dermal fibroblasts that had been prepared from the patients with patient consent, using episomal vectors.
<Generation of iN from the iPS Cells Derived from Patients with Alzheimer's Disease>

According to the method described above, the DNA encoding Ngn2 gene under the control of tetracycline-responsive promoter was introduced into the four types of human iPS cells obtained by the above-described method, and stable cell lines in which said DNA had been inserted in the genome (i.e., N factor-introduced cell line) were established. The four types of stable cell lines were dissociated into single cells using Accutase (Thermo), and then seeded into a 12-well plate which had been coated with matrigel (BD) and 0.01 mg/ml human fibronectin (BD) at 30×10$^4$ cells/well. Then, those cells were cultured in the DOX-containing medium (i.e., Neurobasal medium (Life Technologies) supplemented with 2 μg/μl DOX and B-27 Supplement Minus AO (Life Technologies)) to induce the expression of the Ngn2. The medium was exchanged for fresh medium with the same composition on the 5th day after the induction. Although βIII tublin-positive cells was hardly observed by the 4th day, the number of βIII tublin-positive cells rapidly increased from the 5th day to the 7th day, but no longer increased on or after the 8th day after initiating the induction of Ngn2 expression. There was no significant difference in the time courses of βIII tublin-positive cell production among the four types of N factor-introduced stable cell lines.

Accordingly, it was clarified that, when Ngn2 gene is introduced and allowed to express in human-derived pluripotent stem cells, the cells are synchronously converted into iN from the 5th day to the 7th day after induction of the Ngn2 gene expression.
<Evaluation of the Properties of iN Generated from the iPS Cells Derived from a Patient with Alzheimer's Type Dementia>

It has been reported that the processing of APP protein is altered and thereby the amount of Aβ40 peptide and Aβ42 peptide tends to be increased in the brain of a patient with Alzheimer's type dementia. In particular, since the Aβ42 peptide is prone to aggregate and produce cytotoxicity, a compound capable of suppressing the production of Aβ42 peptide has been vigorously searched as a therapeutic agent (candidate) for the disease.

Hence, we assessed the amounts of the two types of Aβ peptides secreted into the culture medium of the iN generated from the patient-derived pluripotent stem cells.

The four types of stable iPS cell lines were divided into three groups on the 7th day after induction of the expression of Ngn2, then subjected to any one of the following treatments 1) to 3), and then cultured for 4 days (the photographs of the cells at this time point are shown in FIG. 16B.)
1) DMSO added group (negative control)
2) 1 μM BSI IV added group
3) 100 μM Sulindac sulfide added group (N112E14 (normal control derived), AD8K213 (derived from sporadic Alzheimer's patients), AD15E11 (presenilin (PS1) mutant), APP1E211 (APP-E693 delta))

At the 5th, 7th, 9th, and 11th days after initiation of the induction of Ngn2 expression, a conditioned medium was recovered, and the amounts of the Aβ40 and Aβ42 peptides in the conditioned medium were measured using MSD Abeta 3 plex (38, 40, 42) assay plate (Meso Scale Discovery) (FIG. 16C). In the upper case of FIG. 16B, changes over time in the amounts of individual Aβ peptides are shown. From the figure, it was found that a larger amount of Aβ42 peptide was contained in each of the conditioned medium of iN derived from two patients with Alzheimer's disease (AD8K213 and AD15E11), than in the conditioned medium of iN derived from a normal control (N112E14). In particular, in the case of AD15E11-derived iN that has a mutation causing an increase of Aβ42 peptide production, the amount of Aβ42 peptide in the conditioned medium became highest. In contrast, in the case of APP1E211-derived iN, Aβ42 peptide was hardly detected in the conditioned medium, although the iN was derived from a patient. It has been reported that, in the neurons having APP1E211 mutation, the Aβ42 peptide is not secreted outside of cells and accumulated within the neurons. Accordingly, it can be considered that all of the iN derived from these three patients could sufficiently reproduce the original properties of the neurons from which they had been derived. Moreover, it was found that, in all of the iN other than the APP1E211-derived iN secreting almost no Aβ42 peptide, the amount of Aβ peptide became largest in the conditioned medium recovered on the 9th day after initiation of the induction of Ngn2 expression (namely, the amount of the peptide secreted into the medium during a period from the 7th day to the 9th day).

Subsequently, the sensitivity of the four types of iN to the existing inhibitors of Aβ40 and/or Aβ42 production was analyzed (the middle and lower cases of FIG. 16C). In all of the iN, when BSI, β-secretase inhibitor, was added, the amounts of Aβ40 and Aβ42 peptides significantly descreased in the medium during a period from the 7$^{th}$ to 9th days (the lower case of FIG. 16C) and the 9th to 11th days (the lower case of FIG. 16C) after initiation of the induction of Ngn2 expression. In contrast, when Sulindac Sulfide that is a γ-secretase modulator capable of inhibiting Aβ42 production more strongly than Aβ40 production (Takahashi Y, et al, The Journal of Biological Chemistry, 2003, 278: see 18664-18670) was added, Aβ42 production tended to be inhibited more strongly than Aβ40 production, in particular, in the patients (AD8K213 and AD15E11)-derived iN (the middle and lower cases of FIG. 16C). Therefore, it became clear that the iN could acquire a similar sensitivity to those inhibitors of Aβ40 and/or Aβ42 production as that of a native neuron by 7 to 9 days after the induction of the expression of Ngn2.

From these results, the iN, which has been induced from pluripotent stem cells derived from a patient with Alzheimer's type dementia according to the method of the present invention, is thought to be preferably used as a screening system for an inhibitor of Aβ production pathway, since the cell can sufficiently produce Aβ peptide characteristic to the patient with Alzheimer's disease in 9 days after the induction. Taking into consideration the fact that it takes approximately two months to obtain such mature neurons from pluripotent stem cells by the conventional methods (e.g., the adhesion method), the impact of the present invention will be extremely large.

Example 12: In Vivo Generation of iMN from the Pluripotent Stem Cell

In Examples 1 to 11 of the present application, for the pluripotent stem cells in which the DNA encoding MN factor or Ngn2 under the control of a drug responsive promoter had been introduced, an induction of the expression of MN factor or Ngn2 was carried out in culture by adding a drug for inducing activation of the promotor into the medium. Thus, we next asked whether this induction process could be carried out in a living body.

The mouse ES cells that were prepared in Example 1 so as to visualize iMN (i.e., KH2 cells, into the genome of which the DNA shown in FIG. 1A and a DNA fragment having the coding sequence of GFP joined to HB9 gene promoter (HB9::GFP) had been inserted) were transplanted into the spinal cord of NOG mice. Thereafter, the mice were subjected to administration in drinking water containing DOX and also to intraperitoneal administration with retinoic acid, and two weeks after the transplantation, the injection sites of the cells were immunestained. As a result, the largest quantities of GFP-positive cells (namely, iMN) were observed in the mouse that had been administered with DOX and retinoic acid from one week before the transplantation (FIG. 17). Moreover, the GFP-positive cells were positive to Tuj1, and extended neurites, demonstrating that those cells survived in the spinal cord of the transplanted mice (FIG. 17).

Therefore, it was demonstrated that the pluripotent stem cells according to the present invention (namely, pluripotent stem cells, into which DNA encoding MN factor under the control of a drug responsive promoter had been introduced) can be converted into a motor neuron even in animal bodies. Taking into consideration the results of Example 9 (specifically, the pluripotent stem cells according to the present invention are allowed to differentiate into blood cells, and thereafter, can be converted to iMN by inducing the expression of MN factor), it would be possible to introduce the blood cells induced from the pluripotent stem cells according to the present invention, instead of the pluripotent stem cells themselves, into an animal body, and thereafter, to induce differentiation of the blood cells into iMN in the animal body.

Example 13: In Vivo Generation of iN from the Pluripotent Stem Cell

Likewise, the MN factor-introduced human-derived iPS cells (201B7 Ngn2 cells), which had been prepared in Example 5, were transplanted into the hippocampus of an NOG mouse one week after administration in drinking water containing DOX. Four weeks after the transplantation, the brain slices including the injection site were immunostained, and hNCAM-positive cells were detected (FIG. 18). From these results, it was confirmed that the human-derived iPS cell could be converted into a euron in mouse brain and could survive therein.

Accordingly, it was suggested that a model mouse having human cells can be generated by inducing the ES/iPS cell into neurons or motor neurons in brain or spinal cord of mouse by using the present invention. Such model mouse is useful for examining a candidate pharmaceutical product in vivo. Moreover, it was also suggested that a transplantation of pluripotent stem cells into a desired site and following induction of conversion of them into motor neurons or neurons in vivo can facilitate the engraftment of those neurons.

Example 14

To date, the development of an iPS cell technology has been promoted for the main purpose of preparing disease models or preparing tissues or cells to be transplanted. In addition, in the field of drug discovery and/or clinical trial, stability tests have been carried out using healthy subject-derived iPS cells, and the effectiveness of a test drug has been evaluated using patient-derived iPS cells, so as to discover a novel candidate therapeutic agent. That is to say, a use of an iPS cell technology, which comprises searching and/or developing a candidate drug in an experimental system using iPS cells, and thereafter, conducting a clinical trial using subjects, has been settled as a concept.

However, in the analysis of existing drugs using the ALS patients (two patients)-derived iPS cells into which the MN factor had been introduced, there were found several compounds whose reactivity was significantly different between the iPS cells derived from different patients (in the present application, the disclosure of the results has been omitted). These compounds were reported to have a large variation in reactivity among patients, and thus, were concluded to have no significance.

These results suggest that, if the MN analysis system according to the present invention is used, it is likely to analyze, in detail, differences in drug reactivity among cell donors (individuals), and to clarify the reason for causing such differences. Furthermore, if a subject group for which a specific drug is effective (=responders) or not effective (=non-responders) is determined as a result of actual clinical trials, it would be possible to find a certain characteristic common to each group (=a marker) by establishing iPS cells from the responders and non-responders, differentiating the iPS cells into iMN, and then analyzing according to the method of the present invention. If such a marker is found, only responder who has the marker can select as the subject to be tested in a phase II clinical trial, and thus, a highly accurate clinical trial can be conducted using a relatively small number of subjects.

FIG. 19 shows a conceptual view showing a clinical trial using responder/non-responder markers. With regard to a test drug that has been determined to be "no effectiveness" as a result of a conventional phase II trial, first, cells are provided from subjects for whom the test drug has been effective (=responders) and subjects for whom it has not been effective (=non-responders), and then, iPS cell lines are each established from the cells. Subsequently, various analyses (transcriptome, proteome, metabolome, epigenetic analysis, etc.) are performed on the established iPS cells, and/or cells and/or tissues prepared from the iPS cells, so as to find a characteristic common to the responders or non-responders (=a marker). Thereafter, only subjects having the responder marker, or only subjects having the non-responder marker are gathered, and are subjected to a phase II trial again. When the test drug is effective for the subjects having the responder marker, the drug is considered to be a therapeutic agent for humans having the responder marker, and to be tested in a phase III trial.

That is to say, this is a use of an iPS cell technology opposite to the conventional use, which comprises classifying subjects from the results of a clinical trial, and thereafter, analyzing the subjects using an iPS cell technology.

INDUSTRIAL APPLICABILITY

According to the present invention, since homogenous motor neurons or neurons can be efficiently induced from pluripotent stem cells, an excellent cell model for neurodegenerative disease or nerve injury, which is useful for searching for a therapeutic agent for the disease, can be provided. In addition, the blood cells that have differentiated from the present pluripotent stem cells capable of being induced into motor neurons, can be directly induced into motor neurons. Since blood cells are predisposed to accumulate in an affected area where motor neurons have disappeared, the blood cells differentiated from the present pluripotent stem cells are useful for the treatment of neurodegenerative disease or nerve injury.

What is claimed is:

1. A method of generating a motor neuron from a pluripotent stem cell in vitro, comprising in order from (1) to (3):
   (1) introducing a vector comprising an inducible promoter operably linked to Lhx3, Ngn2, and Isl1 genes into the pluripotent stem cell;
   (2) inducing expression of the Lhx3, Ngn2, and Isl1 genes in the pluripotent stem cell from (1) in KSR media or N3 media containing a drug capable of inducing an activation of the promoter; and
   (3) culturing the pluripotent stem cell from (2) and maintaining expression of the Lhx3, Ngn2, and Isl1 genes for three days or more in said cell, thereby producing a motor neuron.

2. The method according to claim 1, wherein Lhx3, Ngn2, and Isl1 genes are polycistronically expressed from the one or more nucleic acids.

3. The method according to claim 1, wherein expression of the Lhx3, Ngn2, and Isl1 genes is maintained for 7 days or more in step (2).

4. The method according to claim 1, wherein said pluripotent stem cell is an induced pluripotent stem cell derived from a human.

5. The method according to claim 1, wherein said pluripotent stem cell has one or more mutant SOD1 genes.

6. The method according to claim 1, wherein in step (2), expression of the Lhx3, Ngn2, and Isl1 genes in the pluripotent stem cell from (1) is induced in N3 media containing the drug capable of inducing an activation of the promoter.

7. The method according to claim 1, wherein in step (2), expression of the Lhx3, Ngn2, and Isl1 genes in the pluripotent stem cell from (1) is induced in KSR media containing the drug capable of inducing an activation of the promoter.

* * * * *